(12) United States Patent
Matyjaszewski et al.

(10) Patent No.: US 10,072,042 B2
(45) Date of Patent: Sep. 11, 2018

(54) ATOM TRANSFER RADICAL POLYMERIZATION UNDER BIOLOGICALLY COMPATIBLE CONDITIONS

(71) Applicant: Carnegie Mellon University, Pittsburgh, PA (US)

(72) Inventors: Krzysztof Matyjaszewski, Pittsburgh, PA (US); Saadyah E. Averick, Pittsburgh, PA (US); Antonina Simakova, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 64 days.

(21) Appl. No.: 15/378,537

(22) Filed: Dec. 14, 2016

(65) Prior Publication Data
US 2017/0145048 A1    May 25, 2017

Related U.S. Application Data

(63) Continuation of application No. 14/239,181, filed as application No. PCT/US2012/051855 on Aug. 22, 2012.

(60) Provisional application No. 61/690,688, filed on Jul. 2, 2012, provisional application No. 61/575,482, filed on Aug. 22, 2011.

(51) Int. Cl.
| | | |
|---|---|---|
| *C07K 1/107* | (2006.01) | |
| *C08G 81/02* | (2006.01) | |
| *C08F 283/06* | (2006.01) | |
| *C07K 14/435* | (2006.01) | |
| *C07K 14/765* | (2006.01) | |

(52) U.S. Cl.
CPC ...... *C07K 1/1077* (2013.01); *C07K 14/43595* (2013.01); *C07K 14/765* (2013.01); *C08F 283/06* (2013.01); *C08G 81/025* (2013.01)

(58) Field of Classification Search
CPC .......... C07K 1/1077; C07K 14/765; C07K 14/43595; C08G 81/025; C08F 283/06
See application file for complete search history.

(56) References Cited

U.S. PATENT DOCUMENTS

| | | |
|---|---|---|
| 3,037,004 A | 5/1962 | Simone et al. |
| 3,096,312 A | 7/1963 | Henry |
| 3,183,217 A | 5/1965 | Serniuk et al. |
| 3,350,374 A | 10/1967 | Fetscher et al. |
| 3,397,186 A | 8/1968 | Edward et al. |
| 3,472,826 A | 10/1969 | Potts et al. |
| 3,546,083 A | 12/1970 | Ort et al. |
| 3,573,180 A | 3/1971 | Hodes et al. |
| 3,716,550 A | 2/1973 | Gilligan et al. |
| 3,753,956 A | 8/1973 | Tuites et al. |
| 3,862,978 A | 1/1975 | Decker et al. |
| 3,953,305 A | 4/1976 | Connolly |
| 3,959,225 A | 5/1976 | Kuntz |
| 3,963,491 A | 6/1976 | Marsh |
| 4,007,165 A | 2/1977 | MacLeay et al. |
| 4,073,870 A | 2/1978 | Saji et al. |
| 4,145,486 A | 3/1979 | Haag et al. |
| 4,302,553 A | 11/1981 | Frisch et al. |
| 4,374,751 A | 2/1983 | Dudgeon |
| 4,384,093 A | 5/1983 | Culbertson et al. |
| 4,581,429 A | 4/1986 | Solomon et al. |
| 4,728,706 A | 3/1988 | Farnham et al. |
| 4,806,605 A | 2/1989 | Hertler |
| 4,925,765 A | 5/1990 | Madeleine |
| 4,940,648 A | 7/1990 | Geiger |
| 4,940,760 A | 7/1990 | Boettcher et al. |
| 4,954,416 A | 9/1990 | Wright et al. |
| 4,978,498 A | 12/1990 | Yoshihiro et al. |
| 5,026,813 A | 6/1991 | Meder |
| 5,089,135 A | 2/1992 | Yoneyama et al. |
| 5,102,967 A | 4/1992 | Meder |
| 5,169,914 A | 12/1992 | Kaszas et al. |
| 5,210,109 A | 5/1993 | Tateosian et al. |
| 5,212,043 A | 5/1993 | Yamamoto et al. |
| 5,248,746 A | 9/1993 | Shimokawa et al. |
| 5,254,651 A | 10/1993 | Alexanian et al. |
| 5,281,681 A | 1/1994 | Austin |
| 5,294,678 A | 3/1994 | Tse et al. |
| 5,312,871 A | 5/1994 | Mardare et al. |
| 5,322,912 A | 6/1994 | Georges et al. |

(Continued)

FOREIGN PATENT DOCUMENTS

| | | |
|---|---|---|
| CA | 2209061 | 2/1998 |
| CN | 1084199 A | 3/1994 |

(Continued)

OTHER PUBLICATIONS

Gao et al; Proceedings of the National Academy of Sciences, 2009, vol. 106, No. 36, p. 15231-15236.*
Lele et al; Biomacromolecules, 2005, vol. 6, p. 3380-3387.*
De et al; Journal of the American Chemical Society, 2008, vol. 130, p. 11288-11289, SI1-SI21.*
Qian et al; Analytical Chemistry, 2009, vol. 81, No. 11, p. 4536-4542.*
Acar et al., Macromolecules 2000, 33, 7700-7706.
Anderegg et al., "Pyridine Derivatives as Complexing Agents XI. Thermodynamics of Metal Complex Formation with Bis-, Tris- and Tetrakisl(2-pyridyl)methyl]-amines", Helvetica Chimica Acta, 1977, 60(1), pp. 123-140.

(Continued)

*Primary Examiner* — Robert S Jones
(74) *Attorney, Agent, or Firm* — K&L Gates LLP

(57) ABSTRACT

Methods for conducting controlled grafting-from radical polymerizations from biomolecules under conditions that are biologically compatible are described. The methods provide biomolecule-polymer conjugates with highly controlled structures and narrow polydispersities under aqueous reaction conditions and biological temperatures. Biomolecules, such as proteins and nucleotides can be conjugated to polymers with high levels of control.

18 Claims, 14 Drawing Sheets

(56) References Cited

U.S. PATENT DOCUMENTS

| | | |
|---|---|---|
| 5,324,879 A | 6/1994 | Hawthorne |
| 5,331,088 A | 7/1994 | Meister et al. |
| 5,346,954 A | 9/1994 | Wu et al. |
| 5,362,813 A | 11/1994 | Antonelli et al. |
| 5,401,804 A | 3/1995 | Georges et al. |
| 5,405,913 A | 4/1995 | Harwood et al. |
| 5,451,647 A | 9/1995 | Faust et al. |
| 5,459,222 A | 10/1995 | Rodgers et al. |
| 5,470,928 A | 11/1995 | Harwood et al. |
| 5,506,312 A | 4/1996 | Arjunan |
| 5,508,353 A | 4/1996 | Liu et al. |
| 5,510,212 A | 4/1996 | Delnick et al. |
| 5,510,307 A | 4/1996 | Narayanan et al. |
| 5,543,158 A | 8/1996 | Gref et al. |
| 5,558,954 A | 9/1996 | Morrison |
| 5,610,250 A | 3/1997 | Veregin et al. |
| 5,630,906 A | 5/1997 | Boe et al. |
| 5,656,708 A | 8/1997 | Meister |
| 5,668,188 A | 9/1997 | Whinnery et al. |
| 5,700,844 A | 12/1997 | Liao et al. |
| 5,705,577 A | 1/1998 | Rossi et al. |
| 5,708,102 A | 1/1998 | Fryd et al. |
| 5,763,546 A | 6/1998 | Jung et al. |
| 5,763,548 A | 6/1998 | Matyjaszewski et al. |
| 5,767,210 A | 6/1998 | Lecomte et al. |
| 5,773,538 A | 6/1998 | Feiring |
| 5,789,487 A | 8/1998 | Matyjaszewski et al. |
| 5,807,937 A | 9/1998 | Matyjaszewski et al. |
| 5,811,500 A | 9/1998 | Dubois et al. |
| 5,833,320 A | 11/1998 | Kaneko et al. |
| 5,854,364 A | 12/1998 | Senninger et al. |
| 5,886,118 A | 3/1999 | Percec |
| 5,891,971 A | 4/1999 | Keoshkerian et al. |
| 5,910,549 A | 6/1999 | Matyjaszewski et al. |
| 5,945,491 A | 8/1999 | Matyjaszewski et al. |
| 5,998,537 A | 12/1999 | Good et al. |
| 6,031,017 A | 2/2000 | Waki et al. |
| 6,054,507 A | 4/2000 | Funaki et al. |
| 6,057,042 A | 5/2000 | Shimotsu |
| 6,083,524 A | 7/2000 | Sawhney et al. |
| 6,111,022 A | 8/2000 | Matyjaszewski et al. |
| 6,114,448 A | 9/2000 | Derbes |
| 6,114,482 A | 9/2000 | Senniger et al. |
| 6,121,371 A | 9/2000 | Matyjaszewski et al. |
| 6,124,411 A | 9/2000 | Matyjaszewski et al. |
| 6,126,919 A | 10/2000 | Stefely et al. |
| 6,143,848 A | 11/2000 | Lee et al. |
| 6,162,882 A | 12/2000 | Matyjaszewski et al. |
| 6,183,866 B1 | 2/2001 | Yamazaki et al. |
| 6,191,197 B1 | 2/2001 | Wang et al. |
| 6,235,822 B1 | 5/2001 | Whetten et al. |
| 6,254,854 B1 | 7/2001 | Edwards et al. |
| 6,255,448 B1 | 7/2001 | Grimaldi et al. |
| 6,288,186 B1 | 9/2001 | Matyjaszewski et al. |
| 6,310,149 B1 | 10/2001 | Haddleton |
| 6,319,988 B1 | 11/2001 | Barkac et al. |
| 6,326,455 B2 | 12/2001 | Vassiliou et al. |
| 6,342,563 B1 | 1/2002 | McGinniss et al. |
| 6,407,187 B1 | 6/2002 | Matyjaszewski et al. |
| 6,451,580 B1 | 9/2002 | Takagi et al. |
| 6,512,060 B1 | 1/2003 | Matyjaszewski et al. |
| 6,534,610 B1 | 3/2003 | Wilson et al. |
| 6,538,091 B1 | 3/2003 | Matyjaszewski et al. |
| 6,541,580 B1 | 4/2003 | Matyjaszewski et al. |
| 6,545,095 B1 | 4/2003 | Solomon et al. |
| 6,565,763 B1 | 5/2003 | Asakawa et al. |
| 6,592,991 B1 | 7/2003 | Wiesner et al. |
| 6,598,721 B2 | 7/2003 | Schmidl |
| 6,620,927 B2 | 9/2003 | Bulpitt et al. |
| 6,624,262 B2 | 9/2003 | Matyjaszewski et al. |
| 6,624,263 B2 | 9/2003 | Matyjaszewski et al. |
| 6,627,314 B2 | 9/2003 | Matyjaszewski et al. |
| 6,664,312 B2 | 12/2003 | Devonport |
| 6,670,299 B1 | 12/2003 | Marks et al. |
| 6,672,717 B2 | 1/2004 | Smith |
| 6,683,120 B2 | 1/2004 | Munro |
| 6,686,432 B2 | 2/2004 | Coca et al. |
| 6,692,914 B1 | 2/2004 | Klaerner et al. |
| 6,737,488 B2 | 5/2004 | Vanhoorne et al. |
| 6,759,491 B2 | 7/2004 | Matyjaszewski et al. |
| 6,784,247 B2 | 8/2004 | Rechenberg et al. |
| 6,784,248 B2 | 8/2004 | Coca et al. |
| 6,784,260 B2 | 8/2004 | Yeager et al. |
| 6,790,919 B2 | 9/2004 | Matyjaszewski et al. |
| 6,828,025 B2 | 12/2004 | Ali et al. |
| 6,872,266 B1 | 3/2005 | Ciaramitaro |
| 6,887,962 B2 | 5/2005 | Matyjaszewski et al. |
| 6,991,652 B2 | 1/2006 | Burg |
| 6,992,156 B2 | 1/2006 | Parker et al. |
| 7,018,655 B2 | 3/2006 | Lele et al. |
| 7,019,082 B2 | 3/2006 | Matyjaszewski et al. |
| 7,034,079 B2 | 4/2006 | Visger et al. |
| 7,037,992 B2 | 5/2006 | Wilson et al. |
| 7,049,373 B2 | 5/2006 | Matyjaszewski et al. |
| 7,049,378 B2 | 5/2006 | Ittel et al. |
| 7,056,455 B2 | 6/2006 | Matyjaszewski et al. |
| 7,064,151 B1 | 6/2006 | Berge et al. |
| 7,064,166 B2 | 6/2006 | Matyjaszewski et al. |
| 7,105,579 B2 | 9/2006 | Adam et al. |
| 7,125,938 B2 | 10/2006 | Matyjaszewski et al. |
| 7,157,530 B2 | 1/2007 | Matyjaszewski et al. |
| 7,167,354 B2 | 1/2007 | Dietz et al. |
| 7,186,419 B2 | 3/2007 | Petersen |
| 7,241,502 B2 | 7/2007 | Anselmann et al. |
| 7,332,550 B2 | 2/2008 | Matyjaszewski et al. |
| 7,407,995 B2 | 8/2008 | Ok |
| 7,498,456 B2 | 3/2009 | Lai |
| 7,566,410 B2 | 7/2009 | Song et al. |
| 7,572,874 B2 | 8/2009 | Matyjaszewski et al. |
| 7,678,869 B2 | 3/2010 | Matyjaszewski et al. |
| 7,691,997 B2 | 4/2010 | Khvorova et al. |
| 7,786,213 B2 | 8/2010 | Maynard et al. |
| 7,795,355 B2 | 9/2010 | Matyjaszewski et al. |
| RE41,897 E | 10/2010 | Loveday et al. |
| 7,825,199 B1 | 11/2010 | Matyjaszewski et al. |
| 7,893,173 B2 | 2/2011 | Matyjaszewski et al. |
| 7,893,174 B2 | 2/2011 | Matyjaszewski et al. |
| 7,968,085 B2 | 6/2011 | Hersel et al. |
| 8,048,982 B2 | 11/2011 | Higashimura et al. |
| 8,114,803 B2 | 2/2012 | Yuasa et al. |
| 8,252,880 B2 | 8/2012 | Matyjaszewski et al. |
| 8,273,823 B2 | 9/2012 | Matyjaszewski et al. |
| 8,318,856 B2 | 11/2012 | Oh et al. |
| 8,349,410 B2 | 1/2013 | Huang et al. |
| 8,361,302 B2 | 1/2013 | Grassl et al. |
| 8,367,051 B2 | 2/2013 | Matyjaszewski et al. |
| 8,404,788 B2 | 3/2013 | Matyjaszewski et al. |
| 8,445,610 B2 | 5/2013 | Kwak et al. |
| 8,497,225 B2 | 7/2013 | Zhamu et al. |
| 8,637,051 B2 | 1/2014 | Clancy et al. |
| 8,652,849 B2 | 2/2014 | Childs et al. |
| 8,729,173 B2 | 5/2014 | Wang et al. |
| 8,865,797 B2 | 10/2014 | Matyjaszewski et al. |
| 8,871,831 B2 | 10/2014 | Huang et al. |
| 8,962,764 B2 | 2/2015 | Matyjaszewski et al. |
| 9,093,693 B2 | 7/2015 | Zhamu et al. |
| 9,410,020 B2 | 8/2016 | Matyjaszewski et al. |
| 2002/0169290 A1 | 11/2002 | Bornaes et al. |
| 2003/0004293 A1 | 1/2003 | Dvornic et al. |
| 2003/0216528 A1 | 11/2003 | Matyjaszewski et al. |
| 2004/0044152 A1 | 3/2004 | Matyjaszewski et al. |
| 2004/0152821 A1 | 8/2004 | Saegusa et al. |
| 2004/0171779 A1 | 9/2004 | Matyjaszewski et al. |
| 2005/0090632 A1 | 4/2005 | Matyjaszewski et al. |
| 2006/0008490 A1 | 1/2006 | Russell et al. |
| 2006/0258867 A1 | 11/2006 | Gibson et al. |
| 2007/0106012 A1 | 5/2007 | Matyjaszewski et al. |
| 2007/0155926 A1 | 7/2007 | Matyjaszewski et al. |
| 2007/0287681 A1 | 12/2007 | Jeong et al. |
| 2008/0002146 A1 | 1/2008 | Stachowski |
| 2008/0004398 A1 | 1/2008 | Durrieu et al. |
| 2008/0114128 A1 | 5/2008 | Destarac et al. |
| 2008/0176040 A1 | 7/2008 | Ilfrey et al. |
| 2009/0169725 A1 | 7/2009 | Zhamu et al. |

(56) References Cited

U.S. PATENT DOCUMENTS

| | | | |
|---|---|---|---|
| 2009/0171024 A1 | 7/2009 | Jakubowski et al. | |
| 2009/0312505 A1* | 12/2009 | Matyjaszewski | C08F 2/40 526/90 |
| 2010/0196277 A1 | 8/2010 | DeSimone et al. | |
| 2011/0060107 A1 | 3/2011 | Matyjaszewski et al. | |
| 2011/0065875 A1 | 3/2011 | Matyjaszewski et al. | |
| 2011/0091957 A1 | 4/2011 | Lele et al. | |
| 2012/0213986 A1 | 8/2012 | Matyjaszewski et al. | |
| 2013/0011441 A1 | 1/2013 | Hollinger et al. | |
| 2013/0131278 A1 | 5/2013 | Huang et al. | |
| 2014/0183055 A1 | 7/2014 | Matyjaszewski et al. | |
| 2014/0275420 A1 | 9/2014 | Matyjaszewski et al. | |
| 2015/0087795 A1 | 3/2015 | Matyjaszewski et al. | |

FOREIGN PATENT DOCUMENTS

| | | |
|---|---|---|
| CN | 1110681 A | 3/1994 |
| CN | 1165828 A | 11/1997 |
| EP | 0265091 A1 | 4/1988 |
| EP | 0329873 B1 | 11/1989 |
| EP | 0341012 A2 | 11/1989 |
| EP | 0434438 A | 6/1991 |
| EP | 0457916 A | 11/1991 |
| EP | 0789036 A1 | 8/1997 |
| EP | 0816385 A1 | 1/1998 |
| EP | 0824110 A1 | 2/1998 |
| EP | 0824111 A1 | 2/1998 |
| EP | 0826698 A1 | 3/1998 |
| EP | 0832902 A2 | 4/1998 |
| EP | 0870809 A2 | 10/1998 |
| EP | 0872493 A | 10/1998 |
| EP | 0879832 A1 | 11/1998 |
| EP | 0947527 A1 | 6/1999 |
| EP | 0518225 B2 | 10/1999 |
| EP | 1386935 A | 2/2004 |
| EP | 1469020 A | 10/2004 |
| EP | 1555273 A1 | 7/2005 |
| EP | 2147067 | 11/2008 |
| FR | 2777091 A1 | 10/1999 |
| JP | 64-11114 A | 1/1989 |
| JP | 6322171 A | 11/1994 |
| JP | 2003-238609 A | 8/2003 |
| JP | 2011-246620 A | 12/2011 |
| WO | WO 88/00603 A3 | 1/1988 |
| WO | WO 94/13706 A | 6/1994 |
| WO | WO 96/30421 A1 | 10/1996 |
| WO | WO 97/18247 | 5/1997 |
| WO | WO 97/47661 A1 | 12/1997 |
| WO | WO 98/01480 | 1/1998 |
| WO | WO 98/06758 A1 | 2/1998 |
| WO | WO 98/20050 A2 | 5/1998 |
| WO | WO 98/40415 A | 9/1998 |
| WO | WO 99/28352 A | 6/1999 |
| WO | WO 00/22051 A1 | 4/2000 |
| WO | WO 00/47634 A1 | 8/2000 |
| WO | WO 00/56795 A1 | 9/2000 |
| WO | WO 00/75198 | 12/2000 |
| WO | WO 01/77197 A3 | 10/2001 |
| WO | WO 01/92359 A1 | 12/2001 |
| WO | WO 2002/081372 A2 | 10/2002 |
| WO | WO 2003/097107 A | 11/2003 |
| WO | WO 2004/041972 A | 5/2004 |
| WO | WO 2004/060928 A | 7/2004 |
| WO | WO 2004/087777 A2 | 10/2004 |
| WO | WO 2005/056621 A1 | 6/2005 |
| WO | WO 2005/087819 A1 | 9/2005 |
| WO | WO 2005/116097 A1 | 12/2005 |
| WO | WO 2007/021142 A1 | 2/2007 |
| WO | WO 2007/025086 A2 | 3/2007 |
| WO | WO 2007/025310 A1 | 3/2007 |
| WO | WO 2007/059350 A2 | 5/2007 |
| WO | WO 2007/075817 A1 | 7/2007 |
| WO | WO 2008/009997 A1 | 1/2008 |
| WO | WO 2008/057163 A2 | 5/2008 |
| WO | WO 2008/148000 A1 | 12/2008 |
| WO | WO 2009/023353 A9 | 2/2009 |
| WO | WO 2009/065077 A1 | 5/2009 |
| WO | WO 2009/108822 A1 | 9/2009 |
| WO | WO 2009/111725 A1 | 9/2009 |
| WO | WO 2009/132206 A1 | 10/2009 |
| WO | WO 2009/132884 A1 | 11/2009 |
| WO | WO 2010/096422 A1 | 8/2010 |
| WO | WO 2010/111708 A1 | 9/2010 |
| WO | WO 2010/131907 A2 | 11/2010 |
| WO | WO 2012/034043 A1 | 3/2012 |
| WO | WO 2012/091965 A1 | 7/2012 |
| WO | WO 2013/063772 A1 | 5/2013 |

OTHER PUBLICATIONS

Annenkov et al., Poly-C-vinyltetrazoles: A New Type of Polyacid, Journal of Polymer Science Part A: Polymer Chemistry, 1993, pp. 1903-1906, vol. 31(7).
Ashford et al., "First example of the atom transfer radical polymerisation of an acidic monomer: direct synthesis of methacrylic acid copolymers in aqueius media", Chemical Communications—Chemcom, Royal Society of Chemistry, GB (1999), pp. 1285-1286.
Asscher et al., Chlorine-Activation by Redox-Transfer, Part IV, The Addition of Sulphonyl Chlorides to Vinylic Monomers and Other Olefins, Journal of the Chemical Society, 1964, pp. 4962-4971.
Bamford, Comprehensive Polymer Science (First Supplement), eds., Pergamon: Oxford vol. 3., p. 123-139 (1991).
Baumann et al., Macromolecular Materials and Engineering (2000), 280/281, 1-6.
Bellus, Pure & Appl. Chem. 57, 1827 (1985).
Bledzki et al., Makromol. Chem. 184, 745 (1983).
Braunecker et al., Macromolecules 2005, 38, 4081.
Braunecker et al., Organometal Chem. 2005, 690, 916.
Brittain et al., Makromol. Chem., Macromol. Symp. 67, pp. 373-386 (1993), "Termination Processes in Group Transfer Polymerization".
Buback et al. (1995) Macromol. Chem. Phys. 196, 3267-80.
Buback et al. (2002) Macromol. Chem. Phys. 203, 2570-2582.
Bywater, Makromol. Chem., Macromol. Symp. 67, pp. 339-350 (1993), "Group Transfer Polymerization—A Critical Overview".
Carnahan et al., Synthesis and Characterization of Poly(glycerol-succinic acid) Dendrimers, Macromolecules, 2001, pp. 7648-7655, vol. 34(22).
Carter et al., Polyimide Nanofoams From Phase-Separated Block Copolymers, Electrochemical Society Proceedings, 1997, pp. 32-43, vol. 97(8), Electrochemical Society, Pennington, NJ, US.
Caruso, Nanoengineering of Particle Surfaces—Adv. Mater. 2001, 13, No. 1, Jan. 5, 11-22—Wiley—VCH Verlag GmbH.D—69469 Weinheim, 2001.
Catala, et al., Macromolecules, 1995, 28, 8441.
Chemical Abstracts, vol. 85, 1976, pp. 20.
Chen et al., Pryolytic Behavior and In-Situ Paramagnetism of Star-like C60(CH3)x(PAN)xcopolymers, European Polymer Journal, 1998, pp. 421-429, vol. 34(3-4), Elsevier Science Ltd., Oxford, GB.
Coca et al., Polymerization of Acrylates by Atom Transfer Radical Polymerization. Homopolymerization of 2-Hydroxyethyl Acrylate, Journal of Polymer Science, Part A: Polymer Chemistry, 1998, pp. 1417-1424, vol. 36.
Cohen et al., Inorg. Chem. 13, 2434 (1974).
Collman et al., "Clicking" Functionality onto Electrode Surfaces, Langmuir, 2004, pp. 1051-1053, vol. 20.
Curran, et al., "Radical Addition Reactions", Comprehensive Organic Synthesis, Pergamon: Oxford vol. 4, p. 715-777 (1991).
Curran et al., J. Am. Chem. Soc. 116, 4279 (1994).
Curran et al., J. Org. Chem., 54, 3140 (1989).
Curran, "The Design and Application of Free Radical Chain Reactions in Organic Synthesis Part 2," Synthesis, pp. 489-513 (1988).
Darkow et al., "Synthesis, Photomodification and Characterization of Homo- and Copolymers with 2,5-bisaryltetrazolyl Pendant Groups", Reactive and Functional Polymers, 1997, pp. 195-207, vol. 32(2).
Davies, "Reactions of L-ascorbic acid with transition metal complexes," Polyhedron, 1992, 11, 285-321.

(56) References Cited

OTHER PUBLICATIONS

De Vries et al., "The Effect of Reducing Monosaccharides on the Atom Transfer Radical Polymerization of Butyl Methacrylate," Macromol. Chem. Phys., 2001, 202, 1645-1648.
Demko et al., A Click Chemistry Approach to Tetrazoles by Huisgen 1,3-Dipolar Cycloaddition: Synthesis of 5-Acyltetrazoles from Azides and Acyl Cyanides, Angewandte Chemie, International Edition, 2002, pp. 2113-2116, vol. 41(12).
Desmarquest et al., Electrochim. Acta (1968), 13, 1109-1118.
Dreezen et al., "Nano-Structured Polymer Blends: Phase Structure, Crystallisation Behaviour and Semi-Crystalline Morphology of Phase Separated Binary Blends of Poly(ethyleneoxide) and Poly(ether sulphone)", Polymer, Elsevier Science Publishers B.V., GB, vol. 41, No. 4, Feb. 2000, pp. 1395-1407.
Druliner, Macromolecules, 24, 6079-6082 (1991).
Endo et al., Macromolecules, 25, 5554-5556 (1992).
Feng, "Synthesis and Free Radical Polymerization of 2-oxo-3-methylene-5-phenyl-1,4-dioxan", Chinese Journal of Polymer Science, 1993, 11, 2, pp. 153-157.
Fischer et al., Acc. Chem. Res. 20, 200-206 (1987).
Fischer, H., Chem. Rev. 2001, 101, 3581-3610.
Frackowiak et al., "Supercapacitor electrodes from multiwalled carbon nanotubes", Applied Physics Letters, 77, pp. 2421-2423 (2000).
Fukuda et al, Chem. Letters, 1996, 4, 293.
Fukuda et al., Macromolecules, 1996, 29, 3050.
Gabaston et al., "Synthesis of water soluble homopolymers and block copolymers by living free-radical polymerization", Polymr Preprints (American Chemical Society, Division of Polymer Chemistry), 38(1), pp. 719-720 (1997).
Gaynor et al., Polym. Prep. (Am. Chem. Soc. Polym. Chem. Div.), 36(1), 467 (1995).
Georges et al., Macromolecules 1993, 26, 2987.
Georges et al., Macromolecules 1994, 27, 7228.
Georges et al., Macromolecules, 1993, 26, 5316.
Gilbert & Williams, Reactivity Ratios of Conjugated Dienes Copolymerized in Emulsion at 5°, J. Am. Chem. Soc. 74, (1952), pp. 4114-4118.
Gnanou et al., "Effect of Phenol and Derivatives on Atom Transfer Radical Polymerization in the Presence of Air," Journal Polymer Science, Part A: Polymer Chemistry, 2004, 42, 351-359.
Granel et al., Controlled Radical Polymerization of Methacrylic Monomers in the Presence of Bis(ortho-chelated) Arylnickel (II) Complex and Different Activated Alkyl Halides, Macromolecules, 1996, pp. 8576-8582, vol. 29(27).
Grayson et al., Convergent Dendrons and Dendrimers: From Synthesis to Applications, Chemical Reviews, 2001, pp. 3819-3867, vol. 101(12).
Greszta et al., Gradient Copolymers of Styrene and Acrylonitrille Via Atom Transfer Radical Polymerization, Polymer Preprints, 1997, pp. 709-710, vol. 38(1).
Greszta et al., Macromolecules, 27, 638-644 (1994).
Gromada et al., Simultaneous Reverse and Normal Initiation in Atom Transfer Radical Polymerization, Macromolecules, 2001, pp. 7664-7671, 34(22).
Haddleton et al., "Copper-mediated living radical polymerization utilizing biological and end group modified poly(ethylene-co-butylene) macroinitiators", ACS Symposium Series, 768, (Controlled/Living Radical Polymerization), pp. 182-196 (2000).
Hawker, "Molecular Weight Control by a Living Free Radical Polymerization Process", Journal American Chem. Society, 1994, vol. 116, pp. 11185-11186.
Hawker et al., Macromolecules, 1996, 29, 2686.
Hayes et al., J. Am. Chem. Soc. 110, 5533 (1988).
Hedrick et al., (Dendrimer-like Star Block and Amphiphlic Copolymers by Combination of Ring Opening and Atom Transfer Radicat Polymerization. Macromolecules, 1998, 31, 8671-8705.
Helms et al., Dendronized Linear Polymers via "Click Chemistry", Journal of the American Chemical Society, 2004, pp. 15020-15021, vol. 126(46).

Heuts et al., "Atom transfer radical polymerization in the presence of a thiol: more evidence supporting radical intermediates," Macromol. Chem. Phys., 1999, 200, 1380-1385.
Hirao et al., J. Synth. Org. Chem. (Japan), 52(3), 197 (1994).
Hirao et al., Syn. Lett. 217 (1990).
Hong et al., "Synthesis of water-soluble fluorine-containing block copolymers by atom transfer radical polymerization", 25(4), 302 (2001).
Hovestad et al., Macromolecules 2000, 33, 4048-4052.
Ihre et al., Fast and Convenient Divergent Synthesis of Aliphatic Ester Dendrimers by Anhydride Coupling, Journal of the American Chemical Society, 2001, pp. 5908-5917, vol. 123(25).
Iqbal et al., Chem. Rev. 94, 519 (1994).
Jakubowski et al., "Activators Regenerated by Electron Transfer for Atom Transfer Radical Polymerization of Styrene," Macromolecules, 2006, 39, 39-45.
J-F Lutz et al,. Synthesis and Properties of Copolymers with Tailored Sequence Distribution by Controlled/Living Radical Polymerization, in ACS Symposium Series, Advances in Controlled/living Radical Polymerizations, American Chemical Society Division of Polymer Chemistry, 2003, Chapter 19, pp. 268-282, vol. 854.
Jian et al., Mesoporous carbons with self-assembled high-activity surfaces, Air Force Research Laboratory [Report], Jul. 7, 2006. [Retrieved from http://www.dtic.mil, Search ADA461480].
Jo et al., Effects of Various Copper Salts and Additives on Polymerization of Acrylonitrile by Atom Transfer Radical Polymerization, Polymer Preprints, 1997, pp. 699-700, vol. 38(1).
Jo et al., Polyacrylonitrile with Low Polydispersities by Atom Transfer Radical Polymerization, Polymer Preprints, 1997, pp. 697-698, vol. 38(1).
Kamigata et al., Novel Perfluoroalkylation of Alkenes with Perfluoroalkanesulphonyl Chlorides Catalysed by a Ruthenium (II) Complex, Journal of the Chemical Society, Perkins Transactions 1, 1991, pp. 627-633.
Kato et al., Macromolecules, 28, 1721 (1995).
Kawaguchi et al., "Dispersion Polymerization", in Polymer Particles, Masayoshi Okubo, ed., Adv. Polym. Sci., 2005, 175, 299-328.
Kizhnyaev et al., Vinyltetrazoles: Synthesis and Properties, Russian Chemical Reviews, 2003, pp. 143-164, vol. 72(2).
Kolb et al., Click Chemistry: Diverse Chemical Function from a Few Good Reactions, Angewandte Chemie, International Edition, 2001, pp. 2004-2021, vol. 40(11).
Kosower, E.M., Acc Chem. Res. (1971), 4, 193-198.
Kowalewski et al., Advances in Nanostructured Carbons from Block Copolymers Prepared by Controlled Radical Polymerization Techniques, in Controlled Radical Polymerization: From Synthesis to Materials, American Chemical Society Division of Polymer Chemistry, 2005, Chapter 21, pp. 295-310, vol. 944.
Kwak et al., "ARGET ATRP of methyl methacrylate in the presence of nitrogen-based ligands as reducing agents," Polym. Int. 2009, 58, 242-247.
Lazzari et al., Macromolecular Chemistry and Physics (2005), 206, 1382-1388.
Leduc et al., Dendritic initiators for "Living Radical Polymerizations: A Versatile Approach to the Synthesis of Dendritic-Linear Block Copolymers", J. Am. Chem. Soc. Jun. 26, 1996, 118, 11111.
Lee et al., "Synthesis of carboxylic acid functionalized nanoparticles by reversible addition-fragmentation chain transfer (RAFT) miniemulsion polymerization of styrene", Polymer, Elsevier Science Publishers B.V., GB, vol. 46, No. 11, pp. 3661-3668 (2005).
Lewis et al., Copolymerization VII, Copolymerization of Some Further Monomer Pairs, Apr. 1948, pp. 1527-1529.
Li et al., "Highly ordered carbon nanotube arrays for electronics applications", Applied Physics Letters, 75 pp. 367-369 (1999).
Li et al., ASC Polym. Preprints, 1995, 36(1), 469.
Lingane, "Interpretation of the Polarographic Waves of Complex Metal Ions," Chem. Rev. 1941, 29, 1.
Liu et al., "Poly(N-isopropylacrylamide) hydrogels with improved shrinking kinetics by RAFT polymerization", Mar. 22, 2006, Polymer Elsevier Science Publishers, B.V., GB, pp. 2330-2336.
Majoral et al., Dendrimers Containing Heteroatoms (Si, P, B, Ge, or Bi), Chemical Reviews, 1999, pp. 845-880, vol. 99(3).

(56) References Cited

OTHER PUBLICATIONS

Makino et al., Controlled Atom Transfer Radical Polymerizations of Methyl Methacrylate Under Micellar Conditions, Polymer Preprints, 1988, pp. 288-289, vol. 39(1).
Mao et al., "Controlled polymerizations of 2-(dialkylamino)ethyl methacrylates and their block copolymers in protic solvents at ambient temperature via ATRP", Journal of Polymer Science, Part A Polymer Chemistry, 42(20), pp. 5161-5169 (2004).
Maraval et al., "Lego" Chemistry for the Straightforward Synthesis of Dendrimer, Journal of Organic Chemistry, 2003, pp. 6043-6046, vol. 68(15).
Mardare et al., ACS Polymer Preprints 35(1), 778 (1994).
Mardare et al., Macromolecules, 27, 645 (1994).
Mardare et al., Polym. Prep. (ACS), 36(1), 700-701 (1995).
Marestin et al., Nitroxide Mediated Living Radical Polymerization of Styrene in Emulsion, Macromolecules, 1998, pp. 4041-4044, vol. 31(12).
Matsumoto et al., Synth. Commun. (1985) 15, 515.
Matthews et al., Dendrimers-Branching out from Curiosites into New Technologies, Progress in Polymer Science, 1998, pp. 1-56, vol. 23.
Wang et al., Matyjaszewski ed., Controlled/"Living" Radical Polymerization. Progress in ATRP, NMP, and RAFT, in: ACS Symposium Ser., 2000, Chapter 19, Reverse Atom Transfer Radical Polymerization Using AIBN or BPO as Initiator, pp. 263-275.
Matyjaszewski et al., (Structural Control of Poly(Methyl Methacrylate)-g-poly(Lactic Acid) Graft Copolymers by Atom Transfer Radical Polymerization (ATRP). Macromolecules 2001, 34, 6243-6248.
Matyjaszewski et al., "Controlled/Living Radical Polymerization. Kinetics of the Homogeneous Atom Transfer Radical Polymerization of Styrene," J. Am. Chem. Soc., 1997, 119, 674-680.
Matyjaszewski et al., "Atom transfer radical polymerization", *Chemical Reviews*, 2001, 101, (9), 2921-2990.
Matyjaszewski et al., Controlled/"Living" Radical Polymerization of Styrene and Methly Methacrylate Catalyzed by Iron Complexes1, Macromolecules, 1997, pp. 8161-8164, vol. 30(26).
Matyjaszewski et al., Controlled/Living Radical Polymerization: State of the Art in 2002, in ACS Symposium Series, Advances in Controlled/living Radical Polymerizations, American Chemical Society Division of Polymer Chemistry, 2003, Chapter 1, pp. 2-9, vol. 854.
Matyjaszewski et al., Controlled/Living Radical Polymerization: State of the Art in 2005, in Controlled Radical Polymerization: From Synthesis to Materials, American Chemical Society Division of Polymer Chemistry, 2006, Chapter 1, pp. 2-12, vol. 944.
Matyjaszewski et al., Zerovalent Metals in Controlled/"Living" Radical Polymerization, Macromolecules, 1997, pp. 7348-7350, vol. 30(23).
Matyjaszewski, "The Importance of Exchange Reactions in the Controlled/Living Radical Polymerization in the Presence of Alkoxyamines and Transition Metals", Macromolecule Symposium, 1996, vol. 111, pp. 47-61.
Matyjaszewski, "Radical Nature of Cu-Catalyzed Controlled Radical Polymerizations (Atom Transfer Radical Polymerization)," Macromolecules, 1998, 31, 4710-4717.
Matyjaszewski, K., "Overview: Fundamentals of Controlled/Living Radical Polymerization," American Chemical Society, publication date: Jan. 8, 1998, pp. 2-30, downloaded on Sep. 2, 2009, http://pubs.acs.org.
Matyjaszewski et al., Macromolecules 34, 5125 (2001).
Matyjaszewski et al., Tetrahedron (1997), 53, 15321-15329.
McCarthy et al., Grafting Chromatographic Stationary Phase Substrates by Atom Transfer Radical Polymerization, in Controlled Radical Polymerization: From Synthesis to Materials, American Chemical Society Division of Polymer Chemistry, 2005, Chapter 18, pp. 252-268, vol. 944.
Min et al, "Atom Transfer Radical Dispersion Polymerization of Styrene in Ethanol", Macromolecules, ACS, Washington, DC, US, vol. 40, No. 20, (Oct. 2, 2007), pp. 7217-7221.
Mitani et al., J. Am Chem. Soc. 105, 6719 (1983).
Nagashima, J. Org. Chem. 57, 1682 (1992).
Nagashima, J. Org. Chem. 58, 464 (1993).
Navon et al., Inorg. Chem. 1999, 38, 3484.
Nishikawa et al., Evidence for Living Radical Polymerization of Methyl Methacrylate with Ruthenium Complex: Effects of Protic and Radical Compounds and Reinitiation from the Recovered Polymers, Macromolecules, 1997, pp. 2244-2248, vol. 30(8).
Odell et al., Macromolecules, 1995, 28, 8453.
Odian, Principles of Polymerization, Third Edition, John Wiley & Sons, p. 205-233 (1991).
Orochov et al., Redox-Transfer, Part VI, Determination of Hammet's P-Constant for the Oxidation of Cuprous Chloride by Aromatic Sulphonyl Chlorides, Journal of the Chemical Society (B), (1969), pp. 255-259.
Orochov et al., J. Chem. Soc., Perkin II, 1000 (1973).
Orr, Thermochemical Aspects of Butadiene-Styrene Copolymerization, 1960, pp. 74-82.
Otsu et al., Chem. Express 5(10), 801 (1990).
Otsu et al., Synthesis, Reactivity, and Role of—Vinylbenzyl N,N-Diethyldithiocarbamate as a Monomer-Iniferter in Radical Polymerization, Macromolecules, 1986, pp. 287-290, vol. 19(2).
Pakula et al., Polymers, Particles, and Surfaces with Hairy Coatings: Synthesis, Structure, Dynamics, and Resulting Properties, in ACS Symposium Series, Advances in Controlled/living Radical Polymerizations, American Chemical Society Division of Polymer Chemistry, 2003, Chapter 26, pp. 366-382, vol. 854.
Paoletti et al., Inorg. Chem. 1967, 6, 64.
Paoletti et al., Inorg. Chim. Acta Rev. 1973, 7, 43.
Patten et al., Atom Transfer Radical Polymerization and the Synthesis of Polymeric Materials, Advanced Materials, 1998, pp. 901-915, vol. 10(12).
Patten et al., "Polymers with very low polydispersities from atom transfer radical polymerization", *Science* (Washington, D. C.), 1996, 272, (5263), 866-868.
Percec et al., "Living" Radical Polymerization of Styrene Initiated by Arenesulfonyl Chlorides and Cu1(bpy)nCI, Macromolecules, 1995, pp. 7970-7972, vol. 28(23).
Percec et al., Metal-Catalyzed "Living" Radical Polymerization of Styrene Initiated with Arenesulfonyl Chlorides. From Heterogeneous to Homogeneous Catalyses, Macromolecules, 1996, pp. 3665-3668, vol. 29(10).
Pintauer et al., Toward Structural and Mechanistic Understanding of Transition Metal-Catalyzed Atom Transfer Radical Processes, in ACS Symposium Series, Advances in Controlled/living Radical Polymerizations, American Chemical Society Division of Polymer Chemistry, 2003, Chapter 10, pp. 130-147, vol. 854.
Punna et al., Click Chemistry in Polymer Synthesis, Polymer Preprints, 2004, pp. 778-779, vol. 45(1).
Puts et al., Macromolecules, 1996, 29, 3323.
Qiu et al., "Cyclic Voltammetric Studies of Copper Complexes Catalyzing Atom Transfer Radical Polymerization," Macromolecular Chemistry and Physics, 2000, pp. 1625-1631, vol. 201(14).
Queffelec et al., Optimization of Atom Transfer Radical Polymerization Using Cu(I)/Tris(2-(dimethylamino)ethyl)amine as a Catalyst, Macromolecules, 2000, pp. 8629-8639, vol. 33.
Quirk et al., Makromol. Chem., Macromol. Symp. 67, pp. 351-363 (1993), "Mechanistic Aspects of Group Transfer Polymerization".
Richard et al., Acrylate-Based Block Copolymers Prepared by Atom Transfer Radical Polymerization as Matrices for Drug Delivery Applications, in Controlled Radical Polymerization: From Synthesis to Materials, American Chemical Society Division of Polymer Chemistry, 2005, Chapter 17, pp. 234-251, vol. 944.
S.A.F. Bon et al., Controlled Radical Polymerization in Emulsion, Macromolecules, 1997, pp. 324-326, vol. 30(2).
Samuni et al., "On the cytotoxicity of vitamin C and metal ions," European Journal of Biochemistry, 1983, 137. 119-124.
Schubert et al., Design of Effective Systems for Controlled Radical Polymerization of Styrene: Application of 4,4'-Dimethyl and 5,5'-Dimethyl 2,2'-Bipyridine Copper(ii) Complexes, Macromolecular Rapid Communication, 1999, pp. 351-355, vol. 20.
Schulz & Milkovich, Relative Reactivities and Graft Distributions of Polystyrene Macromers in Vinyl Chloride Copolymerization, Polymer International, 1994, pp. 141-149, Great Britain.

(56) References Cited

OTHER PUBLICATIONS

Seijas et al., Tetrahedron, 48(9), 1637 (1992).
Shen et al., Supported Atom Transfer Radical Polymerization of Methyl Methacrylate Mediated by CuBr-Tetraethyldiethylenetriamine Grafted onto Silica Gel—Journal of Polymer Science: Part A: Polymer Chemistry, vol. 39, 1051-1059 (2001); John Wiley & Sons, Inc.
Srivastava et al., J. Inorg. Nucl. Chem. (1980), 42, 47.
Stille et al., Synthesis and Copolymerization of Styryl-Substituted Tetrazoles. Thermal Cross-Linking of Copolymers Containing Dipolarophiles and the Tetrazoles as Nitrile Imine Dipole Precursors, Macromolecules, 1972, pp. 377-384, vol. 5(4).
Sumerlin et al., Click Functionalization of Well-Defined Copolymers Prepared by Atom Transfer Radical Polymerization, in Controlled Radical Polymerization: From Synthesis to Materials, American Chemical Society Division of Polymer Chemistry, 2005, Chapter 11, pp. 140-152, vol. 944.
Takeichi et al., Preparation of Porous Carbon Films by the Pyrolysis of Poly(Urethane-imide) Films and Their Pore Characteristics, Carbon, 2001, pp. 257-265, vol. 39(2).
Tang, et al., J. Am. Chem. Soc., 128, 1598-1604.
Tsarevesky et al., Factors Determining the Performance of Copper-Based Atom Transfer Radical Polymerization Catalysts and Criteria for Rational Catalyst Selection, in Controlled Radical Polymerization: From Synthesis to Materials, American Chemical Society Division of Polymer Chemistry, 2005, Chapter 5, pp. 56-70, vol. 944.
Tsarevsky et al., Well-Defined (Co)polymers with 5-Vinyltetrazole Units via Combination of Atom Transfer Radical (Co)polymerization of Acrylonitrile and "Click Chemistry"—Type Postpolymerization Modification, Macromolecules, 2004, pp. 9308-9313, vol. 37(25).
Udding et al., J. Org. Chem. 59, 1993 (1994).
Van Gaal et al., "Trends in Redox Potentials of Transition Metal Complexes," Coord. Chem. Rev. 1982, 47, 41.
Veregin et al., Macromolecules, 1996, 29, 4161.
Vidts et al., "Design of water-soluble block copolymers containing poly(4-vinylpyridine) by atom transfer radical polymerization", European Polymer Journal, Pergamon Press Ltd, Oxford, GB, vol. 42, No. 1, pp. 43-50 (2006).
Vlcek, "Ligand Based Redox Series," Coord. Chem. Rev. 1982, 43, 39.
Von Werne et al., Preparation of Structurally Well-Defined Polymer—Nanoparticle Hybrids with Controlled/living Radical Polymerizations—J. Am. Chem. Soc. 1999, 121, 7409-7410.
Wang et al., "Living"/Controlled Radical Polymerization, Transition-Metal-Catalyzed Atom Transfer Radical Polymerization in the Presence of a Conventional Radical Initiator, Macromolecules, 1995, pp. 7572-7573, vol. 28.
Wang et al., Controlled/"Living" Radical Polymerization. Atom Transfer Radical Polymerization in the Presence of Transition-Metal Complexes, Journal of the American Chemical Society, 1995, pp. 5614-5615, vol. 117(20).
Wang et al., Controlled/"Living" Radical Polymerization. Halogen Atom Transfer Radical Polymerization Promoted by a Cu(I)/Cu(II) Redox Process, Macromolecules, 1995, pp. 7901-7910, vol. 28(23).
Wang et al., ESR Study and Radical Observation in Transition Metal-Mediated Polymerization: Unified View of Atom Transfer Radical Polymerization Mechanism, in ACS Symposium Series, Advances in Controlled/living Radical Polymerizations, American Chemical Society Division of Polymer Chemistry, 2003, Chapter 12, pp. 161-179, vol. 854.
Wang et al., "Facile Synthesis of Acidic Copolymers Via Atom Transfer Radical Polymerization in Aqueous Media at Ambient Temperature", Macromolecules, ACS, Washington, DC, vol. 33, No. 2, (Jan. 25, 2000), pp. 255-257.
Wang et al., J. Am. Chem. Soc. (1992), 114, 248-255.
Wang et al., Polym. Prep. (Am. Chem. Soc. Polym. Chem. Div.), 36(1), 465 (1995).
Wayland et al., Am. Chem. Soc., 116, 7943 (1994).
Webster, Living Polymerization Methods, Science, 1991, pp. 887-893, vol. 25.
Webster, Makromol. Chem., Macromol. Symp. 67, pp. 365-371 (1993), "Mechanism of GTP: Can all of the Available Data be Accommodated?".
Wei et al., Atom Transfer Radical Polymerization of Styrene in the Presence of Iron Complexes, Polymer Preprints, 1997, pp. 231, vol. 38(2).
Wu et al., Efficiency and Fidelity in a Click-Chemistry Route to Triazole Dendrimers by the Copper(I)-Catalyzed Ligation of Azides and Alkynes, Angewandte Chemie, International Edition, 2004, pp. 3928-3932, vol. 43(30).
Xia et al., Controlled/"Living" Radical Polymerization. Homogenous Reverse Atom Transfer Radical Polymerization Using AIBN as the Initiator, Macromolecules, 1997, pp. 7692-7696, vol. 30.
Xia et al., "Atom Transfer Radical Polymerization of 4-Vinylpyridine", Macromolecules, pp. 3531-3533 (1999).
Zeng et al., "Synthesis and Characterization of Comb-Branched Polyelectrolytes. 1. Preparation of Cationic Macromonomer of 2-(Dimethylamino)ethyl Methacrylate by Atom Transfer Radical Polymerization", Macromolecules, 33(5), pp. 1628-1635 (2000).
Gaynor et al., Macromolecules 1998, 31, 5951-5954.
Chambard et al., Macromol. Symp. 2000, 150, 45-51.
Li et al., Macromolecules 2004, 37, 2106-2112.
Min et al., J. Am. Chem. Soc. 2005, 127, 3825-3830.
Min et al., J. Polym. Sci., Part A: Polym. Chem. 2005, 43, 3616-3622.
Antonietti et al., Macromolecules, 1991, 24: 6636-6643.
Feng et al., "The Preparation of Micropolystyrene Particles by Controlled Microemulsion Polymerization", Polymer Materials Science and Engineering, Jul. 2005, vol. 21, No. 4, 117-120.
Feng, et al., J. Appl. Polym. Sci., 2006, 99 1093-1099.
Min et al., Macromolecules 2005, 38, 8131-8134.
Nicolas et al., Macromolecules 2005, 38, 9963-9973.
Ferguson et al., Macromolecules 2005, 38, 2191-2204.
Gilbert et al., Macromolecular Symposia 2006, 231, 84-93.
Chow et al., Adv. Polym. Sci. 2005, 175, 257-298.
Chow et al., Langmuir 1999, 15, 3202-3205.
El-Safty et al., Chem. Mater. 2005, 17, 3137-3145.
Stoffer et al., J. Polym. Sci. Polym. Chem. Ed. 1980, 18, 2641-2648.
Ferrick et al., Macromolecules 1989, 22, 1515-1517.
Kuo et al., Photoinitiated Polymerization of Styrene in Microemulsions, Macromolecules, 1987, 20, pp. 1216-1221.
Jakubowski et al., Macromolecules 2005, 38, 4139-4146.
Antonietti et al., Macromol. Chem. Phys. 1995, 196, 441-466.
Guo et al., J. Polym. Sci., Part A: Polym. Chem. 1989, 27, 691-710.
Cramer, W. Proc. Chem. Soc. 1914, 30, 293.
Reiner et al., Baskerville Chemical Journal 1953, 4, 15-17.
Singh et al., Zeitschrift fuer Physikalische Chemie (Leipzig) 1957, 207, 198-204.
Parris et al., Discussions of the Faraday Society 1960, 240-247.
Weiss et al., Inorg. Chem. 1964, 3, 1344-1348.
Maeda et al., J. Adv. Polym. Sci. 2006, 193, 103-121.
Brown et al., Nature Rev. Cancer 2004, 4, 437-447.
Khelfallah et al., "Synthesis of New PHEMA/PEO Enzymatically Biodegradable Hydrogel", Macromolecular Rapid Communications, 2006, 27, 1004-1008.
Huang, X and T. L. Lowe, "Biodegradable Thermoresponsive Hydrogels for Aqueous Encapsulation and Controlled Release of Hydrophilic Model Drugs", Biomacromolecules, 2005, 6, 2131-2139.
Houk, J. and G. M. Whitesides, "Structure-Reactivity Relations for Thiol-Disulfide Interchance", J. Am. Chem. Soc., 1987, 109, 6825-6836.
Tsarevsky et al., Chapter VI: Synthesis of Well-Defined Polymeric Materials with Diuslfide and Thiol Groups, Their Further Functionalization, and Reversible Cleavage/Coupling Via Redox Processes: Towards functional (Bio)Degradable Materials, Thesis, Carnegie Mellon University, pp. 249-311 (2005).
Li et al., "Synthesis of Reversible Shell Cross-Linked Micelles for Controlled Release of Bioactive Agents", Macromolecules, 2006, 39, 2726-2728.

(56) References Cited

OTHER PUBLICATIONS

Gao et al., "Synthesis of Degradable Miktoarm Star Sopolymers via Atom Transfer Radical Polymerization", Macromolecules, vol. 38, pp. 5995-6004 (2005).
Schafer et al., Free Radical Biol. Med. 2001, 30, 1191-1212.
Medicinal Research Reviews, 2002, 22, 225-250.
Tsarevsky et al., "Combining Atom Transfer Radical Polymerization and Disulfide/Thiol Redox Chemistry: A Route to Well-Defined (Bio)degradable Polymeric Materials", Macromolecules, 2005, 38, 3087-3092.
Oh et al., "Inverse Miniemulsion ATRP: A New Method for Synthesis and Functionalization of Well-Defined Water-Soluble/Cross-Linked Polymeric Particles", Journal of the American Chemical Society, 2006, 128, 5578-5584.
Oh et al., "Biodegradable Nanogels Prepared by Atom Transfer Radical Polymerization as Potential Drug Delivery Carriers: Synthesis, Biodegradation, in Vitro Release, and Bioconjugation", Journal of the American Chemical Society, 2007, 129 (18): 5939-5945.
Barrett, K.E. et al., J. Polym. Sci., Polym. Chem. Ed. 1969, 7, 2621.
Tseng, C.M. et al., J. Polym. Sci., Part A: Polym. Chem. 1986, 24, 2995.
El-Aasser, M.S. et al., J. Polym. Sci., Part A: Polym. Chem. 1996, 34, 2633.
Kawaguchi et al., Adv. Polym. Sci., 2005, 175, 299.
LaMer, V.K. et al., J. Am. Chem. Soc. 1950, 72, 4847.
Yang, W. et al., J. Polym. Sci., Part A: Polym. Chem. 2001, 39, 555.
Song, J. et al., J. Am. Chem. Soc. 2004, 126, 6562.
Song, J. and M. A. Winnik, "Cross-Linked, Monodisperse, Micro-Sized Polystyrene Particles by Two-Stage Dispersion Polymerization," Macromolecules, vol. 38, pp. 8300-8307 (2005).
Song, J. et al., 2006, 39, 8318-8325.
Hölderle, M. et al., Macromolecules 1997, 30, 3420.
Gabaston et al., Macromolecules 1998, 31, 2883.
Shim, S.E. et al., S. Polymer 2003, 44, 5563.
Min, K. et al., "Development of an ab Initio Emulsion Atom Transfer Radical Polymerization: From Microemulsion to Emulson." J. Am. Chem. Soc. 2006, 128(32), 10521-10526.
Min, K. et al., "Atom Transfer Radical Dispersion Polymerization of Styrene in Ethanol" Polymer Preprints, 2007, 48 (2), 260-261.
Patil et al., Surface-modified and Internally cationic polyamidoamine dendrimers for efficient siRNA delivery, 2008, Bioconjugate Chemistry, vol. 19, pp. 1396-1403.
Zhang, Chi, Transcriptional regulation of bone formation by the osteoblast-specific transcription factor Osz, 2010, Journal of Orthopaedic Surgery and Research, vol. 5:37, pp. 1-8.
Yan et al., Axin2 controls bone remodeling through the beta-catenin-BMP signaling pathway in adult mice, 2009, Journal of Cell Science, vol. 122, pp. 3566-3578.
Akhtar et al., "Toxicogenomics of non-viral drug delivery systems for RNAi: Potential impact on siRNA-mediated gene silencing activity and specificity", Adv. Drug Delivery Rev., 2007, 59, (2-3), 164-182.
Bencherif et al., "End-group effects on the properties of PEG-co-PGA hydrogels", Acta Biomater, 2009, 5(6): 1872-1883.
Bencherif et al., "Influence of cross-linker chemistry on release kinetics of PEG-co-PGA hydrogels", J. Biomed. Mater. Res., Part A, 2009, 90A(1): 142-153.
Bencherif et al., "Cell-Adhesive Star Polymers Prepared by ATRP", Biomacromolecules, 2009, (10), 1795-1803.
Bencherif et al., "Influence of the degree of methacrylation on hyaluronic acid hydrogels properties", Biomaterials, 2008, 29, (12), 1739-1749.
Bencherif et al., "Nanostructured hybrid hydrogels prepared by a combination of atom transfer radical polymerization and free radical polymerization", Biomaterials, 2009, 30, (29), 5270-5278.
Bencherif et al., "Synthesis by AGET ATRP of Degradable Nanogel Precursors for In Situ Formation of Nanostructured Hyaluronic Acid Hydrogel", Biomacromolecules, 2009, 10, (9), 2499-2507.

Birukova et al., "ALK5 and Smad4 are involved in TGF-beta1-induced pulmonary endothelial permeability", FEBS Letters, 2005, 579(18): 4031-4037.
Bober et al., "Delivery of siRNA using cationic star polymers to suppress runt related transcription factor 2 and osterix in vitro", 34th Annual Meeting of the Society for Biomaterials 2010, Giving Life to a World of Materials, Seattle, Washington, USA, Apr. 21-24, 2010, vol. 2 of 2, 579.
Braunecker, W. A. and K. Matyjaszewski, "Controlled/living radical polymerization: Features, developments, and perspectives". [Erratum to document cited in CA147:486671], Progress in Polymer Science, 2008, 33, (1), 165.
Braunecker, W. and K. Matyjaszewski, "Controlled/living radical polymerization: Features, developments, and perspectives", Progress in Polymer Science, 2007, 32, (1), 93-146.
Brekke, J. H., and Kipling Thacker, "Hyaluronan as a Biomaterial", An Introduction to Biomaterials, The Biomedical Engineering Series, 2006, 219-240.
Chaturvedi, et al., "Noggin maintains pluripotency of human embryonic stem cells grown on Matrigel", Cell Prolif, Aug. 2009, 42, (4), 425-433.
Cho et al., "Synthesis of Biocompatible PEG-Based Star Polymers with Cationic and Degradable Core for siRNA Delivery", Biomacromolecules: 12(10): 3478-3486.
Cho et al., "Preparation of Poly(ethylene glycol) Star Copolymers with a Cationic Core for siRNA Delivery by ATRP", Polym. Prepr., (Am. Chem. Soc., Div. Polym. Chem.), 2011, 52(2): 608-609.
Cho et al., "Rapid Cellular Internalization of Multifunctional Star Polymers Prepared by Atom Transfer Radical Polymerization", Biomacromolecules, 2010, 11 (9): 2199-2203.
Coessens et al., "Functional polymers by atom transfer radical polymerization", Progress in Polymer Science, 2001, 26, (3), 337-377.
Colla et al., "Human myeloma cells express the bone regulating gene Runx2/Cbfa1 and produce osteopontin that is involved in angiogenesis in multiple myeloma patients", Leukemia, 2005, 19, (12), 2166-2176.
Demetriou, et al., "Fetuin/alpha2-HS glycoprotein is a transforming growth factor-beta type II receptor mimic and cytokine antagonist", J Biol Chem, 1996, 271, (22), 12755-12761.
Dong, Hongchen and Krzysztof Matyjaszewski, "ARGET ATRP of 2-(Dimethylamino)ethyl Methacrylate as an Intrinsic Reducing Agent", Macromolecules, 2008, 41, 6868-6870.
Duncan et al., "Dendrimer biocompatibility and toxicity", Adv. Drug Delivery Rev., 2005, 57, (15), 2215-2237.
Duncan et al., "Polymer therapeutics: polymers as drugs, drug and protein conjugates and gene delivery systems: past, present and future opportunities", Adv. Polym. Sci., 2006, 192, (Polymer Therapeutics I), 1-8.
El-Aneed, A., "An overview of current delivery systems in cancer gene therapy", J. Controlled Release, 2004, 94, (1), 1-14.
Fukuda et al., Generation of a mouse with conditionally activated signaling through the BMP receptor, ALK2, Genesis, 2006, 44, (4), 159-167.
Gao, H. and K. Matyjaszewski, "Synthesis of functional polymers with controlled architecture by CRP of monomers in the presence of cross-linkers: From stars to gels", Prog. Polym. Sci., 2009, 34, (4), 317-350.
Gilmore et al., "The design and exogenous delivery of siRNA for post-transcriptional gene silencing", Journal of Drug Targeting, 2004, 12, (6), 315-340.
Goldring, M. B. and S. R. Goldring, "Skeletal tissue response to cytokines", Clin Orthop Relat Res, 1990, (258), 245-278.
Guimaraes, M. and P. Mourao, "Urinary excretion of sulfated polysaccharides administered to Wistar rats suggests a renal permselectivity to these polymers based on molecular size", Biochim. Biophys. Acta, Gen. Subj., 1997, 1335, (1-2), 161-172.
Gupta et al., "Hydrogels: from controlled release to pH-responsive drug delivery", Drug Discov Today, 2002, 7, (10), 569-579.
Hammond, et al., "An RNA-directed nuclease mediates post-transcriptional gene silencing in *Drosophila* cells", Nature, 2000, 404, (6775), 293-296.

(56) References Cited

OTHER PUBLICATIONS

Hartwell, R. et al., "A Novel Nydrogel-Collagen Composite Improves Functionality of an Injectable Extracellular Matrix", Acta Biomaterialia, 7, 2011, 3060-3069.
Hawker et al., "New polymer synthesis by nitroxide mediated living radical polymerizations", Chem Rev, 2001, 101, (12), 3661-3688.
Heath et al., "Charged polymers via controlled radical polymerization and their implications for gene delivery", Macromol. Chem. Phys., 2007, 208, (12), 1243-1249.
Heggli et al., "Michael-type addition as a tool for surface functionalization", Bioconjugate Chem., 2003, 14, (5), 967-973.
Heldin et al, "TGF-beta signalling from cell membrane to nucleus through SMAD proteins", Nature, 1997, 390, (6659), 465-471.
Hiemstra et al., "Rapidly in situ-forming degradable hydrogels from dextran thiols through michael addition", Biomacromolecules, 2007, 8, (5), 1548-1556.
Hong et al., "TAZ, a transcriptional modulator of mesenchymal stem cell differentiation", Science, 2005, 309, (5737), 1074-1078.
Hong, et al., "Post-transcriptional gene silencing using siRNA delivered from star nanostructured polymer", Abstracts/Bone, 46, S9-S83, accepted for society for Biomaterials, Seattle, WA, Apr. 2124, 2010, S49-S50.
Ikeda et al., "The promyelotic leukemia zinc finger promotes osteoblastic differentiation of human mesenchymal stem cells as an upstream regulator of CBFA1", J. Biol. Chem., 2005, 280(9): 8523-8530.
Ikeda et al., "Identification of FAZF as a novel BMP2-induced transcription factor during osteoblastic differentiation", J Cell Biochem, 2007, 101, (1), 147-154.
Iorio, R. et al., "Heterotopic ossification after hip and knee arthroplasty: risk factors, prevention, and treatment", J Am Acad Orthop Surg, 2002, 10, (6), 409-416.
Jazag et al., "Single small-interfering RNA expression vector for silencing multiple transforming growth factor-beta pathway components", Nucleic Acids Research, 2005, 33(15): e131, 1-9.
Kim et al., "Inhibition of ocular angiogenesis by siRNA targeting vascular endothelial growth factor pathway genes: therapeutic strategy for herpetic stromal keratitis", Am J Pathol, 2004, 165, (6), 2177-2185.
Li et al., "A New Class of Biochemically Degradable, Stilumus-Responsive Triblock Copolymer Gelators", Agnew. Chem. Int. Ed., 2006, 45, 3510-3513.
Lowe, A. and C. McCormick, "Reversible addition-fragmentation chain transfer (RAFT) radical polymerization and the synthesis of water-soluble (co)polymers under homogeneous conditions in organic and aqueous media", Prog. Polym. Sci., 2007, 32, (3), 283-351.
Ma et al., "Structural basis for overhang-specific small interfering RNA recognition by the PAZ domain", Nature (London, U. K.), 2004, 429, (6989), 318-322.
Matyjaszewski et al., "Simple and Efficient Synthesis of Various Alkoxyamines for Stable Free Radical Polymerization", Macromolecules, 1998, 31, (17), 5955-5957.
McCarthy, E.F. and M. Sundaram, "Heterotopic ossification: a review", Skeletal Radiol, 2005, 34: 609-619.
Merkel et al., "Stability of siRNA polyplexes from poly(ethylenimine) and poly(ethylenimine)-g-poly(ethylene glycol) under in vivo conditions: Effects on pharmacokinetics and biodistribution measured by Fluorescence Fluctuation Spectroscopy and Single Photon Emission Computed Tomography (SPECT) imaging", J. Controlled Release, 2009, 138, (2), 148-159.
Murakami et al., "A WW domain protein TAZ is a critical coactivator for TBX5, a transcription factor implicated in Holt-Oram syndrome", PNAS, USA, 2005, 102(50): 18034-18039.
Naik et al., "Gene delivery to the retina: focus on non-viral approaches", Drug Discovery Today, 2009, 14, (5/6), 306-315.
Nakao et al. "Identification of Smad7, a TGFβ-inducible antagonist of TGF-β signalling", Nature, vol. 389, Oct. 9, 1997, 631-635.
Oh et al., "Synthesis and Biodegradation of Nanogels as Delivery Carriers for Carbohydrate Drugs", Biomacromolecules, 2007, 8, (11), 3326-3331.

Oh et al., "The development of microgels/nanogels for drug delivery applications", Progress in Polymer Science, 2008, 33, (4), 448-477.
Ohyama et al., "Spaciotemporal association and bone morphogenetic protein regulation of sclerostin and osterix expression during embryonic osteogenesis", Endocrinology, 2004, 145, (10), 4685-4692.
Park et al., "Photo-Cross-Linkable Thermoresponsive Star Polymers Designed for Control of Cell-Surface Interactions", Biomacromolecules, 2010, 11(10): 2647-2652.
Parkinson et al., "Radiation therapy in the prevention of heterotopic ossification after total hip arthroplasty", Hip, 1982, 211-227.
Reddi, et al., "Biochemical sequences in the transformation of normal fibroblasts in adolescent rats", Proc Natl Acad Sci USA, 1972, 69, (6), 1601-5.
Saina et al., "BMPs and chordin regulate patterning of the directive axis in a sea anemone", Proc Natl Acad Sci USA, 2009, 106, (44), 18592-18597.
Shen, Y., "Advances in the development of siRNA-based therapeutics for cancer", IDrugs, 2008, 11(8): 572-578.
Shore et al., "A recurrent mutation in the BMP type I receptor ACVR1 causes inherited and sporadic fibrodysplasia ossificans progressiva", Nature Genetics, 2006, 38, (5), 525-527.
Shore et al., "Insights from a rare genetic disorder of extra-skeletal bone formation, fibrodysplasia ossificans progressiva (FOP)", Bone, 2008, 43, (3), 427-433.
Sieber et al., "Recent advances in BMP receptor signaling", Cytokine Growth Factor Rev, 2009, 20, (5-6), 343-355.
Siegwart et al., "Solvent induced morphologies of poly(methyl methacrylate-b-ethylene oxide-b-methyl methacrylate) triblock copolymers synthesized by atom transfer radical polymerization," Polymer, 2007, 48(25): 7279-7290.
Siegwart et al., "Biotin-, Pyrene-, and GRGDS-functionalized polymers and nanogels via ATRP and end group modification", Macromol. Chem. Phys., 2008, 209, (21), 2179-2193.
Siegwart et al., "Cellular uptake of functional nanogels prepared by inverse miniemulsion ATRP with encapsulated proteins, carbohydratesmand gold nanoparticles, Biomacromolecules", 2009, 10, (8), 2300-2309.
Siegwart et al., "Synthesis, characterization, and in vitro cell culture viability of degradable poly(N-isopropylacrylamide-co-5,6-benzo-2- methylene-1,3-dioxepane)-based polymers and crosslinked gels", Journal of Biomedical Materials Research, Part A, 2008, 87 A, (2), 345-358.
Srinivasan et al., "Delivery of siRNA Using Cationic Nanostructured Star Polymers to Prevent Myoblast Cell Differentiation to Bone", Carnegie Mellon University, Pittsburgh, Pennsylvania, Dec. 2010, 1 page.
Thomas et al., "Progress and problems with the use of viral vectors for gene therapy", Nat. Rev. Genet., 2003, 4, (5), 346-358.
Turner et al., "RNA targeting with peptide conjugates of oligonucleotides, siRNA and PNA", Blood Cells Mol Dis, 2007, 38, (1), 1-7.
Urist, M. R., "The search for and discovery of bone morphogenetic protein (BMP)," Bone Grafts, Derivatives and Substitutes, Butterworth: London, 1994, 315-362.
van Ooij et al., "Surgical removal of debilitating neurogenic heterotopic ossifications of the hip". Ned Tijdschr Geneeskd, 2005, 149, (1), 37-41. English abstract.
Vanden Bossche, L. and G. Vanderstraeten, "Heterotopic ossification: a review", J Rehabil Med, 2005, 37, (3), 129-136.
Wang et al., "Delivery of siRNA Therapeutics: Barriers and Carriers", The AAPS Journal, 2010, 12(4): 492-503.
Wang et al., "p53 functions as a negative regulator of osteoblastogenesis, osteoblast-dependent osteoclastogenesis, and bone remodeling", J Cell Biol, 2006, 172(1): 115-125.
Wordinger et al., "Focus on molecules: gremlin", Exp Eye Res, 2008, 87, (2), 78-79.
Xia et al., "Repulsive guidance molecule RGMa alters utilization of bone morphogenetic protein (BMP) type II receptors by BMP2 and BMP4", J Biol Chem, 2007, 282(25): 18129-18140.
Yagi et al., "Bcl-2 positively regulates Sox9-dependent chondrocyte gene expression by suppressing the MEK-ERK1/2 signaling pathway", J Biol Chem, 2005, 280, (34), 30517-30525.

(56) References Cited

OTHER PUBLICATIONS

Yan et al., "Regulation of TGF-beta signaling by Smad7", Acta Biochim Biophys Sin (Shanghai), 2009, 41, (4), 263-272.
Yu et al., "BMP type I receptor inhibition reduces heterotopic [corrected] ossification", Nat Med, 2008, 14, (12), 1363-1369.
Zelikin et al., "Disulfide Cross-Linked Polymer Capsules: En Route to Biodeconstructible Systems", Biomacromolecules, 2006, 7, 27-30.
Zhang, et al., "The bone morphogenetic protein signaling pathway is upregulated in a mouse model of total parenteral nutrition", J Nutr, 2009, 139, (7), 1315-1321.
Pyun et al., "Synthesis of Well-Defined Block Copolymers Tethered to Polysilsequioxane Nanoparticles and their Nanoscale Morphology on Surfaces", J. Am. Chem. Soc. 123, 9445-9446 (2001).
Pyun et al., Supporting Information, J. Am. Chem. Soc., 51-58 (2001).
Pyun et al., "Synthesis of Nancomposite Organic/Inorganic Hybrid Materials Using Controlled/'Living' Radical Polymerization," Chem. Mater. 13, 3436-3448 (2001).
Pyun et al., "Synthesis of Polymer Brushes Using Atom Transfer Radical Polymerization", Macromol. Rapid Commun. 24, 1043-1059 (2003).
Pyun et al., "Synthesis and Characterization of Organic/Inorganic Hybrid Nanoparticles: Kinetics of Surface-Initiated Atom Transfer Radical Polymerization and Morphology of Hybrid Nanoparticle Ultrathin Films", Macromolecules 36, 5094-5104 (2003).
Matyjaszewski et al., Chapter 17 Organic-Inorganic Hybrid Polymers from Atom Transfer Radical Polymerization and Poly(dimethylsiloxane), Am. Chemical Soc. Symposia. 270-283 (2000).
Pyun et al. "Organic/Inorganic Hybrid Materials from Polysiloxanes and Polysilsesquioxanes Using Controlled/Living Radical Polymerization", Manuscript submitted for Publication 1-12 (2007).
Bombalski et al., "Quasi-transparent Hybrid Particles Using Atom Transfer Radical Polymerization", Polymeric Materials: Science & Engineering 97, 327 (2007).
Bockstaller et al., "Block Copolymer Nanocomposites: Perspectives for Tailored Functional Materials", Adv. Mater. 17, 1331-1349 (2005).
Bombalski et al., "Null-Scattering Hybrid Particles Using Controlled Radical Polymerization", Adv. Mater. 19, 4486-4490 (2007).
Bouvier-Fontes et al., "Seeded Semicontinuous Emulsion Copolymerization of Butyl Acrylate with Cross-Linkers", Macromolecules 38, 1164-1171 (2005).
Kirsch et al., "Control of Particle Morphology and Film Structures of Carboxylated Poly(Methyl Methacrylate)/Poly(n-Butylacrylate) Composite Latex Particles", Journal of Appliled Polymer Science, vol. 91, 2610-2623 (2004).
Kirsch et al., "Control of Particle Morphology and Film Structures of Carboxylated Poly(N-Butylacrylate)/Poly(methyl) Composite Latex Particles", Colloids and Surfaces, A Physicochemical and Engineering Aspects, 183-185, 725-737 (2001).
Garnett, "Colours in Metal Glasses and in Metallic Films", Phil. Trans. R. Soc. Lond. A. 203, 385-420 (1904).
Garnett, "Colours in Metal Glasses, in Metallic Films, and in Metal Solutions II", Phil. Trans. R. Soc. Lond. A. 205, 237-288 (1906).
Baysal, et al., Styrene Polymerization with a Macroinitiator Having Siloxane Units, Journal of Applied Polymer Science, May 31, 1996, vol. 60, 1369-1378.
Gaynor et al., "Synthesis of Branched and Hyperbranched Polystyrenes", Macromolecules, 1996, 29, 1079-1081.
Ando et al., "Living Radical Polymerization of Methyl Methacrylate with Ruthenium Complex: Formation of Polymers with Controlled Molecular Weights and Very Narrow Distributions", Macromolecules, 1996, 29, 1070-1072.
Ishizu et al., "Synthesis of star polymers by organized polymerization of macromonomers", *Polymer*, vol. 36, pp. 4155-4157 (1995).
Mirica et al., "Structure and Spectroscopy of Copper-Dioxygen Complexes", Chem. Rev. 2004, 104, 1013-1045.

Bouix et al., "Synthesis of amphiphilic polyelectrolyte block copolymers using "living" radical polymerization, Application as stabilizers in emulsion polymerization", Macromol. Rapid Commun., 1998, 19, 209-213.
Burguiere et al., "Amphiphilic Block Copolymers Prepared via Controlled Radical Polymerization as Surfactants for Emulsion Polymerization", Macromol. Symp. 2000, 150, 39-44.
Nicolay et al., "Dibromotrithiocarbonate Iniferter for Concurrent ATRP and RAFT Polymerization. Effect of Monomer, Catalyst, and Chain Transfer Agent Structure on the Polymerization Mechanism," Macromolecules, 2008, 41, 4585-4596.
Nicolay et al., "Synthesis of poly(vinyl acetate) block copolymers by successive RAFT and ATRP with a bromoxanthate iniferter," Chem. Commun., 2008, 5336-5338.
Kwak, et al., "Effect of Initiator and Ligand Structures on ATRP of Styrene and Methyl Metacrylate Initiated by Alkyl Dithiocarbamate," Macromolecules, 2008, 41, 6627-6635.
Kwak, et al., "Concurrent ATRP/RAFT of Strene and Methyl Methacrylate with Dithioesters Catalyzed by Copper(I) Complexes," Macromolecules, 2008, 41, 6602-6604.
Wager et al., "A simple method to convert atom transfer radical polymerization (ATRP) Initiators into reversible addition fragmentation chain-transfer (RAFT) mediators." Eur. Polym. J., 2004, 40, 641-645.
Kabachii, et al., "Dithioesters in Atom-Transfer Radical Polymerization," Polym. Sci, Ser. B, 2006, 48, 32-36.
Zhang, et al., "Atom Transfer Radical Polymerizations of Methyl Methacrylate and Styrene with an Iniferter Reagent as the Initiator," J. Appl. Polym. Sci., 2007, 106, 230-237.
Zhang, et al., "Synthesis of Well-Defined Naphthalene and Photolabile Group-Labeled Polystyrene via ATRP," J. Polym. Sci.: Part A: Polym. Chem., 2006, 44, 510-518.
Kwak, et al., "Photoirradiated Atom Transfer Radical Polymerization with an Alkyl Dithiocarbamate at Ambient Tempterature", Macromolecules, 2010, 43, 5180-5183.
Matsuzaki et al., "Stereoregularity of Polystyrene and Mechanism of Polymerization", Die Makromolekulare Chemie, 1975, 176, 3051-3064.
Haddleton et al., "Identifying the Nature of the Active Species in the Polymerization of Methacrylates: Inhibition of Methyl Methacrylate Homopolymerizations and Reactivity Ratios for Copolymerization of Methyl Methacrylate/n-Butyl Methacrylate in Classical Anionic, Alkyllithium/Trialkylaluminum-Initiated, Group Transfer Polymerization, Atom Transfer Radical Polymerization, Catalytic Chain Transfer, and Classical Free Radical Polymerization", Macromolecules, 1997, 30, 3992-3998.
Webster, Owen W., "Group Transfer Polymerization: Mechanism and Comparison with Other Methods for Controlled Polymerization of Acrylic Monomers", Adv Polym Sci, 2004, 167, 1-34.
Azari et al., "Bone morphogenetic proteins: A review for cranial and maxillofacial surgery," Oral and Maxillo. Surg. Clin. of N.A., 14:1-14, 2002.
Jadlowiec et al., "Bone tissue engineering: recent advances and promising therapeutic agents," Expert Opin. Biol. Ther, 3(3):409-423, 2003.
Kübler et al., "Effect of different factors on the bone forming properties of recombinant BMPs," Mund Kiefer GesichtsChir, 2000; 4(8):465-469 (Abstract).
Zilliox et al., "Preparation of star-shaped macromolecules by anionic copolymerization," Journal of Polymer Science, Polymer Symposia, No. 22 (Pt. 1): 145-56, (1968).
Kanaoka et a., "Synthesis of star-shaped poly-vinyl ethers by living cationic polymerization: pathway for formation of star-shaped polymers via polymer linking reactions," Polymer Bulletin (Berlin) 44(5-6): 485-492, (2000).
Shibata, et al., "Quantitative Synthesis of Star-Shaped Poly(vinyl ether)s with a Narrow Molecular Weight Disribution by Living Cationic Polymerization," Journal of the American Chemical Society, 128(23): 7497-7504, (2006).
Qiu et al., "Controlled/Living Radical Polymerization in Aqueous Media: Homogeneous and Heterogeneous Systems," *Prog. Polym. Sci.*, vol. 26, pp. 2083-2134 (2001).

(56) References Cited

OTHER PUBLICATIONS

Ohno, S. and K. Matyjaszewski, "Controlling Grafting Density and Side Chain Length in Poly(n-butyl acrylate) by ATRP (Co)polymerization of Macromonomers," Journal of Polymer Chem. Ed., 2006, 44, 5454-5467 (2006).
Matyjaszewski, K. and J. Xia, "Fundamentals of Atom Transfer Radical Polymerization," Handbook of Radical Polymerization, Chapter 11; John Wiley & Sons, Inc., pp. 523-628 (2002).
Kamigaito et al., Chem. Rev., 101, 3689 (2001).
Gao, H. and K. Matyjaszewski, "Low Polydispersity Star Polymers with Core Functionality by Cross-linking Macromonomers Using Functional ATRP Intiators," Macromolecules, 40, 399-401 (2007).
Gao et al., J. Am. Chem. Soc., Low Polydispersity Star Polymers via Cross-linking Macromonomers by ATRP, 128, 15111-15113 (2006).
Davis, K. A. and K. Matyjaszewski, "Statistical, Gradient, Block, and Graft Copolymers by Controlled/Living Radical Polymerizations," Adv. Polym. Sci., vol. 159 pp. 1-168 (2002).
Furukawa, T. and K. Ishizu, Journal of Colloid and Interface Science, 253(2), 465-469, (2002).
Matyjaszewski, K.,"Comparison and Classification of Controlled/ Living Radical Polymerizations," American Chemical Society, publication date: Aug. 15, 2000, pp. 2-26, downloaded on Sep. 2, 2009, http://pubs.acs.org.
Le Droumaguet, B. and K. Velonia, "In Situ ATRP-Mediated Hierarchical Formation of Giant Amphiphile Bionanoreactors", Angew. Chem. Int. Ed., 2008, 47(33), pp. 6263-6266.
Tsarevsky et al., "Factors Determining the Performance of Copper-Based Atom Transfer Radical Polymerization Catalysts and Criteria for Rational Catalyst Selection", ACS Symposium Series, 2006, 944, pp. 56-70.
Duncan, R. and M. Vicent, "Do HPMA copolymer conjugates have a future as clinically useful nanomedicines? A critical overview of current status and fututre opportunities", Advanced Drug Delivery Reviews, 62, 2010, pp. 272-282.
Enoki et al., "Acid Denaturation and Refolding of Green Fluorescent Protein", Biochemistry, 2004, 43, pp. 14238-14248.
Arakawa et al., "Protein precipitation and denaturation by dimethyl sulfoxide", Biophysical Chemistry, 131, 2007, pp. 62-70.
Li et al., "Thermoresponsive Block Copolymer-Protein Conjugates Prepared by Grafting-from via RAFT Polymerization", Macromol. Rapid Commun., 2011, 32, pp. 354-359.
Li et al., "Thermoresponsive Block Copolymer-Protein Conjugates Prepared by Grafting-from via RAFT Polymerization" Supporting Information for Macromol. Rapid Commun., 2011, 32, pp. 354-359.
Lele et al., "Synthesis of Uniform Protein—Polymer Conjugates", Biomacromolecules, 2005, 6, pp. 3380-3389.
Peschke et al., "C-Terminally PEGylated hGH-derivatives", Bioorganic & Medicinal Chemistry, 15, 2007, pp. 4382-4395.
De Paoli et al., "New insights into the mechanism of activation of atom transfer radical polymerization by Cu(I) complexes", Chem. Commun., 2011, 47, pp. 3580-3582.
Pintauer et al., "Atom Transfer radical addition and polymerization reactions catalyzed by ppm amounts of copper complexes", Chem. Soc. Rev., 2008, 37, pp. 1087-1097.
Grover, G. and H. Maynard, "Protein-polymer conjugates: synthetic approaches by controlled radical polymerizations and interesting applications", Current Opinion in Chemical Biology, 2010, 14(6), pp. 818-827.
Peeler et al., "Genetically Encoded Initiator for Polymer Growth from Proteins", JACS Communications, 2010, 132, pp. 13575-13577.
Tang et al., "Understanding atom Transfer Radical Polymerization: Effect of Ligan and Initiator Structures on the Equilibrium Constants", J. Am. Chem. Soc., 2008, 130, pp. 10702-10713.
Bontempo, D. and H. Maynard, "Streptavidin as a Macroinitiator for Polymerization: In Situ Protein-Polymer Conjugate Formation", J. Am. Chem. Soc., 2005, 127, pp. 6508-6509.
Bontempo et al., "Cysteine-Reactive Polymers Synthesized by Atom Transfer Radical Polymerization for Conjugation to Proteins", J. Am. Chem. Soc., 2004, 126, pp. 15372-15373.

Abuchowski et al., "Alteration of Immunological Properties of Bovine Serum Albumin by Covalent Attachment of Polyethylene Glycol", The Journal of Biological Chemistry, 1977, 252, pp. 3578-3581.
Abuchowski et al., "Effect of Covalent Attachment of Polyethylene Glycol on Immunogenicity and Circulating Life of Bovine Liver Catalase", The Journal of Biological Chemistry, 1977, 252, pp. 3582-3586.
Duncan, Ruth, "The Dawning Era of Polymer Therapeutics", Nature Reviews, Drug Discovery, 2003, 2, pp. 347-360.
Tsarevsky et al., "Deactivation Efficiency and Degree of Control over Polymerization in ATRP in Protic Solvents", Macromolecules, 2004, 37, pp. 9768-9778.
Lutz et al., "Biocompatible, Thermoresponsive, and Biodegradable: Simple Preparation of "All-in-One" Biorelevant Polymers," Macromolecules, 2007, 40, pp. 8540-8543.
Braunecker et al., "Thermodynamic Components of the Atom Transfer Radical Polymerization Equilibrium: Quantifying Solvent Effects", Macromolecules, 2009, 42, pp. 6348-6360.
Bortolamei et al., "Thermodynamic Properties of Copper Complexes Used as Catalysts in Atom Transfer Radical Polymerization", Macromolecules, 2010, 43, pp. 9257-9267.
Al-Abboodi et al., "Three-Dimensional Nanocharacterization of Porous Hydrogel With Ion and Electron Beams", Biotechnology and Bioengineering, vol. 110, No. 1, Jan. 2013, pp. 318-326.
Mathur et al., "Methods for Synthesis of Hydrogel Networks: A Review", 1996, Journal of Macromolecular Science, Part C, 36:2, pp. 405-430.
Dimitrov et al., "Continuous Convective Assembling of Fine Particles into Two-Dimensional Arrays on Solid Surfaces", Langmuir, 1996, 12, pp. 1303-1311.
Salerno et al. "Pore Structure and Swelling Behavior of Porous Hydrogels Prepared via a Thermal Reverse-Casting Technique", Journal of Applied Polymer Science, 2011, vol. 122, pp. 3651-3660.
Simakova et al., "Aqueous ARGET ATRP", Macromolecules, 2012, 45, pp. 6371-6379.
Stein et al., "Morphological Control in Colloidal Crystal Templating of Inverse Opals, Hierarchical Structures, and Shaped Particles", Chem. Mater. 2008, 20, pp. 649-666.
Stein et al., "Colloidal crystal templating of three-dimensionally ordered macroporous solids: materials for photonics and beyond", Current Opinion in Solid State and Materials Science, 5 (2001) pp. 553-564.
Gates et al., "Fabrication and Characterization of Porous Membranes with Highly Ordered Three-Dimensional Periodic Structures", Chem. Mater., 1999, 11, pp. 2827-2836.
Lange et al., "Functional 3D photonic films from polymer beads", phys. stat. sol. (a) 204, No. 11, 2007, pp. 3618-3635.
Shu et al., "Rational Design of Affinity Ligand for the Oriented Immobilization of Trypsin", Acta Phys. Chim. Sin., 2013, 29 (2), pp. 439-448.
Hwang et al., "Fabrication of three-dimensional porous cell-laden hydrogel for tissue engineering", Biofabrication 2 (2010) 12 pages.
Chen et al., "Macroporous Hydrogel Scaffolds and Their Characterization by Optical Coherence Tomography", Tissue Engineering: Part C vol. 17, No. 1, 2011, pp. 101-112.
Seliktar, Dror, "Designing Cell-Compatible Hydrogels for Biomedical Applications", Science, 336, (2012), pp. 1124-1128.
Behravesh et al., "Evaluation of the in Vitro Degradation of Macroporous Hydrogels Using Gravimetry, Confined Compression Testing, and Microcomputed Tomography", Biomacromolecules, 2002, 3, 1263-1270.
Li et al., "Colloidal Assembly: The Road from Particles to Colloidal Molecules and Crystals", Angew. Chem. Int. Ed. 2011, 50, pp. 360-388.
Marlow et al., "Opals: Status and Prospects", Angew. Chem. Int. Ed. 2009, 48, pp. 6212-6233.
Meseguer et al., "Synthesis of inverse opals", Colloids and Surfaces A: Physicochemical and Engineering Aspects, 202 (2002) pp. 281-290.
Xu et al., "Facile Trypsin Immobilization in Polymeric Membranes for Rapid, Efficient Protein Digestion", Anal. Chem., 2010, 82, pp. 10045-10051.

(56) References Cited

OTHER PUBLICATIONS

Xu et al., "Facile Trypsin Immobilization in Polymeric Membranes for Rapid, Efficient Protein Digestion", Anal. Chem., 2010, 82, 10045-10051, Supporting Information, 17 pages.
Fudouzi et al., "Photonic Papers and Inks: Color Writing with Colorless Materials", Adv. Mater., 2003, 15, No. 11, pp. 892-896.
Hustoft et al., "A Critical Review of Trypsin Digestion for LC-MS Based Proteomics", Integrative Proteomics, http://www.intechopen.com/books/integrative-proteomics/a-critical-review-of-trypsin-digestion-for-lc-ms-basedproteomics, 2012, pp. 73-92.
Oxley et al., "Macroporous hydrogels for biomedical applications: methodology and morphology", Biomaterials, 1993, vol. 14, No. 14, pp. 1064-1072.
Savina, Irina, "Macroporous hydrogels by cryogelation: biomedical and environmental applications", abstract, School of Pharmacy and Biomolecular Sciences, University of Brighton, 2012, 1 page.
Savina et al., "Biomimetic Macroporous Hydrogels: Protein Ligand Distribution and Cell Response to the Ligand Architecture in the Scaffold", Journal of Biomaterials Science, 20 (2009) pp. 1781-1795.
Shepard et al., "Hydrogel macroporosity and the prolongation of transgene expression and the enhancement of angiogenesis", Biomaterials, 33 (2012) pp. 7412-7421.
Duan et al., "Versatile fabrication of arbitrarily shaped multi-membrane hydrogels suitable for biomedical applications", J. Mater. Chem. B, 2013, 1, pp. 485-492.
Kopeček, Jindřich, "Hydrogel biomaterials: A smart future?", Biomaterials, 28, 2007, pp. 5185-5192.
Lee et al., "Recent Progress in the Synthesis of Porous Carbon Materials", Adv. Mater. 2006, 18, pp. 2073-2094.
Ma et al., "Organic-Inorganic Hybrid Silica Monolith Based Immobilized Trypsin Reactor with High Enzymatic Activity", Anal. Chem., 2008, 80, pp. 2949-2956.
Ma et al., "Monolith-based immobilized enzyme reactors: Recent developments and applications for proteome analysis", J. Sep. Sci., 2007, 30, pp. 3050-3059.
Zhu et al., "Crystallization of hard-sphere colloids inmicrogravity", Nature, vol. 387, Jun. 26, 1997, pp. 883-885.
Pal et al., "Polymeric Hydrogels: Characterization and Biomedical Applications—A mini review", Designed Monomers and Polymers, 12, 2009, pp. 197-220.
Liu et al., "Hydrogels from Biopolymer Hybrid for Biomedical, Food, and Functional Food Applications"; Polymers, 2012, 4, pp. 997-1011.
Woodcock, L.V., "Entropy difference between the face-centered cubic and hexagonal close-packed crystal structures", Nature, vol. 385, Jan. 9, 1997, pp. 141-143.
Dainiak et al., "Biomimetic Macroporous Hydrogel Scaffolds in a High-Throughput Screening Format for Cell-Based Assays", Biotechnol. Prog., 2008, 24, pp. 1373-1383.
Ford et al., "A macroporous hydrogel for the coculture of neural progenitor and endothelial cells to form functional vascular networks in vivo", PNAS, Feb. 21, 2006, vol. 103, No. 8, pp. 2512-2517.
Holgado et al., "Electrophoretic Deposition to Control Artificial Opal Growth", Langmuir, 1999, 15, pp. 4701-4704.
Kato et al., "Monolithic Bioreactor Immobilizing Trypsin for High-Throughput Analysis", Anal. Chem., 2005, 77, pp. 1813-1818.
Peppas et al., "Hydrogels in pharmaceutical formulations", European Journal of Pharmaceutics and Biopharmaceutics, 50, 2000, pp. 27-46.
Annabi et al., "Controlling the Porosity and Microarchitecture of Hydrogels for Tissue Engineering", Tissue Engineering: Part B, vol. 16, No. 4, 2010, pp. 371-383.
Davis et al., "Modular enzymatically crosslinked protein polymer hydrogels for in situ gelation", Biomaterials, 31, 2010, pp. 7288-7297.
Dziomkina et al., "Colloidal crystal assembly on topologically patterned templates", Soft Matter, 2005, 1, pp. 265-279.

Velev et al., "Structured Porous Materials via Colloidal Crystal Templating: From Inorganic Oxides to Metals", Adv. Mater., 2000, 12, No. 7, pp. 531-534.
Velev et al., "Colloidal crystals as templates for porous materials", Current Opinion in Colloid & Interface Science 5, 2000, pp. 56-63.
Jiang et al., "Single-Crystal Colloidal Multilayers of Controlled Thickness", Chem. Mater. 1999, 11, pp. 2132-2140.
Jiang et al., "Template-Directed Preparation of Macroporous Polymers with Oriented and Crystalline Arrays of Voids", J. Am. Chem. Soc., 1999, 121, pp. 11630-11637.
Schroden et al., "Hybrid macroporous materials for heavy metal ion adsorption", J. Mater. Chem., 2002, 12, pp. 3261-3267.
Pusey et al., "Structure of Crystals of Hard Colloidal Spheres", Physical Review Letters, Dec. 18, 1989, vol. 63, No. 25, pp. 2753-2756.
Zhao et al., "Horseradish Peroxidase Immobilized in Macroporous Hydrogel for Acrylamide Polymerization", Journal of Polymer Science: Part A: Polymer Chemistry, 2008, vol. 46, pp. 2222-2232.
Pernites et al., "Patterned Surfaces Combining Polymer Brushes and Conducting Polymer via Colloidal Template Electropolymerization", Adv. Mater., 2011, 23, pp. 1287-1292.
Schroden et al., "Optical Properties of Inverse Opal Photonic Crystals", Chem. Mater., 2002, 14, pp. 3305-3315.
Johnson et al., "Ordered Mesoporous Polymers of Tunable Pore Size from Colloidal Silica Templates", Science, vol. 283, Feb. 12, 1999, pp. 963-965.
Owen et al., "Design of three-dimensional biomimetic scaffolds", Journal of Biomedical Materials Research A, Sep. 15, 2010, vol. 94A, Issue 4, pp. 1321-1331.
Park et al., "Crystallization of Mesoscale Particles over Large Areas", Adv. Mater., 1998, 10, No. 13., pp. 1028-1032.
Park et al., "Macroporous Membranes with Highly Ordered and Three-Dimensionally Interconnected Spherical Pores", Adv. Mater. 1998, 10, No. 13, pp. 1045-1048.
Park et al., "Fabrication of Three-Dimensional Macroporous Membranes with Assemblies of Microspheres as Templates", Chem. Mater., 1998, 10, pp. 1745-1747.
Park et al., "Assembly of Mesoscale Particles over Large Areas and its Application in Fabricating Tunable Optical Filters", Langmuir, 1999, 15, pp. 266-273.
Ronel et al., "Macroporous hydrogel membranes for a hybrid artificial pancreas. I. Synthesis and chamber fabrication", Journal of Biomedical Materials Research, vol. 17, 1983, pp. 855-864.
Hollister, Scott J., "Porous scaffold design for tissue engineering", Nature Materials, vol. 4, Jul. 2005, 518-524.
Gulrez et al., "Hydrogels: Methods of Preparation, Characterisation and Applications", Progress in Molecular and Environmental Bioengineering—From Analysis and Modeling to Technology Applications, Aug. 2011, pp. 117-150.
Keskar et al., "In Vitro Evaluation of Macroporous Hydrogels to Facilitate Stem Cell Infiltration, Growth, and Mineralization", Tissue Engineering, Part A vol. 15, No. 7, 2009, pp. 1695-1707.
Wu et al., "Design and Preparation of Porous Polymers", Chem. Rev., 2012, 112, pp. 3959-4015.
Wu et al., "A novel organic-inorganic hybrid monolith for trypsin immobilization", Sci China Life Sci, Jan. 2011, vol. 54, No. 1, pp. 54-59.
Zhao et al., "Templating methods for preparation of porous structures", J. Mater. Chem., 2006, 16, pp. 637-648.
Zhang et al., "Gaseous infiltration method for preparation of three-dimensionally ordered macroporous polyethylene", Polymer, 49, 2008, pp. 5446-5451.
Zhang et al., "Inverted-Colloidal-Crystal Hydrohel Matrices as Three-Dimensional Cell Scaffolds", Adv. Funct. Mater., 2005, 15, No. 5, pp. 725-731.
Chung-li et al., "Studies on the preparation and characterisation of monodisperse polystyrene latices", Progr. Colloid & Polymer Sci., 60, 1976, pp. 163-175.
Huang et al., "A novel immobilized cobalt(II)/copper(II) bimetallic catalyst for atom transfer radical polymerization (ATRP) of methyl methacrylate", Applied Catalysis A: General, vol. 332, Issue 2, Nov. 20, 2007, pp. 192-199.

(56) References Cited

OTHER PUBLICATIONS

Nasser-Eddine et al., "Copper removal in atom transfer polymerization through electrodeposition", Macromol. Mater. Eng., 2004, 289, pp. 204-207.
Coullerez et al., "Understanding Copper-Based Atom-Transfer Radical Polymerization in Aqueous Media", The Journal of Physical Chemistry A, Sep. 2, 2004, vol. 108, No. 35, pp. 7129-7131.
Hong et al., "An Immobilized/Soluble Hybrid Catalyst System for Atom Transfer Radical Polymerization", Macromolecules, 2001, vol. 34, No. 15, pp. 5099-5102.
Matyjaszewski, Krzysztof, "Mechanistic Aspects of Atom Transfer Radical Polymerization", ACS Symp. Ser., 1998, Chapter 16, 685, pp. 258-283.
Matyjaszewski, Krzysztof, "Bulk Atom Transfer Radical Polymerization", ACS Symp. Ser., 1998, Chapter 6, 713, pp. 96-112.
Matyjaszewski et al. "The Preparation of Wel-Defined Water Soluble-Swellable (Co)Polymers by Atom Transfer Radical Polymerization", ACS Symp. Ser., 2000, Chapter 4, 765, pp. 52-71.
Matyjaszewski, Krzysztof, "Controlled Radical Polymerization: State of the Art in 2008", ACS Symp. Ser., 2009, Chapter 1, 1023, pp. 3-13.
Konkolewicz et al, "Tuning Polymer Properties through Competitive Processes", ACS Symp. Ser. 2012, 1100, pp. 145-170.
Hansch et al., "A Survey of Hammett Substituent Constants and Resonance and Field Parameters", Chem. Rev. 1991, 91, pp. 165-195.
Tsarevsky et al., ""Green" Atom Transfer Radical Polymerization: From Process Design to Preparation of Well-Defined Environmentally Friendly Polymeric Materials", Chem. Rev. 2007, 107, pp. 2270-2299.
Xia et al., "Controlled/"Living" Radical Polymerization Atom Transfer Radical Polymerization of Acrylates at Ambient Temperature", Macromolecules, 1998, 31, pp. 5958-5959.
Xia et al., "Controlled/"Living" Radical Polymerization. Atom Transfer Radical Polymerization Catalyzed by Copper(I) and Picolylamine Complexes", Macromolecules, 1999, 32, pp. 2434-2437.
Braunecker et al., "Origin of Activity in Cu-, Ru-, and Os-Mediated Radical Polymerization", Macromolecules, 2007, 40, pp. 8576-8585.
Seeliger et al., "Temperature Effect on Activation Rate Constants in ATRP: New Mechanistic Insights into the Activation Process", Macromolecules, 2009, 42, pp. 6050-6055.
Magenau et al. "ATRP of Methacrylates Utilizing Cu"X2/L and Copper Wire, Macromolecules, 2010, 43, pp. 9682-9689.
Kwak et al., "ARGET ATRP of Methyl Acrylate with Inexpensive Ligands and ppm Concentrations of Catalyst", Macromolecules, 2011, 44, pp. 811-819.
Zhang et al., "Copper-Mediated CRP of Methyl Acrylate in the Presence of Metallic Copper: Effect of Ligand Structure on Reaction Kinetics", Macromolecules, 2012, 45, pp. 78-86.
Morick et al., "Activation—Deactivation Equilibrium of Atom Transfer Radical Polymerization of Styrene up to High Pressure", Macromol. Chem. Phys., 2011, 212, pp. 2423-2428.
di Lena et al., "Transition metal catalysts for controlled radical polymerization", Progress in Polymer Science, 35, 2010, pp. 959-1021.
Pintauer et al., "Atom Transfer Radical Polymerization (ATRP) and Addition (ATRA) and Applications", Encyclopedia of Radicals in Chemistry, Biology and Materials, 2012, 4, 1851-1894.
Malkov et al., "Synthesis of New Chiral 2,2'-Bipyridyl-Type Ligands, Their Coordination to Molybdenum(0), Copper(II), and Palladium(II), and Application in Asymmetric Allylic Substitution, Allylic Oxidation, and Cyclopropanation", Organometallics, 2001, 20, pp. 673-690.
Montalti et al., "Luminescent Ruthenium(II) Bipyridyl-Phosphonic Acid Complexes: pH Dependent Photophysical Behavior and Quenching with Divalent Metal Ions", Inorg. Chem., 2000, 39, pp. 76-84.
Nitadori et al., "Enhanced Photocatalytic Activity of α-Methylstyrene Oligomerization through Effective Metal-to-Ligand Charge-Transfer Localization on the Bridging Ligand", Inorg. Chem., 2012, 51, pp. 51-62.
Pintauer et al., "Structural aspects of copper catalyzed atom transfer radical polymerization", Coordination Chemistry Reviews, 249, 2005, pp. 1155-1184.
Ding et al., "Atom Transfer Radical Polymerization of N,N-Dimethylacrylamide", Macromol. Rapid Commun., 2004, 25, pp. 632-636.
Kickelbick et al., "Structural comparison of Cu complexes in atom transfer radical polymerization", New J. Chem, 2002, 26, pp. 462-468.
Magenau et al., "Highly Active Bipyridine-Based Ligands for Atom Transfer Radical Polymerization", ACS Macro Lett., 2012, 1, pp. 508-512.
Schröder et al., "Substituted Tris(2-pyridylmethyl)amine Ligands for Highly Active ATRP Catalysts", ACS Macro Lett., 2012, 1, 1037-1040.
Abreu et al., "Inorganic Sulfites: Efficient Reducing Agents and Supplemental Activators for Atom Transfer Radical Polymerization", ACS Macro Lett., 2012, 1, pp. 1308-1311.
Eckenhoff et al., "Structural characterization and investigation of iron(III) complexes with nitrogen and phosphorus based ligands in atom transfer radical addition (ATRA)", Inorganica Chimica Acta, 382, 2012, pp. 84-95.
Matyjaszewski et al., "Diminishing catalyst concentration in atom transfer radical polymerization with reducing agents", PNAS, Oct. 17, 2006, vol. 103, No. 42, pp. 15309-15314.
Jakubowski et al. "Activators Regenerated by Electron Transfer for Atom-Transfer Radical Polymerization of (Meth)acrylates and Related Block Copolymers", Angew. Chem., 2006, 118, pp. 4594-4598.
Yasuda, et al., "Stereospecific Polymerization of Acetaldehyde by $R_2AlOR'$ Catalyst," Journal of Polymer Science, vol. 11, 1973, pp. 1421-1434.
Poli, et al., "Iron-mediated reversible deactivation controlled radical polymerization," Progress in Polymer Science 39 (2014), pp. 1827-1845.
Saikia, et al., "Reverse Atom Transfer Radical Polymerization of Stearyl Methacrylate Using 2,2'-Azobisisobutyronitrile as the Initiator,"Journal of Applied Polymer Science, vol. 85 (2002), pp. 1236-1245.
Stoffelbach et al., "Half-sandwich molybdenum(iii) compounds containing diazadiene ligands and their use in the controlled radical polymerization of styrene." Journal of Organometallic Chemistry 663 (2002) 269-276, (2002), p. 270, col. 2.
Park, Sangwoo, et al., "Simplified Electrochemically Mediated Atom Transfer Radical Polymerization using a Sacrificial Anode," Angew. Chem. Int. Ed, 2015, 54, pp. 2388-2392.
Park, Sangwoo, et al., "Star Synthesis Using Macroinitiators via Electrochemically Mediated Atom Transfer Radical Polymerization," Macromolecules, 2013, 46, pp. 5856-5860.
Samal, Seetanshu K., et al., "Electroinitiated Polymerization of Acrylamide in Acetonitrile Medium," Journal of Polymer Science: Part A: Polymer Chemistry, vol. 26, 1988, pp. 1035-1049.
Magenau, Andrew J., et al., "Investigation of Electrochemically Mediated Atom Transfer Radical Polymerization," Macromolecules, 2013, 46, pp. 4346- 4353.
Chmielarz, Pawel, et al., "PEO-b-PNIPAM copolymers via SARA ATRP and eATRP in Aqueous Media," Polymer, 71, 2015, pp. 143-147.
Bonometti, Valentina, et al., "Exploring the first steps of an electrochemically-triggered controlled polymerization sequence: Activation of alkyl- and benzyl halide initiators by an electrogenerated $Fe^{II}$ Salen complex," Journal of Electroanalytical Chemistry 633 (2009) pp. 99-105.
Bortolamei, Nicola, et al., "Controlled Aqueous Atom Transfer Radical Polymerization with Electrochemical Generation of the Active Catalyst," Angew. Chem. Int. Ed., 2011, 50, pp. 11391-11394.
Magenau, Andrew J., et al., "Electrochemically Mediated Atom Transfer Radical Polymerization," Science, vol. 332, Apr. 1, 2011, pp. 81-84.

(56) References Cited

OTHER PUBLICATIONS

Fischer, Hanns, et al., "The Persistent Radical Effect in "Living" Radical Polymerization," Macromolecules 1997, 30, pp. 5666-5672.
Haddleton, David M., et al., "Atom Transfer Polymerization of Poly(Ethylene Glycol) Methyl Ether Methacrylate Macromonomer," Polymer Preprints, 2000, 41(1), pp. 415-416.
Abreu C. M. R. et. al.; Polymer Chemistry 2013, 4, 5629-5636.
Alsubaie, F. et. al.; Polym. Chem. 2015 6, 406-417.
Anastasaki, A.; et. al.; Macromol Rapid Comm 2014, 35 (10), 965-970.
C. Andrieux et. al., J. Electroanal. Chem. 1978, 87, 39-53.
C. Andrieux et. al., J. Electroanal. Chem. 1978, 87, 55-65.
C. Andrieux et. al., J. Electroanal. Chem. 1980, 113, 19-40.
Bell C. A. et. al.; "A Rapid Electrochemical Method for Determining Rate Coefficients for Copper-Catalyzed Polymerizations," J. Am. Chem. Soc., 2011, 133 11944-47.
Buback, M. et. al.; "Pressure dependence of propagation rate coefficients in freeradical homopolymerizations of methyl acrylate and dodecyl acrylate," Macromol. Chem. Phys. 1998, 199, 1721-1727.
Buback, M. et. al.; "Termination Kinetics of Methyl Acrylate and Dodecyl Acrylate Free-Radical Homopolymerizations up to High Pressure," Macromol. Chem. Phys. 2002, 203, pp. 1065-1070.
Fischer H. et al., "Factors Controlling the Addition of Carbon-Centered Radicals to Alkenes—An Experimental and Theoretical Perspective," Angew. Chem. Int. Ed. 2001, 40, 1340-1371.
Golub G. et.al.; "The effect of N-methylation of tetra-aza-alkane copper complexes on the axial binding of anions," Inorg. Chim. Acta 1997, 255, 111-115.
Harrisson, S.; et al., "Comproportionation versus Disproportionation in the Initiation Step of Cu(0)-Mediated Living Radical Polymerization," Macromolecules 2012, 45, 7388-7396.
Henderson, et al., "Ionic Effects on the Behavior of Thermoresponsive PEO-PNIPAAm Block Copolymers," J Polym Sci Polym. Phys 2014, 52 (7), 507-516.
Kim K. H.; et al.; "Preparation of hydrogel nanoparticles by atom transfer radical polymerization of N-isopropylacrylamide in aqueous media using PEG macro-initiator," Polymer 2005, 46 (9), 2836-2840.
Konkolewicz, D.; et al.; "Aqueous RDRP in the Presence of $Cu^0$: The Exceptional Activity of $Cu^I$ Confirms the SARA ATRP Mechanism," Macromolecules 2014, 47 (2), 560-570.
Konkolewicz, D.; et. al.; "Visible Light and Sunlight Photoinduced ATRP with ppm of Cu Catalyst," ACS Macro Lett. 2012, 1, 1219-1223.
Konkolewicz, D.; et. al.; "ICAR ATRP with ppm Cu Catalyst in Water," Macromolecules 2012, 45, 4461-4468.
Millard, et al.; "Controlling the Fast ARTP of N-Isopropylacrylamide in Water," ACS Symposium Series 2009, 1023, 127-137.
Matyjaszewski, K.; "Atom Transfer Radical Polymerization (ATRP): Current Status and Future Perspectives," Macromolecules. 2012, 45 (10), 4015-4039.
Miyake et. al., "Perylene as an Organic Photocatalyst for the Radical Polymerization of Functionalized Vinyl Monomers through Oxidative Quenching with Alkyl Bromides and Visible Light," Macromolecules 2014, 47, 8255-8261.
Nguyen. et. al.; The Effect of Ligand on the Rate of Propagation of Cu(0)-Wire Catalyzed SET-LRP of MA in DMSO at 25° C., Polym. Sci., Part A: Polym. Chem. 2009, 47, 5629-5638.
Nguyen. et. al.; "SET-LRP of N,N-Dimethylacrylamide and of N-Isopropylacrylamide at 25° C. in Protic and in Dipolar Aprotic Solvents," J Polym Sci Polym. Chem 2010, 48 (8), 1752-1763.
Nicholson R. S., "Theory and Application of Cyclic Voltammetry for Measurement of Electrode Reaction Kinetics," Anal. Chem. 1965, vol. 37, 1351-1355.
Onsager, L., "Reciprocal Relations in Irreversible Processes," Phys. Rev. 1931, vol. 37, 405-426.

Peng, C-H.; et al.; "Reversible-Deactivation Radical Polymerization in the Presence of Metallic Copper. Activation of Alkyl Halides by $Cu^0$," Macromolecules 2013, 46, 3803-3815.
Percec, et al.; "Ultrafast Synthesis of Ultrahigh Molar Mass Polymers by Metal-Catalyzed Living Radical Polymerization of Acrylates, Methacrylates, and Vinyl Chloride Mediated by SET at 25° C.," J. Am. Chem. Soc. 2006, 128, 14156-14165.
Treat, Nicolas J., et. al., "Metal-Free Atom Transfer Radical Polymerization," J. Am. Chem. Soc. 2014, 136, 16096-16101.
Waldron C et al.; "Absolut "copper catalyzation perfected"; robust living polymerization of NIPAM: Guinness is good for SET-LRP," Polym. Chem. 2014, 5(1): 57-61.
Wang, Yu et. al.; "Reversible-Deactivation Radical Polymerization in the Presence of Metallic Copper. Comproportionation—Disproportionation Equilibria and Kinetics," Macromolecules 2013, 46, 3793-3802.
Wei H. et al.; "One-pot ATRP synthesis of a triple hydrophilic block copolymer with dual LCSTs and its thermo-induced association behavior," Soft Matter 2012, 8 (37), 9526-9528.
Wever, et. al., "Polymers for enhanced oil recovery: A paradigm for structure-property relationship in aqueous solution," Prog. Polym. Sci. 2011, 36 (11), 1558-1628.
Williams, et. al., "A Silver Bullet: Elemental Silver as an Efficient Reducing Agent for Atom Transfer Radical Polymerization of Acrylates," J. Am. Chem. Soc. 2015, 137, 1428-1431.
Zhang,et al., "Copper-mediated controlled radical polymerization under biological conditions: SET-LRP in blood serum," Chem. Commun. 2013, 49, 6608-6610.
Zhang, et al. "Aqueous Copper-Mediated Living Polymerization: Exploiting Rapid Disproportionation of CuBr with $Me_6TREN$," J. Am. Chem. Soc. 2013, 135, 7355-7363.
Zhong, et. al., "Reversible-Deactivation Radical Polymerization in the Presence of Metallic Copper. Kinetic Simulation," Macromolecules, 2013, 46, 3816-3827.
Averick, et al., "ATRP under Biologically Relevant Conditions: Grafting from a Protein," ACS Macro Lett. 2012, 1, 6-10.
*The chemistry of free radical polymerization;* 2nd Ed. ed.; Elsevier: Amsterdam, 2006 (book not attached).
He, et al., "Three-Dimensionally Ordered Macroporous PolymericnMaterials by Colloidal Crystal Templating for Reversible C02 Capture." Advanced Functional Materials 23(37): 4720-4728, Oct. 2013.
Pal, et al., "Preparation and Characterization of Polyvinyl Alcohol-Gelatin Hydrogel Membranes for Biomedical Applications," AAPS PharmSciTech 2007;8(1): Article 21; E1-E5.
Davis, et al., "Disorder-to-Order Transition in Settling Suspensions of Colloidal Silica: X-ray Measurements," Science 1989, vol. 245, 507-510.
Zhao, et al., Templating Methods for Preparation of Porous Structures, J. Materials Chemistry, 2006;16: 637-648.
Xia, et al., "Monodispersed Colloidal Spheres: Old Materials with New Applications," Adv. Mater. 2000; 12(10): 693-713.
Yue, et al., "Preparation and Characterization of Nanostructured and High Transparent Hydrogel Films with pH Sensitivity and Application," Journal of Applied Polymer Science 2009;112(4):2261-2269.
Hearnden, et al., "New developments and opportunities in oral mucosal drug delivery for local and systemic disease," Advanced Drug Delivery Reviews 2012; 64: 18-23.
Hongkun He, et al., "Multifunctional Hydrogels with Reversible 3D Ordered Macroporous Structures," Advanced Science, 2015, 2, pp. 1-6.
Hongkun He, et al., "Multifunctional Hydrogels with Reversible 3D Ordered Macroporous Structures," Supporting Information for Advanced Science, 2015, 2, pp. S1-S37 (38 pages).
Coca, S., et al., "Block Copolymers by Transformation of "Living" Carbocationic into "Living" Radical Polymerization. II. ABA-Type Block Copolymers Comprising Rubbery Polyisobutene Middle Segment," J. Polym. Sci., Part A: Polym. Chem. 1997, 35, 3595-3601.
Coca S., et al., "Block Copolymers by Transformation of "Living" Carbocationic into "Living" Radical Polymerization," American Chemical Society, Macromolecules, vol. 30, No. 9,1997, pp. 2808-2810.

(56) References Cited

OTHER PUBLICATIONS

Matyjaszewski, K., Y. Nakagawa, et al. (1998). "Polymerization of n-butyl acrylate by atom transfer radical polymerization. Remarkable effect of ethylene carbonate and other solvents." Macromolecules 31(5): 1535-1541.

Coca S., et al., "Block Copolymers by Transformation of Living Carbocationic into Living Radical Polymerization," Polymer Preprints, American Chemical Society, Macromolecules, vol. 38, No. 1, 1997, pp. 693-694.

Zapata-Gonzalez, "Mathematical Modeling of the Full Molecular Weight Distribution in ATRP Techniques," AIChE Journal, vol. 62, No. 8, Aug. 2016, pp. 2762-2777.

\* cited by examiner

ATOM TRANSFER RADICAL POLYMERIZATION UNDER BIOLOGICALLY COMPATIBLE CONDITIONS

CROSS REFERENCE TO RELATED APPLICATIONS

This application is a continuation application claiming priority, under 35 U.S.C. § 120, to U.S. patent application Ser. No. 14/239,181, filed Jun. 4, 2014, which application is a U.S. National Stage application, filed under 35 U.S.C. § 371, of International patent application No. PCT/US2012/051855, filed on Aug. 22, 2012, which application claims the benefit under 35 U.S.C § 119(e) of U.S. Provisional Application 61/575,482 filed on Aug. 22, 2011 and U.S. Provisional Application 61/690,688 filed on Jul. 2, 2012, the disclosures of each of which are entirely incorporated herein by this reference as if fully set forth herein.

STATEMENT REGARDING FEDERALLY SPONSORED RESEARCH

This invention was made with government support under DMR0969301 awarded by the National Science Foundation. The government has certain right in the invention.

TECHNICAL FIELD

The present invention defines conditions that allow conducting a controlled grafting from atom transfer radical polymerization (ATRP) reaction in aqueous media under biologically compatible conditions. Biologically compatible conditions are conditions under which proteins or other bio-responsive molecules do not denature, or undergo any conformational or chemical change that modifies their activity. Aqueous based systems, low catalyst concentrations and ambient temperatures are desired.

BACKGROUND

Protein-Polymer Conjugates (PPCs) have been described as a marriage between two diverse yet symbiotic materials. PPCs combine the biological specificity of proteins with the diverse functions and tunable properties of synthetic polymers. Proteins and other biologically active molecules are used in a number of diagnostic, monitoring or treatment applications by virtue of their biological activity and specificity. However the in vivo delivery of such agents can encounter several limitations including low solubility, poor stability, short half lives and a potential to create an immunogenic response which may require frequent administration of the agent or generate a risk of adverse reactions. The conjugation of proteins with well defined polymers allows the resulting PPC to overcome some of the inherent limitations of specific proteins targeting specific biological applications.

When one takes into consideration the rate at which reversible-deactivation radical polymerization (RDRP), formerly named controlled radical polymerization (CRP) procedures that include Nitroxide Mediated Polymerization (NMP), Atom Transfer Radical Polymerization (ATRP), and Reversible Addition Fragmentation Transfer (RAFT) have evolved over the last two decades, to provide access to (co)polymers with predefined molecular weights, compositions, architectures and narrow/controlled molecular weight distributions, it is no surprise that a growing number of researchers have decided to combine the biological specificity of proteins and other biologically active (macro) molecules, including peptides, nucleic acids, and carbohydrates, with the diverse functions and tunable properties of synthetic polymers prepared by RDRP by conjugation to form well-defined polymer protein hybrids (PPH); a procedure frequently termed bioconjugation. [*Curr. Opin. Chem. Biol.*, 2010. 14(6): 818-827] Functionalization of bioresponsive molecules with well defined polymers can provide improved stability, tailored solubility, predeterminable trafficking pathways, and increased therapeutic potential of already useful biomacromolecules including peptides, proteins, nucleic acids, and polysaccharides in a variety of applications.

Indeed, since RDRP processes can provide compositionally homogeneous well-defined polymers, with predicted molecular weight, narrow molecular weight distribution, and high degrees of α- and ω-end-functionalization, they have been the subject of much study as reported in several review articles and ACS symposia. [Matyjaszewski, K., Ed. Controlled Radical Polymerization; ACS: Washington, D.C., 1998; ACS Symposium Series 685. Matyjaszewski, K., Ed.; Controlled/Living Radical Polymerization. Progress in ATRP, NMP, and RAFT; ACS: Washington, D.C., 2000; ACS Symposium Series 768; Matyjaszewski, K., Davis, T. P., Eds. Handbook of Radical Polymerization; Wiley: Hoboken, 2002; Qiu, J.; Charleux, B.; Matyjaszewski, K. *Prog. Polym. Sci.* 2001, 26, 2083; Davis, K. A.; Matyjaszewski, K. *Adv. Polym. Sci.* 2002, 159, 1.]

Matyjaszewski and coworkers disclosed the fundamental four component ATRP process comprising the addition, or in situ formation, of an initiator, in this case a molecule with a transferable atom or group that is completely incorporated into the final product, a transition metal and a ligand that form, a partially soluble transition metal complex that participates in a reversible redox reaction with the added initiator or a dormant polymer to form the active species to copolymerize radically polymerizable monomers, and a number of improvements to the basic ATRP process, in a number of commonly assigned patents and patent applications: U.S. Pat. Nos. 5,763,546; 5,807,937; 5,789,487; 5,945,491; 6,111,022; 6,121,371; 6,124,411; 6,162,882; 6,624,262; 6,407,187; 6,512,060; 6,538,091; 6,541,580; 6,624,262; 6,627,314; 6,759,491; 6,790,919; 6,887,962; 7,019,082; 7,049,373; 7,064,166; 7,125,938; 7,157,530; 7,332,550; 7,407,995; 7,572,874; 7,678,869; 7,795,355; 7,825,199; 7,893,173; 7,893,174; U.S. Ser. Nos. 12/877,589; 12/949,466; and International patent applications PCT/US04/09905; PCT/US06/33152; PCT/US06/048656; PCT/US08/64710; PCT/US09/36377; PCT/US2010/029073; PCT/US2011/051043 and PCT/US11/65578 all of which are herein incorporated by reference to provide background and definitions for the present disclosure.

The generally accepted mechanism of an ATRP reaction is shown in Scheme 1.

Scheme 1. General mechanism for the ATRP process

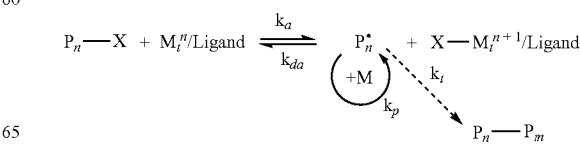

ATRP is the most efficient RDRP method for the preparation of pure segmented copolymers, since, unlike RAFT, it does not require addition of a radical initiator to continuously form new polymer chains that do not contain the desired α-biofunctional group in a grafting from reaction and unlike NMP does not require high temperatures to generate the active species by homolytic cleavage of the dormant chain end. ATRP allows the synthesis of new telechelic multi-segmented copolymers with a predetermined degree of polymerization, low molecular weight distribution ($M_w/M_n$, also called polydispersity index or PDI), incorporating a wide range of functional monomers and displaying controllable macromolecular structures under mild reaction conditions. ATRP generally requires addition or formation of an alkyl halide or (pseudo)halide as an initiator (R—X) or dormant polymer chain end ($P_n$—X), and a partially soluble transition metal complex (Cu, Fe or Ru, for example) capable of undergoing a redox reaction as a catalyst. This procedure would be expected to be ideal for the preparation of PPCs but surprisingly, considering the prior efforts in this field there have been problems preparing well defined bioconjugate materials.

As noted above PPCs have a relatively long history of being used therapeutically because they exhibit the properties of both the biomolecules and the polymer, with the polymer actively providing a means to tune the bioactivity of the biomolecule or passively stabilizing the biomolecules in vivo to allow an increase in blood circulation time or improved tumor targeting by enhanced permeation and retention effects. The primary applications of PPCs have been developed by the pharmaceutical industry, where they are used as highly potent therapeutics. PPCs have also been applied to prepare biological sensing devices. The first generation of PPCs were described in 1977 by Abuchowski et al. [*J. Biol Chem.* 1977, 252, 3578 & 3582] The authors reported that proteins modified with poly(ethylene glycol) (PEG) have a greatly increased in vivo circulation time and reduced immunogenicity, and this started an extended study of PEG based bioconjugation because PEG and its derivatives are nontoxic, non-immunogenic, and possess biocompatible properties.

Recently there has been considerable interest dedicated to alternative methods of "PEGylation" by the polymerization of PEG or oligo(ethylene glycol) (OEG) vinyl-macromonomers. Many of these methods allow the preparation of polymers that are both biocompatible and stimuli-responsive. Increasingly, polymer bioconjugates with therapeutic potential are being made with synthetic polymers other than PEG based copolymers. This work has given rise to an expanding research field where stimuli responsive polymers are conjugated to bioresponsive molecules [*Nat. Rev. Drug Discovery* 2003, 2, 347; *Bioorg. Med. Chem.* 2007, 15, 4382; *J. Am. Chem. Soc.* 2010, 132, 13575]. Similar to PEG, these polymers may also enhance the stability and solubility of the biological component to which they are attached, while simultaneously providing responsive behavior and numerous sites for subsequent functionalization; e.g., to allow the attachment of cofactors, targeting ligands, imaging reagents, etc. The synergistic effect of polymer bioconjugation can be further enhanced by the introduction of functional groups into the polymer's backbone. New drug delivery systems can be envisioned where hydrophobic drugs are encapsulated into a PPC above the polymers lower critical solution temperature (LCST) and released in vivo in a predetermined area at a predeterminable rate.

Two methods are generally used for the preparation of PPCs: the "grafting to" approach, which involves conjugation of a preformed polymer to a protein, and the "grafting from" approach, which involves growing a polymer from a known initiator site within the protein.

"Grafting to" has been used to conjugate a variety of polymers to proteins including poly(ethylene glycol), thermo-responsive polymers, drug-loaded polymers, and dye-loaded polymers among others. Indeed due to the ongoing development of bio-orthogonal "click chemistry" methods [*Angew. Chem. Int. Ed.,* 2001. 40(11): 2004]. Bioconjugation has furthermore become increasingly selective, which has led to hybrid structures with improved functional characteristics. While RDRP techniques have allowed synthesis of precisely defined PPCs with properties unachievable through simple PEGylation and the procedure allows for the straightforward formation of, and subsequent conjugation of, polymers to proteins, under high yield conditions "grafting to" has several limitations. Typically PPC's prepared by "grafting to" suffer from substantial batch-to-batch variability and generate a broad distribution of products. This variability is due to the presence of a multiplicity of reactive groups on the surface of a targeted protein in addition to steric constraints generated when grafting two large macromolecules together. Furthermore, purification of the desired PPC from a multitudinous mixture of modified proteins and free polymer is challenging.

The alternative approach to synthesizing PPC's is the "grafting from" method. In this method an initiating group is immobilized onto a protein, typically through acetylation of lysine or cysteine residues present within the protein, and a polymer is grown from the incorporated initiator/control agent in situ. The major advantages of protein polymer conjugates formed by "grafting from" procedures are high yields and avoidance of traditional purification issues associated with the "grafting to" method. The field of using controlled radical procedures for a "grafting from" has been slowly gaining popularity as a standard tool to creating functional PPC's.

In the first example of this method, a biotinylated ATRP initiator was bound to streptavidin and PNIPAM or POEOMA chains were grown from the streptavidin tetra initiator [*J. Am. Chem. Soc.* 2005, 127, 6508; U.S. Pat. No. 7,786,213 B2]. In a later work, POEOMA was grown from the C-terminus of green fluorescent protein (GFP) and shown to accumulate in vivo in a tumor mouse model [*Proc. Natl. Acad. Sci.* 2010. 107(38): 16432-7; and PCT Publication WO 2010/096422]. More recently, an engineered non-natural amino acid bearing an ATRP initiating site was genetically incorporated into the 134 amino acid residue of GFP [*J. Am. Chem. Soc.* 2010, 132, 13575] and POEOMA was grown from this genetically encoded initiator. The retention of the fluorescence demonstrated preservation of the GFP's native tertiary structure during the RDRP. This initial work on preparation of a protein-polymer conjugate (PPC) based on a RDRP, specifically a "grafting from" ATRP, provided a composite structure with a stable link between the protein and the copolymer was disclosed in U.S. Provisional Application 61/381,757 filed on Sep. 10, 2010, converted to PCT/US2011/051043, which is hereby incorporated by reference.

However, achieving a high degree of control over the "grafting from" processes has proven to be challenging. Typically the gel permeation chromatography (GPC) curves of the formed PPC do not display a normal distribution of molecular weights and provide high values for molecular weight distribution ($M_w/M_n$). The curves observed in size exclusion chromatography display a substantial tailing to low the molecular weight region, which would indicate low and/or poor initiation efficiencies. As noted in the PCT/US2011/051043 application, specifically in the discussion relating to FIG. 7C of the '043 application, reproduced herein as FIG. 1, there is a tailing towards low $M_n$ region of the GPC elutogram of the product formed during the grafting from reaction, compare the dark line for parent GFP with the grey line from the product. This extended tailing indicates the formation of non-uniform protein-polymer conjugates that could have negative implications for controlled therapeutic protein delivery and uniform enzymatic processes. This is not a unique observation since a similar problem is seen in other published GPC traces from PPCs formed by "grafting from" reactions; FIG. 10 in U.S. Pat. No. 7,786,213 and FIGS. 10, 13 and 26 in PCT application WO 2010/096422 and, indeed in any prior art work conducted under previously envisioned bio-compatible conditions.

Therefore one of the remaining challenges present when seeking to incorporate a protein, or other biologically responsive molecule, into a well defined protein-polymer conjugate in a "grafting from" reaction is to identify, define, and exemplify conditions for the "grafting from" reaction that provides uniform well defined tethered chain(s). A target for the degree of dispersity of the tethered copolymer chain that is accepted as indicative of good control in a RDRP grafting from reaction is a $M_w/M_n$ of less than 1.30, preferably less than 1.25 and more preferably less than 1.20. In addition the reaction should not affect the properties of the biologically responsive molecule; thereby providing a bioconjugate in which uniform (co)polymer segment(s) are attached to the protein, or other biologically responsive molecule, at known sites within the bioresponsive molecule that do not modify the physiological action of the protein or other biologically responsive molecule in an undesired fashion, or reduce the effectiveness of the desired bioresponsive action to any significant degree.

To summarize the current state of the art focusing on "grafting from" proteins has resulted in a situation where reaction conditions utilized for the "grafting from" reaction are copied from conditions employed for a biologically inactive initiator, frequently a small molecule. The conditions are taken from the literature then applied to a new bio-sensitive macroinitiator. This means that a wide range of polymerization conditions have been used to prepare PPCs including a variety of different monomer and protein-initiator concentrations, catalyst to initiator ratios, catalyst systems, i.e. ligands and copper halides, copper(I) to copper(II) ratios, and solvent systems; essentially procedures where reagents are mixed with a protein initiator and the reaction is stopped after a seemingly random time frame. Despite claims for a successful grafting from protein polymers conjugates produced by these procedures have long tail towards low molecular weights and there has been little description of the rate of the polymerization with respect to conversion or time [*J. Am. Chem. Soc.* 2005, 127(18), 6508-6509; *Biomacromolecules* 2005, 6(6), 3380-3387; *Angew. Chem. Int. Ed.* 2008, 47(33), 6263-6266; *Proc. Natl. Acad. Sci. USA* 2009, 106(36), 15231-6; *Proc Natl Acad Sci USA* 2010, 107(38), 16432-7; *Adv. Drug Deliv. Rev.,* 2010. 62(2): 272-82].

Other RDRP techniques have also been examined, on the basis that ATRP requires a high concentration of an undesireable metal catalyst, include RAFT [*Macromol Rapid Commun.* 2011, 32, 354] and NMP [*Polym. Chem.,* 2011. 2(7): 1523-1530]. These procedures also possess inherent limitations when targeting well defined PPCs. In the case of RAFT a secondary source of radicals is required to drive the reaction thereby forming non-conjugated polymer contaminants. NMP requires a high temperature to form the active propagating radical which can denature the bio-active agent. In common with prior art ATRP procedures the products of both procedures displayed a broad dispersity; $M_w/M_n = \leq 1.40$ and $M_w/M_n = \leq 1.33$ respectively.

In order for a "grafting from" procedure to become a widely utilized method in the preparation of PPCs the aforementioned challenges must be addressed and conditions that lead to direct preparation of a well defined PPC must be established. Preparation of these materials under biologically compatible conditions would allow synthesis of biomaterials in their native environments and minimize post fabrication purification steps while preserving biological activity.

SUMMARY OF THE INVENTION

The present disclosure describes embodiments for conducting a controlled radical polymerization process under biologically compatible conditions, for example to produce conjugates between bioresponsive molecules and highly controlled polymer chains.

In one embodiment, the present disclosure provides a process for forming a conjugate between a bioresponsive molecule and at least one polymer chain. The process comprises polymerizing radically polymerizable monomers at a temperature of between about 4° C. and about 50° in the presence of an aqueous system comprising a bioresponsive molecule having at least one site specific functional initiator comprising a radically transferable atom or group, a transition metal that participates in a reversible reduction-oxidation cycle with at least one of the site specific functional initiator and a dormant polymer chain having a radically transferable atom or group, wherein the mole fraction of transition metal in a lower, activator oxidation state to transition metal in a higher, deactivator oxidation state is less than 20%, and a ligand that forms a stable complex with the transition metal catalyst, wherein the aqueous system comprises less than 30% by weight of organic solvent and monomer concentration and the total bioresponsive molecule concentration is less than about 3 mg/mL, and forming a conjugate between the bioresponsive molecule and the at least one polymer chain, wherein the at least one polymer chain has a molecular weight distribution of less than 1.35. In another embodiment, the transition metal has a total concentration in the system of less than 1000 ppm.

In another embodiment, the present disclosure provides for a conjugate between a bioresponsive molecule and one or more polymeric chains, wherein the one or more polymeric chains each have a molecular weight distribution of less than 1.20. In certain embodiments, the bioresponsive molecule is a molecule selected from the group consisting of a protein, a peptide, a nucleic acid, a carbohydrate, and a biologically active macromolecule.

BRIEF DESCRIPTION OF THE DRAWINGS

The following Figures assist in elucidating the disclosed process for preparation of well defined PPCs under conditions that do not alter the biological actions of the bio-initiator but do not limit the procedure to these exemplifying procedures.

OEOMA$_{475}$ is a biocompatible monomer, similar to PEG in properties, and was used in a grafting from reaction using 2-hydroxyethy 2-bromoisobutyrate bromide (HEBriB) and BSA functionalized by reaction with bromo-isobutyrate-ATRP initiators at two different concentrations of the BSA initiator (see Example 14). All reactions followed the same kinetic profile.

Figure 15:
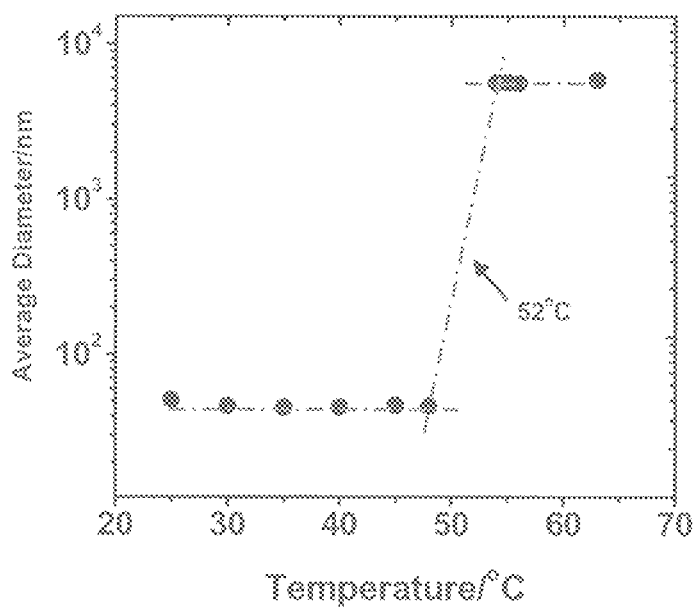

FIG. 15: Temperature dependent DLS spectra of the thermo-responsive GF BSA-O-[iBBr]$_{30}$.

Figure 16:
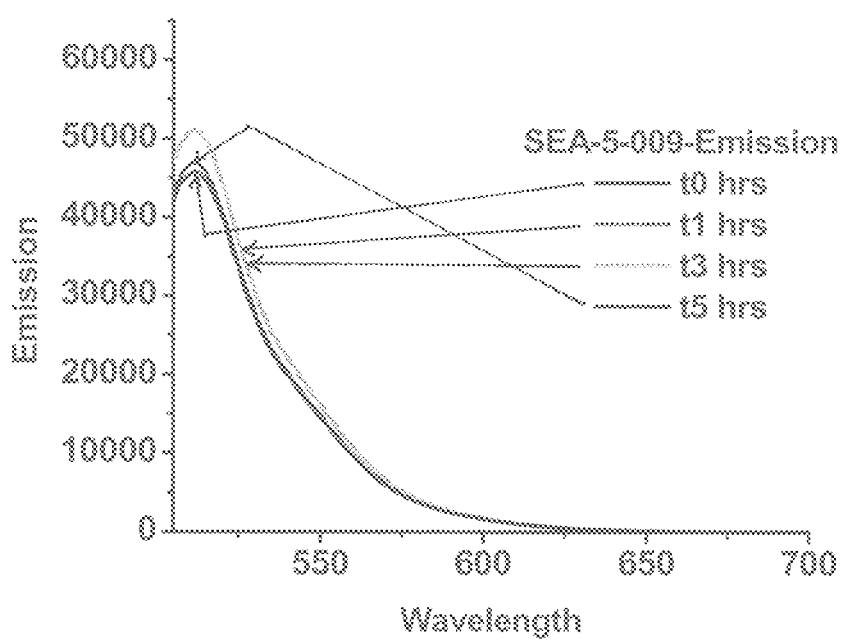

FIG. 16: Emission spectra of time samples from the polymerization of OEOMA$_{475}$ from GFP-O-iBBr. Samples were diluted 1:10 in 1× PBS and measured on a TECAN Safire2 plate reader.

ABBREVIATIONS

Atom Transfer Radical Polymerization (ATRP)
Protein-Polymer Conjugates (PPCs)
Reversible-Deactivation Radical Polymerization (RDRP)
Controlled Radical Polymerization (CRP)
Nitroxide Mediated Polymerization (NMP)
Activators Generated by Electron Transfer (AGET)
Initiator for Catalyst Activator Regeneration (ICAR)
Electrochemically mediated ATRP (eATRP)
Reversible Addition Fragmentation Transfer (RAFT)
Free Radical Polymerization (FRP)
Poly(Ethylene Glycol) (PEG)
Oligo(Ethylene Glycol) (OEG)
Green Fluorescent Protein (GFP)
Phosphate Buffer Saline (PBS)
Bovine Serum Albumin (BSA)
Tetraethylammonium cation (TEA)
Lower Critical Solution Temperature (LCST)
Silencing RNA (siRNAs)
Tris(2-Pyridylmethyl)amine (TPMA)
2,2'-Bipyridine (Bpy)
N-(n-Propyl)pyridylmethanimine (PI)
Ascorbic Acid (AA)
Gel Permeation Chromatography (GPC)
Dynamic Light Scattering (DLS)
Specific selected potential (E$_{app}$)
Tetraethylammonium bromide (TEABr)
2-Hydroxyethyl 2-bromoisobutyrate (HEBriB)
2-Hydroxyethyl 2-bromo-2-methylpropanoate (HEBrMeP)
Dimethylformamide (DMF)
Tetrahydrofuran (THF)
Oligo(ethylene glycol) methyl ether methacrylate (OEOMA$_{475}$)
Oligo(ethylene glycol) methyl ether acrylate (OEOA$_{475}$)
Cyclic Voltammetry (CV)
N-Hydroxysuccinimide (NHS)
Poly(ethylene oxide)isobutyryl bromide (PEO-iBBr)
Dimethylaminoethyl methacrylate (DMAEMA)
Molecular Weight Distribution ($M_w/M_n$)
Dimethylsulfoxide (DMSO)
Feeding Rate of Ascorbic Acid (FR$_{AA}$) de

DETAILED DESCRIPTION

The present disclosure describes a process for preparing conjugates between bioresponsive molecules and at least one polymer chain, where the at least one tethered polymer chain has a well defined structure, such as those provided by a well controlled radical polymerization processes exhibiting high initiation efficiency. The conjugates prepared by the methods herein display well defined conjugated polymer chains with narrow polydispersities (molecular weight distributions) that have been previously unattainable by conventional methods used for conventional PPH procedures. The conjugates are prepared under conditions typical of biological systems, such as, substantially aqueous reaction media and biologically compatible temperatures and pH's.

Other than the operating examples, or where otherwise indicated, all numbers expressing quantities of ingredients, processing conditions and the like used in the specification and claims are to be understood as being modified in all instances by the term "about". Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, may contain certain errors, such as, for example, equipment and/or operator error, necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of less than or equal to 10.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The present disclosure describes several different features and aspects of the invention with reference to various exemplary non-limiting embodiments. It is understood, however, that the invention embraces numerous alternative embodiments, which may be accomplished by combining any of the different features, aspects, and embodiments described herein in any combination that one of ordinary skill in the art would find useful.

A standard set of biologically compatible conditions that can be used in the synthesis of PPCs is defined as conditions that maintain protein stability. The target set for these conditions include use of a relatively low concentration of protein in an aqueous based polymerization medium. Furthermore, since most proteins become unstable when exposed to greater than 20% of organic media; i.e. high monomer volume fraction or presence of a co-solvent, a 10% (w/v) total organic solvent content, and near ambient temperatures were selected to conduct the polymerizations. However, conducting an ATRP under these biologically compatible conditions exacerbates several issues not normally encountered in known ATRP procedures. These issues include limited stability of the Cu based catalysts in dilute aqueous systems, particularly the $Cu^{II}$ complexes which can undergo dissociation leading to poorly controlled polymerization, interactions between Cu complexes and proteins, and relatively high ATRP equilibrium constants in water.

Procedures that resolve these issues are disclosed herein for each of the commonly utilized ATRP initiation procedures in addition to a newly developed electrochemically mediated procedure, eATRP.

Seeking to conduct an ATRP under biologically compatible conditions brings forth numerous issues typically absent when conducting an ATRP in predominately organic media and requires a significant step forward from current ATRP procedures. They include overcoming the repercussions of generation of high ATRP equilibrium constants in water [*Macromolecules,* 2009, 42(17), 6348-6360], which can lead to high radical concentrations and consequentially high termination rates. Moreover, conducting an ATRP in aqueous media suffers from many additional complications, which include dissociation of copper(II) halide species, lability of the copper(I)/ligand complex, disproportionation of certain copper(I) species [*ACS Symposium Series,* 2006, 944, 56-70], and hydrolysis of the carbon-halogen bond [*Macromolecules* 2004, 37, 9768]. These factors all contribute to poorly controlled polymerizations with broad distributions, as a result of low deactivator concentrations and loss of ATRP activity. Furthermore, when utilizing proteins as initiators, undesired binding of the protein to the ATRP catalyst can occur which may denature the protein [*Polym. Chem.* 2010, 1, 944] and cause inactivity of the copper complex when a ligand displaying a sufficiently high binding constant is not used. In addition, many monomers and polymers of interest have limited solubility in pure water. These challenges indicate that it is important to develop general conditions for synthesis of well-defined PPCs by the "grafting from" approach using ATRP in aqueous media.

As noted above, in addition to developing conditions that overcome the concerns associated with the catalyst that present problems for aqueous based ATRP reactions, when targeting preparation of PPCs the reaction conditions should be carefully selected to minimize protein denaturation that can occur from the presence of a relatively high volume fraction of monomer in the reaction mixture. Denaturation causes proteins, or nucleic acids, to lose their tertiary and/or secondary structure which is normally caused by application of some external stress or the presence of a non-natural compound, such as a strong acid or base, a high concentration of an inorganic salt or an organic solvent, e.g., alcohol or chloroform, or heat. Denatured proteins can exhibit a wide range of modified characteristics, from loss of solubility to communal aggregation.

Factors that should be optimized include total solvent/monomer concentration, ratio of monomer to solvent, type of solvent(s), ligand and Cu(I):Cu(II) ratio, halide counterion, selection of reducing agents and procedures for addition of the selected reducing agent to an ATRP, particularly an ATRP with low copper concentration for catalyst reactivation, in absence or presence of buffers, and if present whether the counterion on the buffers interact with either the catalyst or protein. Particularly since the polarity of the chosen solvent can affect the final degree of control over the polymerization.

Cu(II) complexes formed in water are generally not efficient deactivators in a standard ATRP and this has been addressed by adding a ligand substitute [U.S. Pat. No. 6,624,262] or changing the solvent to promote the formation of the tertiary Cu(II):L complex, for example, many literature sources have typically used a 30% methanol or DMF co-solvent when conducting ATRP in water, but proteins are sensitive to the type and concentration of solvents and the procedures used in prior art papers are outside the realm of acceptability. As discussed below the ligands effect on the rate and control of ATRP in water should be balanced with the ligands ability to continue to form a catalytic complex with copper in the presence of proteins.

Four exemplary ATRP initiation/control systems are evaluated, a classic ATRP, an AGET/ARGET ATRP, an ICAR ATRP and the most recently developed electrochemically mediated ATRP (eATRP) in order to identify conditions, that contrary to prior art procedures, allow one to conduct the full spectrum of ATRP reactions in a biologically compatible environment.

One embodiment of the present disclosure provides a process for forming a conjugate between a bioresponsive molecule and at least one polymer chain. The process may comprise polymerizing radically polymerizable (co)monomers at a temperature of between about 4° C. and about 50° C. in the presence of an aqueous system comprising a bioresponsive molecule having at least one site specific functional initiator comprising a radically transferable atom or group, a transition metal that participates in a reversible reduction-oxidation cycle with at least one of the site specific functional initiator and a dormant polymer chain having a radically transferable atom or group, and a ligand that forms a stable complex with the transition metal catalyst, and forming a conjugate between the bioresponsive molecule and the at least one polymer chain, such as by a grafting from process, wherein the at least one polymer chain has a molecular weight distribution of less than 1.35.

According to these embodiments, the transition metal may have a total concentration in the system of less than 1000 ppm, wherein the mole fraction of transition metal in a lower, activator oxidation state to transition metal in a higher, deactivator oxidation state is less than 20%, or even less than 10%, or in some embodiments less than 5%, and even less than 2% or less than 1%. In other embodiments the transition metal may have a total concentration in the system of less than 500 ppm, or even less than 300 ppm. In specific embodiments, the total concentration of the transition metal may have a lower value of 100 ppm, or in various embodiment 10 ppm, or even 5 ppm and in certain embodiments 1 ppm. In one non-limiting embodiment, the total concentration of the transition metal may be from 10 ppm to 300 ppm.

According to various embodiments, the polymerization occurs in a substantially aqueous system that is compatible with the bioresponsive molecule. Since for example, in certain non-aqueous systems or even aqueous systems with high contents of organics or inorganic salts, the bioresponsive molecule may lack stability and/or may degrade under the solvent conditions to lose at least a portion of one or more of its secondary, tertiary, and/or quaternary structure; topology; and activity, such as its biological activity. Thus, according to certain embodiments, the aqueous system of the polymerization may comprise less than 30% by weight of combined organic compound concentration, such as, for example, organic compounds selected from organic solvent, ligand, and/or monomer concentration. In other embodiments, the aqueous system may comprise less than 20% by weight of combined organic compounds or even less than 15% by weight of combined organic compounds. Suitable organic solvents may include, but are not limited to DMSO, methanol, ethanol or other $C_1$-$C_4$ alcohols, THF, DMF, acetonitrile, and mixtures of any thereof. In specific embodiments, the organic solvent concentration in the aqueous system may be less than 20% by weight, or even less than 10% by weight. In other embodiments, solvent or monomer, including additional solvent and/or monomer, may be added slowly to the predominantly aqueous medium to maintain a polymerization medium wherein the formed PPC remains in solution while maintaining a low molecular weight organic content below 20%. Furthermore this can provide a procedure for introducing some less soluble water soluble species into the system for forming the PPC.

According to certain embodiments, the initial concentration of the bioresponsive molecule in the aqueous system may be less than about 3 mg/mL, or even less than about 1 mg/mL. Suitable bioresponsive molecules may include those bioresponsive molecules described in detail herein. For example, in specific embodiments, the bioresponsive molecule may be a molecule selected from the group consisting of a protein, an enzyme, a polypeptide, a peptide, a nucleic acid, a polynucleotide, a carbohydrate, a biologically active macromolecule, and combinations of these molecules (for example a combination of a protein and a carbohydrate etc.). In specific embodiment, the bioresponsive molecule may be a protein, such as, for example, an enzyme. According to the various embodiments, the aqueous system and polymerization conditions are selected so that the bioresponsive molecule, such as the protein or enzyme, retains its structure (such as secondary, tertiary, and/or quaternary structure), topology, and/or activity (for example enzymatic activity) in the formed conjugate. That is, after the polymerization, the conjugate has the same or similar structure, topology and/or activity as the original bioresponsive molecule.

Polymerizing the radically polymerizable monomers in the presence of the aqueous system to produce the conjugate having highly defined polymer chains may be attained by a controlled radical polymerization process. Suitable controlled radically polymerization processes may include, for example, classic ATRP processes, reverse ATRP processes, AGET ATRP processes, ARGET ATRP processes, ICAR ATRP processes, transition metal mediated RAFT polymerization processes, and eATRP processes, as described herein and in the references incorporated herein. In certain embodiments, the controlled polymerization process may be selected from an AGET ATRP process, an ARGET ATRP process, an ICAR ATRP process, and an eATRP process. According to these embodiments, the polymerizing process is generally a grafting from polymerization process, wherein the bioresponsive molecule comprises at least one site specific functional initiator to initiate the polymerization, such as a radically transferable atom or group. The controlled radical polymerization process thereby forms the at least one polymer chain from the site specific functional initiator on the bioresponsive molecule by a controlled radical "grafting from" polymerization process.

Transition metals suited for conducting controlled radical polymerization processes are described in detail in the incorporated references. In specific embodiments, the transition metal that participates in a reversible reduction-oxidation cycle may be copper, wherein the $Cu^+$ is the lower, activator oxidation state of the transition metal; and $Cu^{2+}$ is the higher, deactivator oxidation state of the transition metal. In certain embodiments, the transition metal may be added to the system as the halide CuX, $CuX_2$, or a mixture thereof, such as the chloride or bromide species (i.e., CuCl, $CuCl_2$, CuBr and/or CuBr$_2$). In other embodiments, other counterions may be used, such as phosphate counterions, sulfate counterions and the like.

The ligand that is capable of forming a stable complex with the transition metal to form the active catalyst may be any of the ligands utilized in controlled radical polymerization processes described in detail in the incorporated references. In specific embodiments, the ligands may be a strongly coordinating ligand, such as a nitrogen based ligand where the nitrogen coordinates and/or chelates to the transition metal to form the stable complex. Non-limiting examples of nitrogen containing ligands include 2,2'-bipyridyl ligands and substituted 2,2'-bipyridyl ligands, tris(2-pyridylmethyl)amine, tris[2-(dimethylamino)ethyl]amine and substituted tris(2-pyridylmethyl)amine ligands, (Me$_6$TREN), N,N,N',N'',N''-pentamethyldiethylenetriamine (PMDETA), or other nitrogen containing ligand used in transition metal mediated controlled radical polymerization processes. Other, non-nitrogen ligands may also be used in the polymerization processes described herein and are within the broad scope of the claimed invention.

In specific embodiments, the aqueous system may further comprise a buffer. In certain embodiments, the buffer may be a phosphate buffer, such as any of the phosphate buffers described herein, for example a phosphate buffer saline (PBS) buffer. Buffers may be used, for example, to control the pH of the aqueous system and make the system compatible for the bioresponsive molecule. Buffers may be selected to minimize formation of insoluble salts with the transition metal and displacement of ligands from the active transition metal catalyst. According to certain embodiments, the buffer in the aqueous system may have a concentration ranging from about 1 mM to about 33 mM. According to various embodiments, the buffer may comprise the same counterion as the radically transferable atom or group. For example, in those embodiments where the radically transferable atom or group may be a bromine or chlorine, the buffer may comprise a bromide or chloride counterion.

In specific embodiments, the polymerization process may comprise one of an AGET ATRP process, an ARGET ATRP process, and an ICAR ATRP polymerization process. According to various embodiments, in these polymerization processes the transition metal may be added primarily as the higher, deactivator oxidation state transition metal and a fraction of the transition metal may be continuously reduced from the higher, deactivator oxidation state to the lower, activator oxidation state by the controlled addition of a reducing agent or by the controlled degradation of an added free radical initiator. Examples of reducing agents and free radical initiators are described in detail in references incorporated herein. For example, in those embodiments comprising controlled degradation of an added free radical initiator to effect reduction of the deactivator transition metal catalyst to the activator transition metal catalyst, the added free radical initiator may be a free radical initiator known in the art, such as, but not limited to, azo compounds, for example, azobisisobutyronitrile (AIBN) and the like, or organic peroxide compounds, such as di-t-butylperoxide, benzoyl peroxide and the like, which may be activated by thermal means or by exposure to UV light. Examples of reducing agents may include inorganic reducing agents and/or organic reducing agents. Non-limiting examples of inorganic reducing agents include tin based reducing agents, such as, Sn$^{2+}$ agents, for example tin(II) 2-ethylhexanoate (Sn(EH)2) or other common inorganic reducing agents, such as NaNO$_2$, Na$_2$S$_2$O$_3$, NaHSO$_3$, hydrazine hydrate, hydroxyl amine hydrochloride, or sodium borohydride. Non-limiting examples of organic reducing agents include glucose, ascorbic acid, and phenyl hydrazine, as well as other common organic reducing agents and antioxidants. In specific non-limiting embodiments, the reducing agent may be Sn(EH)2 or ascorbic acid (AA).

According to other embodiments, the polymerization process may comprise an electrochemically medicated (eATRP) process, such as described in International Application PCT/US2011/065578. According to various embodiments, in these polymerization processes the transition metal may be added primarily as the higher, deactivator oxidation state transition metal and a fraction of the transition metal may be continuously reduced from the deactivator state to the activator state by application of a potentiometric or galvanistic charge sufficient to maintain the targeted ratio of transition metal in the activator state to transition metal in the deactivator state, such as a mole fraction of less than 30%, or even less than 20%.

Still other embodiments of the present disclosure are directed to a composition of matter comprising a conjugate between a bioresponsive molecule and one or more polymeric chains, wherein the one or more polymeric chains each have a molecular weight distribution of less than 1.20 and/or a predetermined and controlled degree of polymerization. As described in detail herein, prior art polymer protein hybrids lack well defined structures, such as where the structure of the polymeric chain are not controlled and/or do not display a low molecular weight distribution, as shown by shoulders and/or tailing in the GPC curves of the prior art hybrid compounds prepared by grafting from-type polymerization reactions. As described herein, the conjugate may comprise a bioresponsive molecule selected from the group consisting of a protein, an enzyme, a polypeptide, a peptide, a nucleic acid, a polynucleotide, a carbohydrate, a biologically active macromolecule, and combinations of these molecules. In certain embodiments, the bioresponsive molecule may be a protein or enzyme.

According to various embodiments of the conjugate as described herein the one or more polymeric chains may have a structure resulting from a controlled radical polymerization process, for example a controlled radical polymerization process selected from the group consisting of a classic ATRP process, a reverse ATRP process, an AGET ATRP process, an ARGET ATRP process, an ICAR ATRP process, a RAFT polymerization process, and an eATRP process, as described herein and in the references incorporated herein. According to these embodiment, the one or more polymeric chains may be formed from radically polymerizable monomers, such as radically polymerizable monomers described in the various references incorporated herein and described in this disclosure.

In specific embodiments of the conjugates described herein, the one or more polymeric chains may be linked to the bioresponsive molecule by a cleavable linkage. For example, according to certain embodiments, the cleavable linkage may comprise a cleavable functionality selected from the group consisting of an ester functionality, a disulfide functionality, a phosphate functionality, and a thioester functionality. According to these embodiments, the bioresponsive molecule may be chemically modified to have at least one site specific functional initiator, wherein the at least one site specific functional initiator may be linked to the bioresponsive molecule by the cleavable linkage. The one or more polymeric chains may be polymerized, by a grafting from process, from the at least one site specific functional initiator comprising a radically transferable atom or group by a controlled radical polymerization process. According to this process, the resulting polymeric chain will be linked to the bioresponsive molecule by a cleavable linkage that may be later cleaved to release the one or more polymeric chains from the bioresponsive molecule by a chemical process, such as hydrolysis of the ester, phosphate, or thioester functionality or by reduction of the disulfide functionality.

One embodiment of the present methods utilizes water as a solvent with less than 300 ppm catalyst complex comprising a strongly coordinating ligand for polymerization of radically copolymerizable monomers from an initiator comprising one or more transferable atoms or groups at ambient temperatures wherein the catalyst complex is continuously reduced from the higher oxidation state to a lower oxidation state by controlled addition of a reducing agent.

Herein are described ATRP methodologies to create PPCs using the "grafting from" approach in aqueous media under biologically compatible conditions. However the conditions can also be applied to grafting from non-biological entities under the environmentally benign conditions defined herein including procedures with low concentrations of the catalyst complex, i.e. less than 500 ppm, in the presence of water as the predominant solvent.

The defined biologically compatible conditions are designed to preserve the protein's secondary and tertiary structure and activity, while simultaneously offering control over a grafting from polymerization. Preservation of a protein's native structure imposes several restrictions on reaction conditions; specifically in regard to reaction temperatures, concentration of reagents, and organic content in the contacting media. Thus, polymerizations should be performed at or near ambient temperatures. Ambient temperatures can be considered temperatures between 4° C. and 50° C. preferably between 20° C. and 45° C. and exemplified herein by reactions conducted at 30° C., to avoid thermal denaturation of the protein. The reaction can however be conducted within the temperature range where the specific protein or biologically responsive molecule does not undergo denaturation. Also, most proteins denature when high concentrations of the proteins are dissolved in solutions, and hence, proteins or other bioactive molecules should be kept under dilute conditions; less than 3 mg/mL, preferably near 2 mg/mL. The presence of a high concentration of organic media can also destabilize proteins therefore limiting the total organic content of the polymerization medium to less than 30%, preferably less than or equal to 20%, (monomer and co-solvent) is a selected target.

The choice of ligand can also have significant influence over the resulting polymerization in an ATRP. In particular, varying the ligand can have a dramatic effect on the ATRP equilibrium, shifting it either toward a more active or more dormant state. Initially three ligands were selected ranging from a ligand forming a very activating transition metal complex; tris(2-pyridylmethyl)amine (TPMA), a moderately activating ligand, 2,2'-bipyridine (Bpy), and a ligand forming a highly deactivating metal complex, N-(n-propyl) pyridylmethanimine (PI), to provide some guidance to the range of catalyst activity suitable for the polymerization [*J. Am. Chem. Soc.* 2008, 130, 10702].

Successful ATRP from a protein macroinitiator requires the protein to be stable in the presence of copper halide/ligand complexes. Therefore, GFP was selected as a model protein to test protein stability in the presence of different pre-complexed Cu:ligand species, under envisioned targeted reaction conditions, i.e. 1 mg/mL GFP, 10% monomer in 0.1 M phosphate buffer saline (PBS) (pH=7.4). PBS is a widely utilized buffer in reactions associated with proteins. GFP was selected for the stability studies because denaturation of its beta-barrel structure leads to a loss of its fluorescent properties [*Biochemistry* 2004, 43, 14238]. Fluorescence measurements showed that copper complexes formed with TPMA or Bpy do not greatly influence the GFP's tertiary structure as indicated by similar emission spectra for GFP and GFP in the presence of $CuCl_2$/TPMA or $CuCl_2$/bpy, FIG. 2. In contrast, upon the addition of pre-complexed $CuCl_2$/PI the GFP denatured, demonstrated by a 100 fold decrease in fluorescence intensity of GFP, which are comparable with results seen upon the addition of a sample of an uncomplexed copper halide to GFP solution, right hand bars in FIG. 2, thereby indicating that a strong complex should be formed between the ligand and transition metal to prevent denaturation. This test with GFP can be used as a screening tool for other metal/ligand complexes envisioned for grafting from bio-responsive molecules.

Based on the above results, Bpy and TPMA ligands were selected for continuation of the development of a "classic" ATRP under biologically compatible conditions. In a "classic" ATRP a mixture of cuprous and cupric halides is added to the reaction. In the examples discussed below, a ligand with a higher $k_{deact}$, i.e. the more deactivating ligand, Bpy, is compared to a ligand with higher $k_{act}$. TPMA based catalyst complexes are investigated even though they are harder to control in aqueous systems as they provide a possibility to develop conditions that use lower concentrations of catalyst, e.g., ARGET, ICAR ATRP, or eATRP procedures, if other hurdles can be overcome.

Bovine serum albumin (BSA) was selected as an exemplary protein to evaluate the reaction conditions required to conduct a controlled "grafting from" ATRP because of its widespread usage as a valid model protein, and due to its abundance and low cost. When a functionalized BSA was used as the bio-initiator and PI ligands complexes with Cu(II) or Cu(I) are added to solutions containing BSA the protein immediately precipitates. These observations indicate that the proteins, GFP and BSA, are better ligands at binding copper than PI and hence PI's are not suitable ligands and indicate that the GFP test is a valid means to evaluate suitability of other ligands with copper or with other transition metals such as iron in the polymerization. Indeed the GFP stability test described herein can be used to confirm that other possible ligands for catalyst formation do not denature the protein.

While the examples focus on use GFP and BSA as exemplary proteins there are multiple examples of proteins and polypeptides that can be used to form PPCs including but not limited to, proteins, polypeptides, and peptide sequences. Examples of proteins and polypeptides include any natural or synthetic polypeptide or polynucleotide that may be administered to a patient.

Examples of polypeptides include, but are not limited to, those of interest in medicine, agriculture and other scientific and industrial fields, particularly including therapeutic polypeptides such as interferons, insulin, monoclonal antibodies, blood factors, colony stimulating factors, growth hormones, interleukins, growth factors, therapeutic vaccines, calcitonins, tumor necrosis factors, and enzymes. Specific examples of such therapeutic proteins include, without limitation, enzymes utilized in enzyme replacement therapy; hormones for promoting growth in animals, or cell growth in cell culture; anticoagulants and active proteinaceous substances used in various applications, for example, in biotechnology or in medical diagnostics. Specific examples include, but are not limited to: asparaginase; glutamase; arginase; arginine deaminase; adenosine deaminase ribonuclease; cytosine deaminase, trypsin; chymotrypsin, papin, epidermal growth factor, insulin-like growth factor, transforming growth factor, nerve growth factor, platelet-derived growth factor, bone morphogenic protein, fibroblast growth factor and the like; somatostatin; somatotropin; somatropin; somatrem; calcitonin; parathyroid hormone; colony stimulating factors; clotting factors; tumor necrosis factors; interferons; interleukins; gastrointestinal peptides, such as vasoactive intestinal peptide, cholecytokinin, gastrin, secretin, and the like; erythropoietins; growth hormone; vasopressins; octreotide; pancreatic enzymes; dismutases such as superoxide dismutase; thyrotropin releasing hormone; thyroid stimulating hormone; luteinizing hormone; luteinizing hormone-releasing hormone; growth hormone-releasing hormone; tissue plasminogen activators; interleukin-1; interleukin-15; receptor antagonist; glucagon-like peptide-1; leptin, ghrelin; granulocyte monocyte colony stimulating factor; interleukin-2; interferons such as interferon-[alpha]; adenosine deaminase; uricase; human growth hormone; asparaginase; macrophage activator; chorionic gonadotropin; heparin; atrial natriuretic peptide; hemoglobin; retroviral vectors; relaxin; cyclosporin; oxytocin; vaccines; monoclonal antibodies; single chain antibodies, ankyrin repeat proteins, affibodies, and the like; and analogs and derivatives thereof.

Examples of polynucleotides include, but are not limited to, polynucleotides and oligonucleotide sequences, including DNA and RNA, which may be double-stranded or single-stranded. Examples of polynucleotides include any natural or synthetic polynucleotide that may be administered to a patient. Examples of polynucleotides include, but are not limited to, antisense oligonucleotides, silencing RNA (siRNAs), anti-microRNA that target genes such as bcl-2, V2R, EphA2, caveolin-1, TNF-alpha, MIF, GFP, Raf-1, c-raf, luciferase, VEGF, SCV, Fas, Ins2, Caspase-8, and HBsAg.

Examples of aptamers include, but are not limited to, vascular endothelial growth factor aptamer, Ricin aptamer, pepocin aptamer, gypsphilin aptamer, thrombin aptamer, activated plasma protein C aptamer, HIV-1 reverse transcriptase, HIV-1 integrase, protein kinase C aptamer, human neutrophil elastase aptamer, L-selectin aptamer, P-selectin aptamer, Yersinia protein tyrosine phosphatase aptamer, phospholipase A2, angiogenin aptamer, and rhinovirus capsid protein aptamer.

Other examples of biomolecules include, but are not limited to, oxytocin, vasopressin, adrenocorticotrophic hormone, prolactin, luliberin or luteinising hormone releasing hormone, growth hormone, growth hormone releasing factor, somatostatin, glucagon, gastrin, tetragastrin, pentagastrin, urogastroine, secretin, calcitonin, enkephalins, endorphins, angiotensins, renin, bradykinin, bacitracins, polymixins, colistins, tyrocidin, gramicidin's, and synthetic analogues, modifications and pharmacologically active fragments thereof, monoclonal antibodies and soluble vaccines.

The polymer that is grown in situ from the bio-molecule confers desirable properties to the conjugate. The term "polymer" as used herein is intended to encompass a homopolymer, co-polymer, ter-polymer, block polymer, etc., and blends, combinations and mixtures thereof. Examples of polymers include, but are not limited to, functionalized polymers, such as a polymer comprising one or more 5-vinyltetrazole monomer units and having a molecular weight distribution less than 1.35. The polymer may be or contain one or more of a linear polymer, a branched polymer, a hyperbranched polymer, a dendritic polymer, a star block copolymer, a comb polymer, a graft polymer, a brush polymer, a bottle-brush copolymer and a crosslinked structure, such as a block copolymer comprising a block of 5-vinyltetrazole monomer units.

Polymers that can be produced in situ from specific sites on the biomolecule or polypeptide according to the methods disclosed herein include, without limitation, polyesters, poly(meth)acrylamides, poly(meth)acrylates, polyethers, polystyrenes, and polynorbornenes.

As noted above, BSA, a commercially available protein, was selected as being suitable for defining biologically compatible conditions that allow conducting an ATRP, since BSA is a protein commonly used in the "grafting from" method. BSA has 35 lysine residues available for functionalization. Therefore, if 2 mg/mL of BSA are quantitatively modified with ATRP initiators then an initiator concentration of 1 mM would result. Suitable initiator concentrations would be 0.1-3 mM with control at these concentrations. To optimize reaction conditions for PPC synthesis, this exemplary study investigated the effects of different copper halides, bromide or chloride, and ligand, Bpy and TPMA, in a "classic" ATRP and the effect of quantity and feeding rate of a reducing agent in an AGET ATRP "grafting from" reaction. After defining conditions for grafting from BSA under standard ATRP conditions and AGET ATRP conditions a very systematic study was undertaken to establish conditions where the concentration of catalyst could be reduced below 1000 ppm preferentially below 500 ppm, or optimally below 300 ppm to allow a more environmentally compatible ARGET ATRP to be conducted. This was a particularly difficult task as both oxidation states of the transition metal catalyst complexes are generally not stable at low concentrations in the presence of high concentrations, greater that 75%, of water.

In addition to assessing protein stability in the presence of the selected catalyst, rigorous analysis of the synthetic polymer formed during the preparation of the PPC is required for complete characterization of the resulting bioconjugate, as it provides the information that demonstrates the level of control over the "grafting from" polymerization. Therefore, in contrast to prior "grafting from" work the protein was modified with cleavable ester initiator, (BSA-O-[iBBr]$_{30}$), in order to facilitate direct analysis of the polymer grafted from BSA, Scheme 2. The ester bond linking the initiator to the protein can be selectively cleaved by 5% KOH (w/v) solution, without affecting the oligoethylene oxide methyl ether side chains [*Macromolecules* 2007, 40, 8540]. This allows real time monitoring of the polymers formed in the "grafting from" reactions, since the polymers can be cleaved from the BSA and directly analyzed using gel permeation chromatography (GPC).

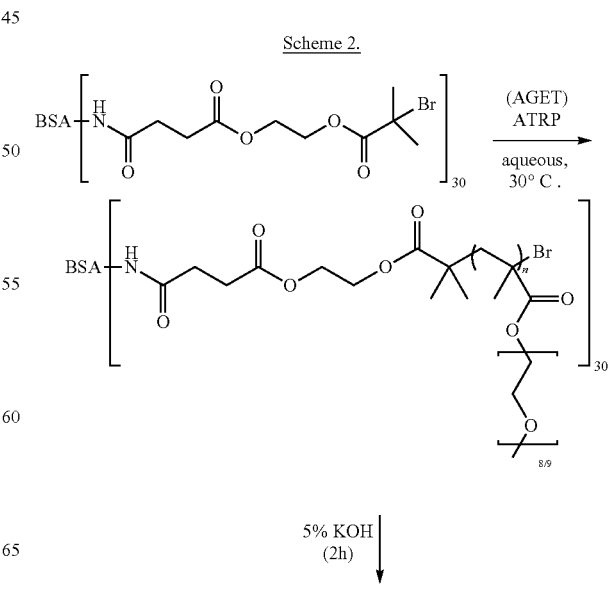

-continued

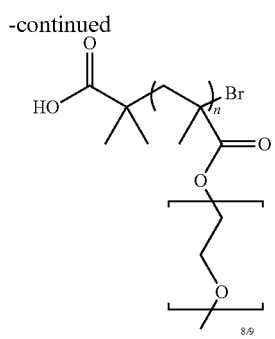

Previous work showed that a key parameter for conducting a successful ATRP in protic solvents is the presence of high concentrations of the Cu(II) halide species, up to 80% of total copper, due to the high equilibrium constant formed by an ATRP catalyst complex in aqueous systems which is exacerbated by partial dissociation of the deactivator in highly polar media [*Macromolecules* 2004, 37, 9768]. Based on these results, 10% of the total copper added to the reaction was Cu(I) and the remaining fraction was Cu(II). Initial experiments were performed with a PEO-macroinitiator (PEO-iBBr), Scheme 3, and then later translated to the BSA-O-[iBBr]$_{30}$ system (Scheme 2).

Scheme 3. AGET ATRP of OEOMA$_{475}$ under biologically compatible conditions.

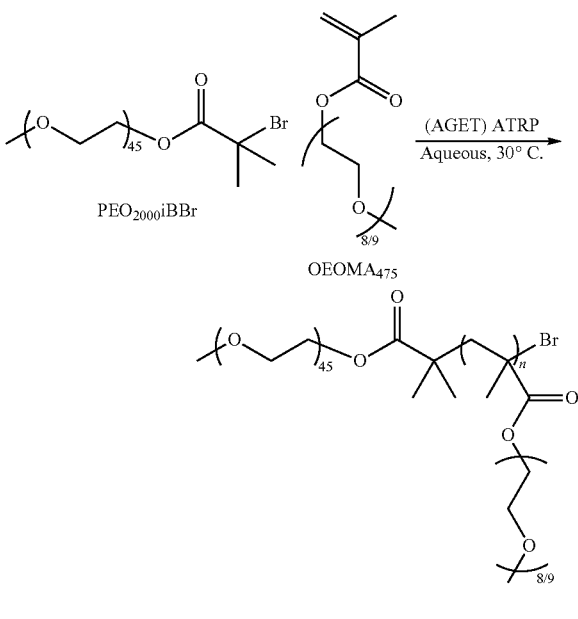

A target, which represents a summary of the techniques required for protein stability discussed in Hermanson, G. T. *Bioconjugate Techniques*; Academic Press: San Diego 1996, was set for the reaction. It was envisioned that the selected conditions would not adversely affect the topology of the protein or other biologically responsive molecule during the polymerization reaction.

This target was far from the state of the art in the presently disclosed procedures for conducting an ATRP and included certain exemplary embodiments:

A ratio of water to organic compounds of 80:20.

The ≤20% organic media would include the biological molecule, monomer and any added solvent.

Solvent may be added to allow the formed protein-polymer conjugate to remain in solution.

The reaction should be conducted below 50° C., or even below 40° C.

The ligand should be selected to form a stable $Cu^{II}$ complex that can deactivate the growing radical.

The ligand should form a catalyst complex that does not denature GFP.

A buffer may be added to enable the catalyst complex to retain its halogen counterion in the presence of such high concentration of water.

An exemplary set of biologically compatible conditions was defined as ~3 mg/mL protein concentration, i.e., 1 mM of the exemplary BSA initiator, no more than 20% (v/v) monomer/solvent, and near ambient temperatures in aqueous media.

The nature of halogen atom in both the catalyst and alkyl halide has a significant impact on the ATRP process. Therefore, the first parameter evaluated was a comparison of catalysts based on copper bromide and copper chloride under dilute aqueous conditions, Table 1. In these "classic" ATRP experiments, conducted with a high concentration of copper catalyst, a nine fold excess of Cu(II)X$_2$/L was used with respect to Cu(I)X/L to promote formation of ratio of Cu(I) to Cu(II) that provided a suitable deactivation rate and a lower rate of polymerization, in response to the expected high ATRP equilibrium constant in aqueous media.

TABLE 1

Experimental conditions of classic ATRP from PEO-iBBr and BSA-O-[iBBr]$_{30}$

| Run | M/I/CuX/CuX$_2$/L | I | L | X | Conv./% | $M_{n,theo}$ × $10^{-3}$ | $M_{n,GPC}$ × $10^{-3}$ | $M_w/M_n$ |
|---|---|---|---|---|---|---|---|---|
| 1 | 455/1/1/9/22 | PEO | bpy | Br | 45 | 94 | 108 | 1.54 |
| 2 | 455/1/1/9/22 | PEO | bpy | Cl | 27 | 55 | 58 | 1.16 |
| 3 | 455/1/1/9/11 | PEO | TPMA | Br | 2 | 40 | 12 | 1.27 |
| 4 | 455/1/1/9/11 | PEO | TPMA | Cl | 2 | 36 | 18 | 1.22 |
| 5 | 227/1/1/9/21 | BSA | bpy | Br | 66 | 71 | 100 | 1.16 |
| 6 | 227/1/1/9/11 | BSA | bpy | Cl | 58 | 63 | 97 | 1.18 |
| 7 | 227/1/1/9/21 | BSA | TPMA | Br | 5 | 5 | 40 | 1.10 |
| 8 | 227/1/1/9/11 | BSA | TPMA | Cl | 2 | 2 | 35 | 1.16 |

1 mM initiator, 10-20% monomer (v/v), water, 30° C., 4 h of polymerization.

Polymerizations were conducted with $[OEOMA_{475}]_0$=0.45M and $[OEOMA_{475}]/[I]/[CuX]/[CuX_2]/[L]$=455/1/1/9/[L] with the [L] for TPMA=11 and Bpy=22.

Figure 3A:
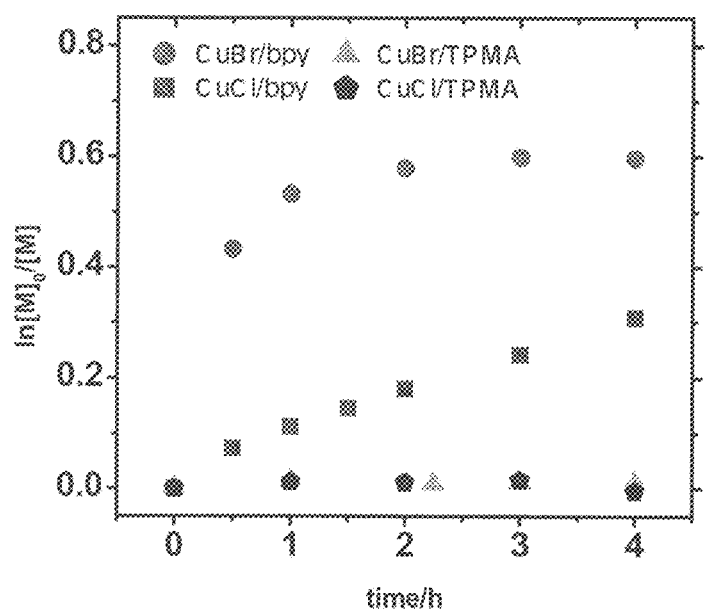
FIG. 3(A): Effect of copper halide (X=Br or Cl) on ATRP of OEOMA$_{475}$ under aqueous conditions at 30° C. First order kinetic plot.
Figure 3B:
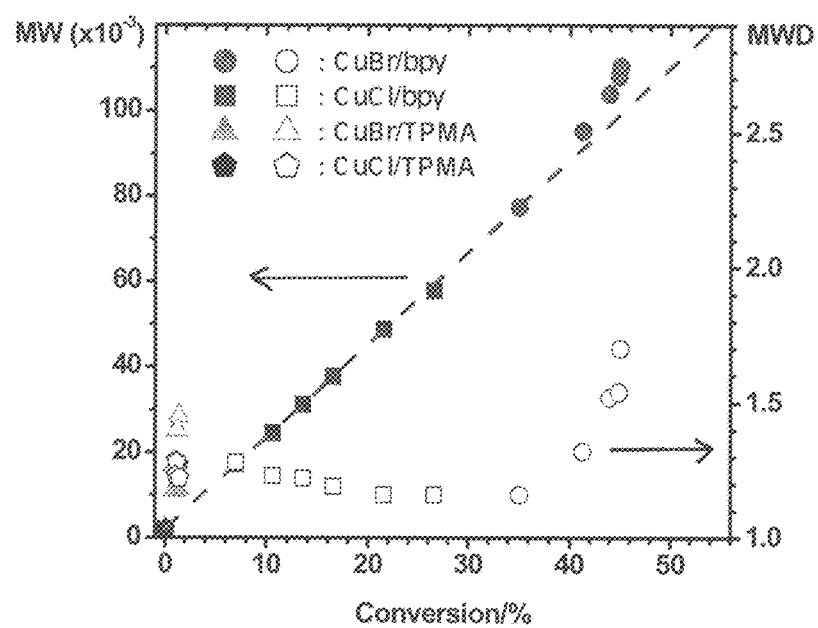
FIG. 3(B): Effect of copper halide (X=Br or Cl) on ATRP of OEOMA$_{475}$ under aqueous conditions at 30° C. $M_n$ (solid shapes) and $M_w/M_n$ (open shapes) versus conversion plot.
Figure 4A:
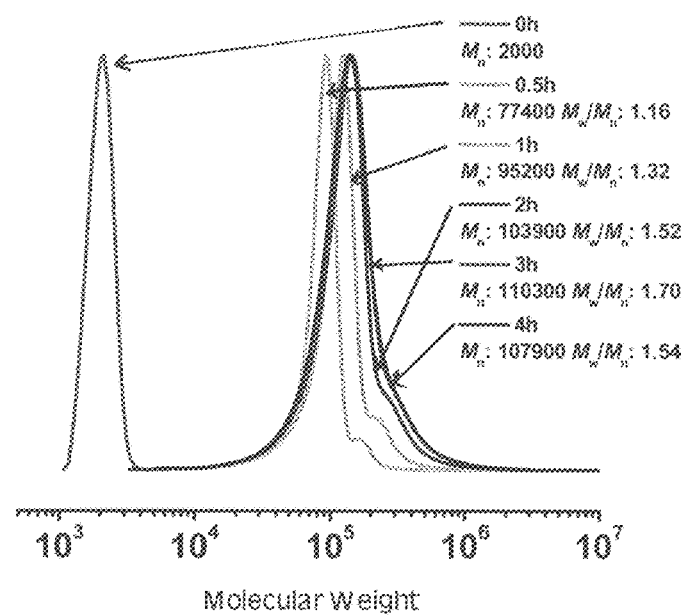
FIG. 4(A): GPC traces for CuBr/CuBr$_2$/bpy.
Figure 4B:
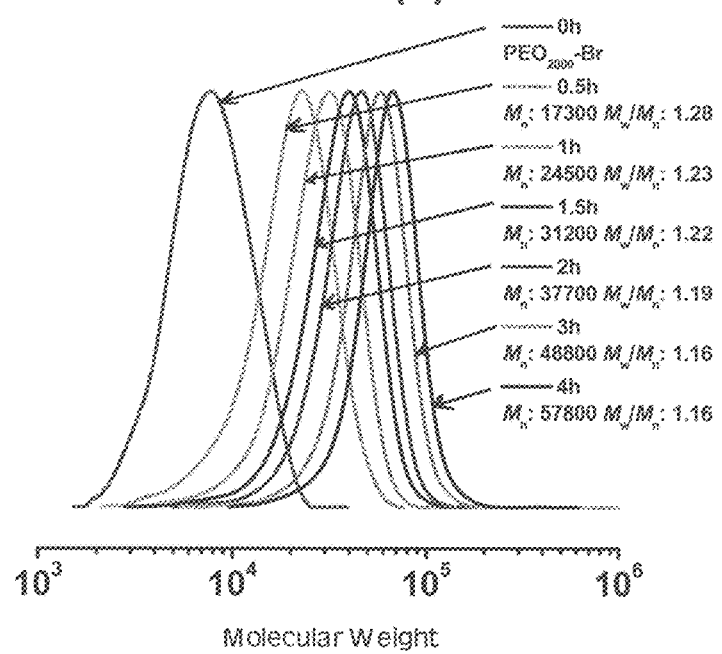
FIG. 4(B): GPC traces for CuCl/CuCl$_2$/bpy.

When Bpy was the ligand and bromine the counterion in the catalyst system the initial rate of polymerization was rapid but decreased dramatically after 1 hour, reaching a final monomer conversion of ca. 75%, FIG. 3(A). Molecular weight values were fairly close to their theoretically predetermined values, FIG. 3(B), although $M_w/M_n$ values increased to ca. 1.8 after conversion reached 40%. In contrast, the chlorine based catalyst system provided linear first-order kinetics, and a linear increase in molecular weight with monomer conversion and gradual decrease in the $M_w/M_n$. GPC curves show that the system with bromine as the counterion displayed a high MW shoulder, FIG. 4(A), while the chlorine based system resulted in a narrow normal distribution curve that moved cleanly to higher MW as the reaction progressed, FIG. 4(B).

Surprisingly, when taken in conjunction with the results disclosed and discussed below, this does not mean the bromine catalyst can not provide a well controlled polymerization only that a higher ratio of $Cu(II)Br_2/L$ to $Cu(I)Br/L$ should be added to the reaction, or generated in situ, for procedures starting with 100% Cu(II) to increase the targeted [Cu(II)] in the reaction medium thereby reducing the concentration of radicals formed and hence termination by radical coupling reactions. Therefore when bromine is employed as the transferable atom in aqueous media the % $Cu(II)Br_2/L$ complex present in the reaction medium during the polymerization should be greater than 95%.

Furthermore, as described in greater detail in the following discussion on the runs listed in Table 2, TPMA is not too active a catalyst for water based media but can be controlled in AGET and ARGET ATRP systems. Scheme 4 illustrates the mechanism that operates for activators generated by electron transfer (AGET) ATRP [*Macromolecules*, 2005. 38(10): 4139-4146; *J. Am. Chem. Soc.* 2005. 127(11): 3825-3830], where the precursor of a more active ATRP catalyst complex is added to a reaction medium and a fraction of the higher oxidation state catalyst complex is reduced to the activator. In the examples discussed herein ascorbic acid (AA) was used as the exemplary reducing agent as ascorbic acid is a water soluble biocompatible organic molecule. Other water soluble reducing agents, including those discussed in incorporated references, would also be applicable in this procedure.

Scheme 4. Use of a reducing agent to activate the higher oxidation state catalyst

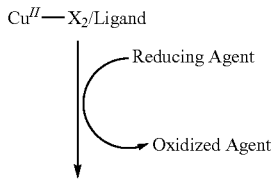

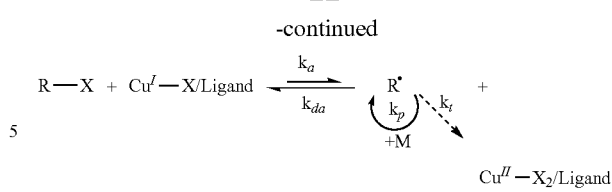

Figure 5A:
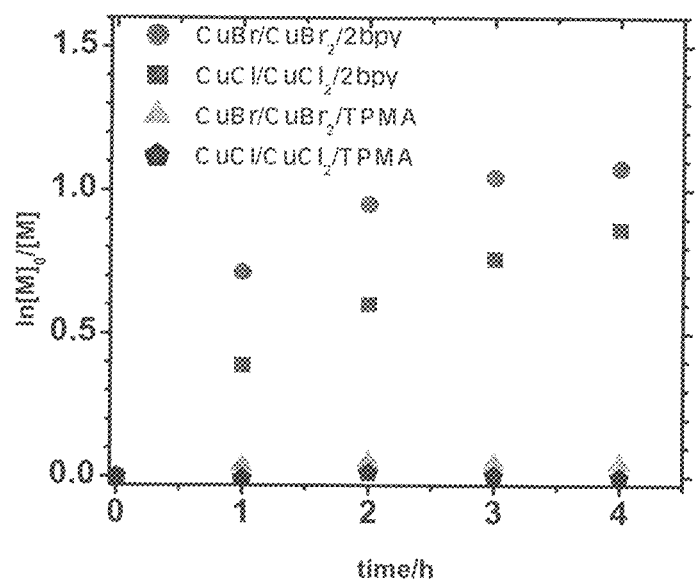
FIG. 5(A): Effect of ligand (L=bpy or TPMA) and halide (X=Br or Cl) on ATRP of OEOMA$_{475}$ grafted from BSA-O-[iBBr]$_{30}$ at 30° C. (Table 1). First order kinetic plot.
Figure 5B:
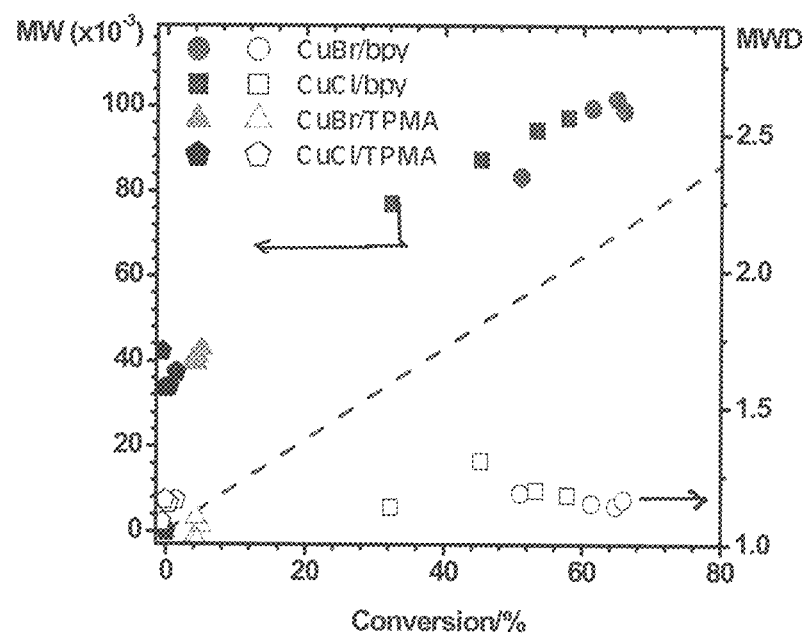
FIG. 5(B): Effect of ligand (L=bpy or TPMA) and halide (X=Br or Cl) on ATRP of OEOMA$_{475}$ grafted from BSA-O-[iBBr]$_{30}$ at 30° C. (Table 1). $M_n$ (solid shapes) and $M_w/M_n$ (open shapes) versus conversion plot.

This AGET method allows for simple targeting of a pre-determined [Cu(I)]/[Cu(II)] ratio by controlling the amount of reducing agent added to the first reaction mixture. The targeted ratio was initially selected to be 2:98. Once again Bpy and TPMA were selected as exemplary ligands. The amount of AA used in this series of reactions was only 1% compared to the total concentration of $CuBr_2$. FIG. 5(A) shows the first-order kinetic plot, whereas FIG. 5(B) gives the $M_n$ and $M_w/M_n$ values for both ligands. The Bpy catalyzed system provided good control over the polymerization as illustrated by the linear first order kinetic behavior. Whereas the TPMA based system resulted in a rapid polymerization in the early stage of the reaction, and no increase in conversion or molecular weight after ~15% conversion, compare Runs 1 and 2 in Table 2. This is in contrast to the linear semi-logarithmic plot observed with the Bpy complex. This rapid termination of the reaction indicates complete reconversion of the small amounts of reactive Cu(I) species generated by reaction of AA with the added Cu(II) to Cu(II), concurrent with radical termination in the presence of high concentrations of radicals generated by a very active catalyst and hence would indicate the TPMA ligand generates an unsuitable catalyst for the reaction.

However, one surprising but very interesting feature in the results reported in Table 2, run 2, and additionally, retrospectively, observed for the TPMA runs reported in Table 1, is that the polymer synthesized using the TPMA based complex had a very narrow molecular weight distribution ($M_w/M_n$=1.09). Therefore rather than immediately abandoning TPMA as a potential ligand, the amount of ascorbic acid added to the reaction was reduced by a factor of ten, Run 3. This did provided a slower reaction but the reaction still stopped at low conversion.

Addition of further amounts of ascorbic acid reactivated the catalyst and allowed the reaction to continue for a short period, Run 4, but overall conversion was still low even after three sequential additions of reducing agent. Despite these difficulties the TMPA system generated polymers that showed lower values for $M_w/M_n$, and the molecular weight was a closer match to the theoretical values than the polymers formed with the Bpy system in the first stages of the reaction.

TABLE 2

Experimental conditions of AGET ATRP from PEO-iBBr and BSA-O-[iBBr]$_{30}$

| Run | M/I/CuBr$_2$/L/AA | I | L | Time/h | Conv./% | $M_{n,theo} \times 10^{-3}$ | $M_{n,GPC} \times 10^{-3}$ | $M_w/M_n$ |
|---|---|---|---|---|---|---|---|---|
| 1 | 455/1/10/22/0.1 | PEO | bpy | 6 | 20 | 43 | 25 | 1.30 |
| 2 | 455/1/10/11/0.1 | PEO | TPMA | 6 | 15 | 32 | 30 | 1.09 |
| 3 | 455/1/10/11/0.01 | PEO | TPMA | 6 | 5 | 11 | 15 | 1.09 |
| 4 | 455/1/10/11/0.03$^a$ | PEO | TPMA | 1 | 12 | 26 | 27 | 1.10 |
| 5 | 227/1/10/11/0.2$^b$ | PEO | TPMA | 4 | 60 | 65 | 37 | 1.09 |

TABLE 2-continued

Experimental conditions of AGET ATRP from PEO-iBBr and BSA-O-[iBBr]$_{30}$

| Run | M/I/CuBr$_2$/L/AA | I | L | Time/h | Conv./% | M$_{n,theo}$ × 10$^{-3}$ | M$_{n,GPC}$ × 10$^{-3}$ | M$_w$/M$_n$ |
|---|---|---|---|---|---|---|---|---|
| 6 | 227/1/10/11/0.1 | BSA | TPMA | 4 | 5 | 5 | 30 | 1.10 |
| 7 | 227/1/10/11/0.1$^c$ | BSA | TPMA | 4 | 88 | 95 | 82 | 1.08 |

Figure 6A:
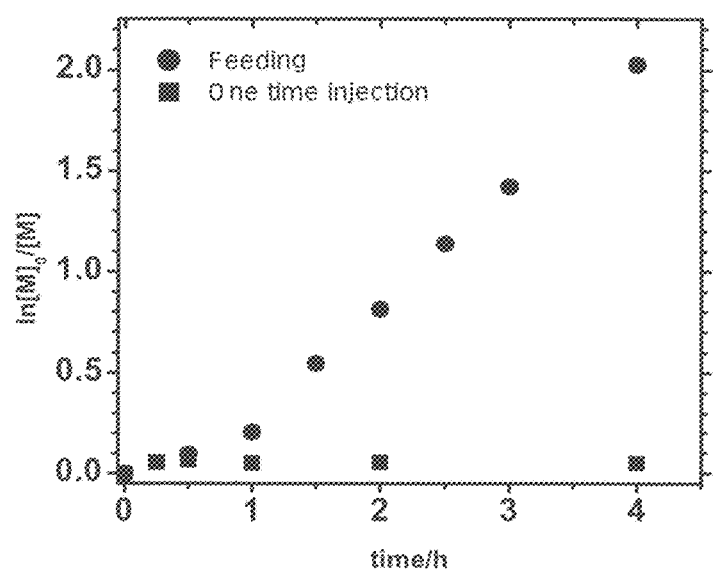
FIG. 6(A): Effect of feeding reducing agent on AGET ATRP of OEOMA$_{475}$ GF BSA-O-[iBBr]$_{30}$ at 30° C. (Reactions 6-7, Table 2). First order kinetic plot.
Figure 6B:
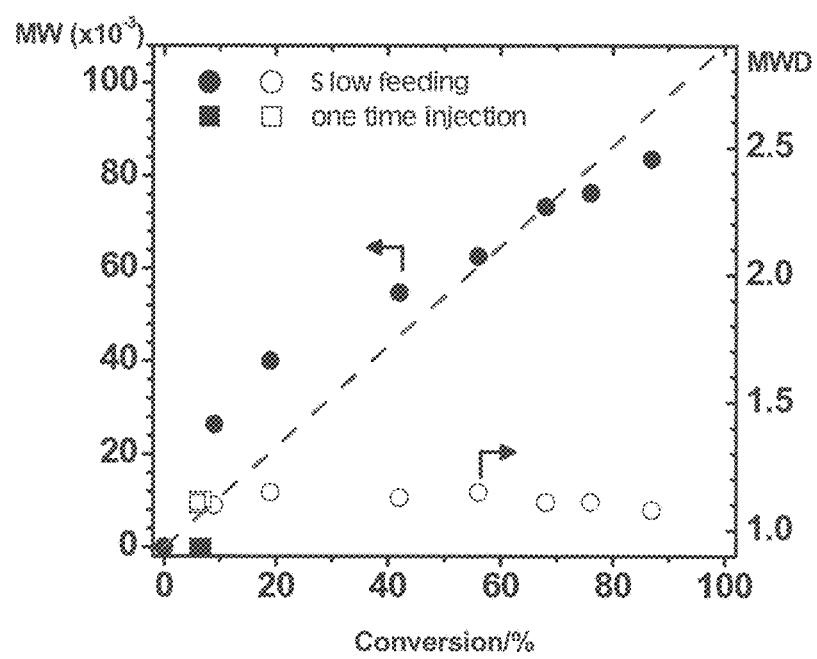
FIG. 6(B): Effect of feeding reducing agent on AGET ATRP of OEOMA$_{475}$ GF BSA-O-[iBBr]$_{30}$ at 30° C. (Reactions 6-7, Table 2). $M_n$ (solid shapes) and $M_w/M_n$ (open shapes) versus conversion plot.

1 mM initiator, 10-20% monomer (v/v), water, 30° C.;
$^a$charges of AA were 0.1 mL of a 0.5 mM solution,
$^b$AA was slowly fed to the reaction mixture at the rate 16 nmol/min,
$^c$AA was slowly fed to the reaction mixture at the rate 8 nmol/min Surprisingly, we concluded that even with the ratio of activator to deactivator set at 2:98 these results did not mean TPMA catalysts are unsuitable for aqueous based ATRP reactions but indicated the need for additional work directed at development of a procedure that would generate an even higher ratio of Cu$^{II}$/Cu$^I$ in systems with TPMA as ligand to provide a sufficient level of deactivator in aqueous media. It was not until ascorbic acid was continuously added to the polymerization, Run 5, ensuring a slow continuous generation of Cu$^I$/L that it was possible to drive the reaction to higher conversion while retaining low M$_w$/M$_n$. FIG. 6(A) and FIG. 6(B) illustrate that slow addition of an identical amount of AA led to 88% conversion in 4 h, compared to 5% conversion when a conventional AGET ATRP was conducted with a single addition of reducing agent to activate a fraction of the catalyst and initiate the reaction. The resulting polymer had a high molecular weight and very narrow molecular weight distribution, 1.08.

Every molecule of ascorbic acid that reacts during the redox reactions provides two electrons. In this reaction the rate of feeding of AA was 8 nano-mol/min, which means that only 0.008% of the total CuBr$_2$ is reduced to Cu(I) every minute and that after 4 hours only 2% of the total amount of CuBr$_2$ in the reaction medium was reduced to form an activator complex. This would indicate that the concentration of the activator, the Cu(I) catalyst complex was lower than 1% throughout the reaction, indeed FIG. 6(A) and FIG. 6(B) show almost immediate initiation of the controlled polymerization reaction, which is truly surprising when one considers that after 30 minutes only 0.025% of the Cu(II) catalyst complex could have been reduced to the activator state but surprisingly this was sufficient to provide an active controlled polymerization in predominantly aqueous media.

An alternative approach would be to use a poorly soluble reducing agent and use the slow solubility or limited access of the copper complex to the solid reducing agent to provide a controlled rate of reduction.

Even with the success detailed above since the concentration of the catalyst complex was higher than desired for a more environmentally benign procedure for a grafting from a protein procedure a systematic evaluation of all components present in the reaction medium for an ARGET ATRP procedure was undertaken. The results of the studies discussed below provided a final resolution of the problems associated with conducting a controlled aqueous polymerization with an active TPMA catalyst whose activity was enhanced by the aqueous medium to such an extent that a controlled polymerization could not be conducted under known ATRP procedures and show how the problem can be resolved.

When a low concentration of catalyst is added, lower than the expected amount of deactivator formed by termination reactions, the reducing agent is utilized to first activate the catalyst complex then continuously reactivate the catalyst. The procedure was named ARGET for activator regenerated by electron transfer, see Scheme 5.

Scheme 5. Use of a reducing agent to continuously reactivate the fraction of the deactivator formed by termination reactions.

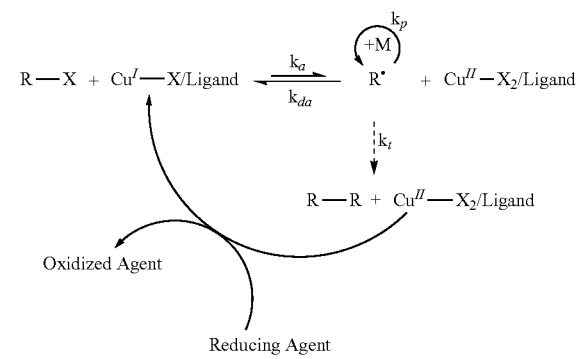

In an ARGET ATRP, Scheme 5, where low ppm concentrations of catalyst are employed, the nature and amount of the reducing agent added to the reaction is critical in order to provide the appropriate ratio [Cu$^{II}$]/[reducing agent] and create conditions for an ATRP that provides good results in terms of both control, rate of polymerization and DP.

Furthermore the influence of halide species, the concentration of the halide in the reaction medium, the ratio of catalyst complexes with different oxidation states of the added transition metal exemplified herein by copper, the selected ligand, the concentration of ligand and the reducing agent all interact together have to be controlled to provide a procedure for the polymerization of water soluble monomers.

Each of these parameters were examined by conducting controlled polymerizations of oligo(ethylene oxide) methyl ether methacrylate as discussed in the examples section. Conditions were developed for the aqueous ARGET ATRP of OEOMA$_{475}$ to prepare well defined polymers at ambient temperature (30° C.) using catalyst concentrations between 100-300 ppm.

Figure 7A:
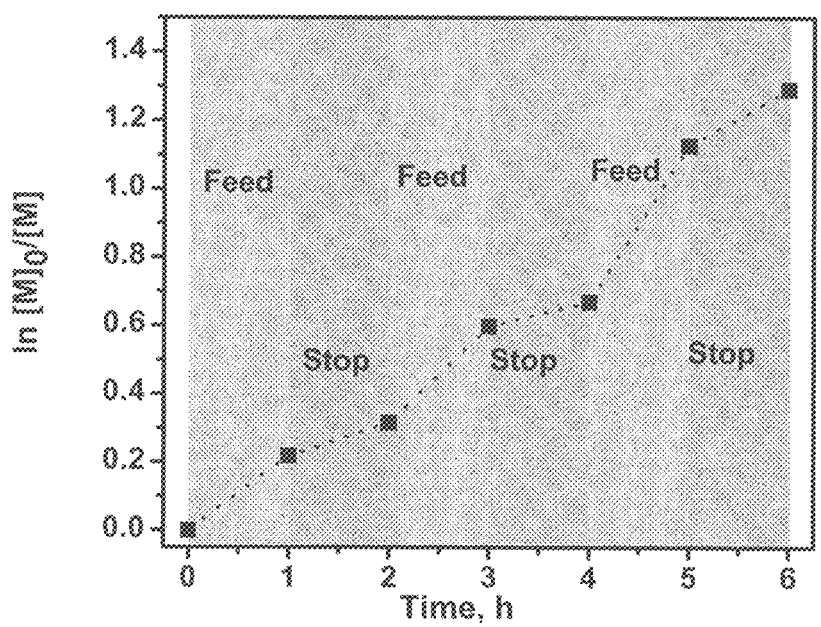
FIG. 7(A): Effect of the feeding rate of ascorbic acid (FR$_{AA}$) on the ARGET ATRP of OEOMA$_{475}$ in water at 30° C. First-order kinetic plot.
Figure 7B:
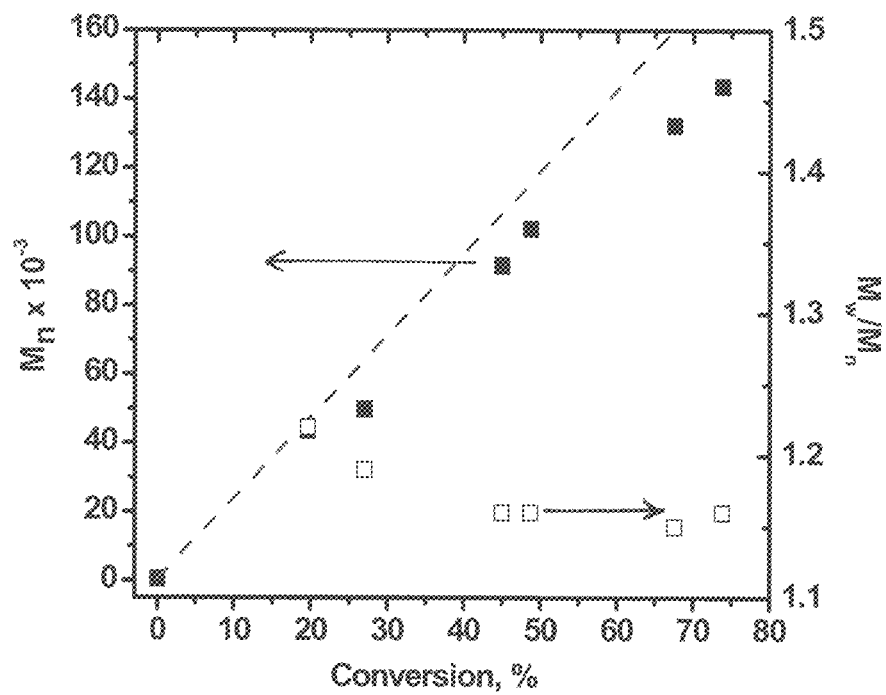
FIG. 7(B): evolution of molecular weight $M_n$ (solid shapes) and molecular weight distribution $M_w/M_n$ (open shapes) with conversion. [OEOMA475]$_0$=0.5 M; [OEOMA475]/[I]/[TPMA]/[CuBr$_2$]=500/1/1.2 /0.15.

Primary issues for preparation of well-controlled polymers are the recognition that the reducing agent, exemplified herein by ascorbic acid, should be slowly fed to the reaction medium and that a large excess of halide salt should be added to the polymerization medium to ensure the presence of a sufficiently high concentration of the deactivator complex. For example, polymerizations with chloride ions showed a slower rate of reaction with improved control compared to bromide ions, with the optimal concentration of the halide salt in the polymerization medium being between 30 and 100 mM. An excess of the ligand over copper is recommended to provide conditions for improved control and faster kinetics. A faster feeding rate of the reducing agent only gives a minimal improvement in the kinetics and leads to a decrease in the level of control over the final polymer. Since the exemplifying ascorbic acid reducing agent should be slowly and continuously fed into the aqueous ARGET ATRP system this generates an additional method of control over the reaction; allowing the reaction to be stopped or restarted at any point simply by ceasing or recommencing the feeding of the reducing agent, FIG. 7(A) and FIG. 7(B).

The low catalyst concentration employed in this aqueous ARGET ATRP make the procedure biologically friendly and hence an excellent technique for creating bioconjugates, as was demonstrated by the synthesis of a BSA based protein-polymer hybrid.

One additional issue related to ATRP for specific bioconjugation applications is exemplified by the fact that there are several bio-compatible monomers, e.g. doxorubicin-methacrylate or $MEO_2MA$, that are not soluble in a pure aqueous system. For this reason polymerizations were performed with addition of 10% (v/v) of an organic solvent. As noted above, an additional approach to incorporate less soluble comonomers into the grafted from (co)polymer chain(s) is to slowly add the less soluble monomer to the reaction medium. Dimethylsulfoxide (DMSO) was chosen as an exemplary co-solvent due to its usefulness in the proteomics research field, and the fact that DMSO at 10% (v/v) does not cause protein's denaturation [*Biophys. Chem.* 2007, 131, 62].

Figure 8A:
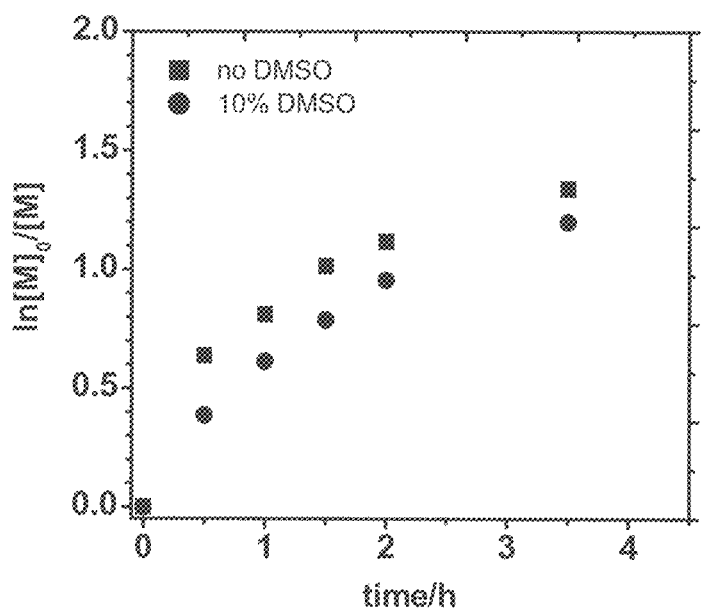
FIG. 8(A): First order kinetic plots. Squares indicate the results from an experiment with no DMSO and 10% of monomer. Circles indicate results from a mixture of 10% monomer and 10% DMSO. Conversion determined by NMR of methacrylate peak vs. 0.5% (v/v) DMF internal standard.
Figure 8B:
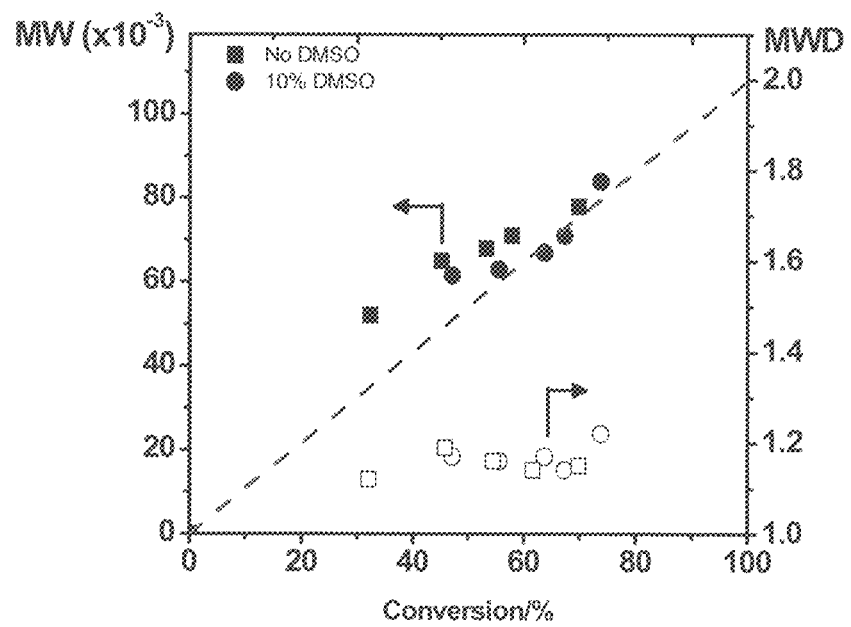
FIG. 8(B): $M_n$ (solid shapes) and $M_w/M_n$ (open shapes) versus conversion plot.

The reaction conditions for polymerizations conducted in the presence of a solvent are summarized in the Table 3. Conversion of monomer followed first-order kinetic plots and the GPC of polymer samples taken periodically throughout the reaction displayed a continuous increase in molecular weight with conversion and narrow molecular weight distribution. As shown in FIG. 8(A) the rate of polymerization was essentially the same with or without DMSO. FIG. 8(B) shows that the molecular weight and polydispersity of the polymers formed in the reactions were also similar for both sets of conditions.

The final set of conditions studied was the optimization of the "grafting from" reaction under buffered conditions. Phosphate buffer saline (PBS) (pH=7.4) is a widely utilized protein buffer and was chosen as a suitable buffer for use in the reaction media for the "grafting from" reactions. Conducting an ATRP in PBS can be challenging for several reasons. Firstly, the copper and phosphate ions can form insoluble $Cu_3PO_4$ causing loss of active species and consequently retardation of polymerization. Secondly, chloride ions from the buffer can displace the ligands from the copper complex, and produce an inactive catalyst. However, as disclosed herein under appropriate conditions these two potential negative effects can be minimized, and a well controlled polymerization can be performed in the presence of PBS. To determine optimized conditions, $OEOMA_{475}$ was polymerized in PBS using both normal ATRP and AGET ATRP processes. Experimental conditions and polymer characteristics are presented in Table 4.

The PEO-iBBr model system showed that the $CuCl/CuCl_2$ catalyzed polymerization reached only 6% monomer conversion after four hours and was therefore not extended to "grafting from" $BSA-O-[iBBr]_{30}$. The $CuBr/CuBr_2$ catalyzed polymerization in PBS was approximately 3 times slower than the reaction in a purely aqueous system, but rather surprisingly the PBS still allowed good control over the polymerization. Therefore, the CuBr/bpy system was used for a traditional ATRP in buffered media from a protein. The polymers grown from $BSA-O-[iBBr]_{30}$ had relatively narrow molecular weight distributions, but as seen in the PEO-iBBr reaction the semilogarithmic plot became noticeably curved after the first hour.

TABLE 3

Experimental conditions for a normal ATRP from $BSA-O-[iBBr]_{30}$ in water/DMSO

| Run | M/I/CuCl/CuCl$_2$/bpy | Time, h | Conv. % | $M_n^{theo} \times 10^{-3}$ | $M_n^{GPC} \times 10^{-3}$ | $M_w/M_n$ |
|---|---|---|---|---|---|---|
| 1 | 455$^a$/1/1/9/22 | 3.5 | 75 | 81 | 80 | 1.22 |
| 2 | 200$^b$/1/1/9/11 | 3.5 | 82 | 40 | 58 | 1.22 |

1 mM initiator, 10% monomer (v/v), 30° C.;
$^a$M = $OEOMA_{475}$,
$^b$M = $[OEOMA_{300}]/[MEO_2MA]$ = 1/1

TABLE 4

Experimental conditions of (AGET) ATRP from PEO-iBBr and BSA-O-[iBBr]$_{30}$

| Run | M/I/CuX/CuX$_2$/L/AA | I | L | X | Time/h | Conv./% | $M_{n,theo} \times 10^{-3}$ | $M_{n,GPC} \times 10^{-3}$ | $M_w/M_n$ |
|---|---|---|---|---|---|---|---|---|---|
| 1 | 227/1/1/9/22/— | PEO | bpy | Cl | 3 | 6 | 6 | 10 | 1.19 |
| 2 | 227/1/1/9/22/— | PEO | bpy | Br | 3 | 33 | 36 | 28 | 1.19 |
| 3 | 227/1/1/9/22/— | BSA | bpy | Br | 3 | 40 | 43 | 50 | 1.26 |
| 4 | 227/1/—/10/11/0.2$^a$ | PEO | TPMA | Br | 4 | 60 | 65 | 37 | 1.09 |
| 5 | 227/1/—/10/11/0.1$^b$ | BSA | TPMA | Br | 4 | 75 | 81 | 83 | 1.19 |

1 mM initiator, 10% monomer (v/v), PBS, 30° C.;
$^a$AA was fed to the reaction mixture at the rate 16 nmol/min;
$^b$AA was fed to the reaction mixture at the rate 8 nmol/min When AGET ATRP, conducted with TPMA as ligand with slow feeding of AA, Runs 4 and 5 in Table 4, there is a linear increase in the first-order kinetic plot up to moderately high monomer conversion which illustrates that low [$Cu^I$] AGET ATRP provides a linear increase in molecular weight with conversion and narrow molecular weight distribution, $M_w/M_n$<1.2. These results demonstrate that well-defined PPHs can be synthesized in the presence of PBS using either a traditional ATRP or an AGET ATRP, however, at the expense of slower polymerization rates as compared to a pure aqueous media and absence of buffer.

In summary, well-defined polymers can be grafted from proteins by ATRP under biologically compatible conditions. These conditions were selected both to maintain protein stability throughout the polymerization and grow well-defined polymers with normal narrow molecular weight distributions so that the PPCs would act in the same manner in bio-applications.

Biologically compatible conditions have been defined as a polymerization conducted at near ambient temperatures (30° C.) with a low initiator concentration (1 mM), low monomer and co-solvent concentrations; i.e., total organic content should not exceed 20% of the total reaction volume. Furthermore, the ligand selected ought to bind to the copper sufficiently strongly to prevent protein denaturation. A CuX/CuX$_2$/Bpy (1/9/22) catalyst complex where X is either Cl or Br was found to be the optimal catalyst when conducting traditional ATRP, FIG. 3(A) and FIG. 4(B). The optimal halide depends upon the reaction media selected: in pure water the chloride species is preferred while in the presence of PBS the bromide species can maintain an acceptable polymerization rate.

ARGET ATRP with slow continuous feeding of a water soluble reducing agent exemplified herein by ascorbic acid (AA) allows the strongly activating TPMA based catalysts to be used, giving controlled polymerization, even with a very low ratio of copper(I) to copper(II) species, less than 1% Cu(I). Moreover, ARGET ATRP with slow feeding of reducing agent gives a rapid reaction and well-controlled polymers in both pure water and PBS.

Finally, the use of 10% of an organic solvent, exemplified herein by DMSO, expands range of available monomers, giving access to smart bio-hybrid materials comprising a broader selection of (co)monomers that are not soluble in pure water. These results show that under the specified conditions, uniform well-defined PPHs can be prepared by ATRP in aqueous media under biologically compatible conditions.

using 100 mM tetraethylammonium bromide (TEABr) to promote the formation of the deactivator. Although the acrylate-Br bond could hydrolyze, this reaction is limited by the presence of TEABr and the results indicate that loss of active chain end is insignificant in these systems or else the PDI would be broader, not ~1.15-1.2 obtained in the reactions. Furthermore one would expect to discern unusual features in the GPC, such as a large population of dead chains and a very fast growing living peak and when starting from the H-EBiB initiator no such effects were observed. There was a linear increase in molecular weight with conversion with no sign of creation of a population which was not capable of chain extension indicating that while the C—Br bond on the chain end can hydrolyze this did not occur to any significant extent at the reaction/temperatures/conditions selected over the time scale of the reaction.

A more recent advance in ATRP is the development of electrochemically mediated ATRP (eATRP) [see International application PCT/US11/65578 herein incorporated by reference]. This procedure also provides a means to continuously control the ratio of Cu(I) species to Cu(II) in an ongoing ATRP process. In an eATRP the application of a cathodic current in an electrochemical cell reduces the Cu(II) complex to a targeted degree and maintains the selected ratio throughout the reaction or until the charge is changed to create a different ratio. The overall mechanism of an eATRP is depicted in Scheme 6.

Scheme 6: Procedure for controlling k$_{ATRP}$ by applied electrical potential

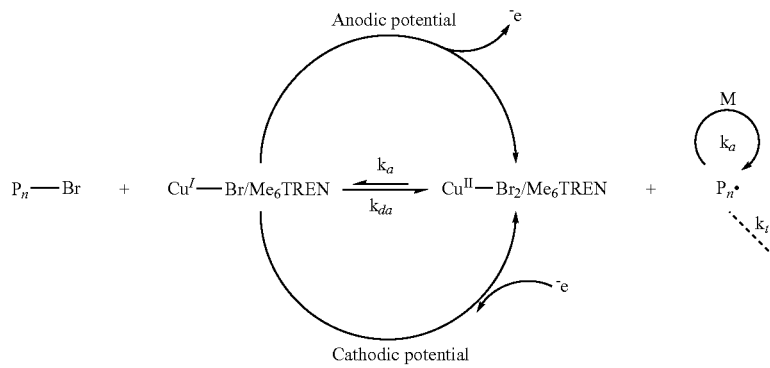

In order to further expand the scope of conducting an ATRP under biologically compatible conditions two other approaches to activating an ATRP reaction were evaluated.

In an ICAR ATRP a low concentration of the Cu(II)X$_2$/L complex is added to the reaction medium and a fraction of the added complex is reduced to the Cu(I)X/L activator state by reaction with a standard free radical initiator. Scheme 4 also illustrates ICAR ATRP if one considers that the formed radicals react with the Cu(II)X$_2$/L complex and reduce a fraction of the higher oxidation state transition metal complex to the activating Cu(I)X/L complex. The rate of initial reduction, and continued reduction throughout the reaction, is controlled by selection of the free radical polymerization (FRP) initiator(s), reaction temperature and concentration of FRP initiators added. Experiments were performed under ICAR conditions, in water with 100 ppm Cu/TPMA catalyst or less, down to 20 ppm. The key premise examined in this set of examples is that control can be obtained under conditions providing low catalyst concentrations in water In an eATRP the reaction mixture initially contains monomer, initiator, and Cu$^{II}$L$^{2+}$ (or Cu$^{II}$L$^{2+}$X—Cu$^{II}$L$^+$). No polymerization occurs under these conditions, as there is no Cu$^I$L$^+$ activator in solution. The reaction starts only when a specific selected potential (E$_{app}$) is applied to the cathode so that reduction of Cu$^{II}$L$^{2+}$ to Cu$^I$L$^+$ occurs at the electrode. The value of E$_{app}$ can be appropriately chosen to achieve a continuous production of a small quantity of Cu$^I$L$^+$ and consequently control the concentration of R$^•$ generated and maintained throughout the reaction. The livingness of the polymerization process is ensured by the intelligent combination of low [R$^•$] and, as disclosed herein, very high ratio of [Cu$^{II}$L$^{2+}$]/[Cu$^I$L$^+$] when targeting aqueous systems with high concentrations of water. The overall rate of the process and the degree of control over polymerization can be tuned by adjusting E$_{app}$. The first example of ATRP under eATRP conditions has recently been reported for the successful polymerization of methyl acrylate in acetonitrile. [*Science* 2011, 332, 81-84.]

Figure 9A:
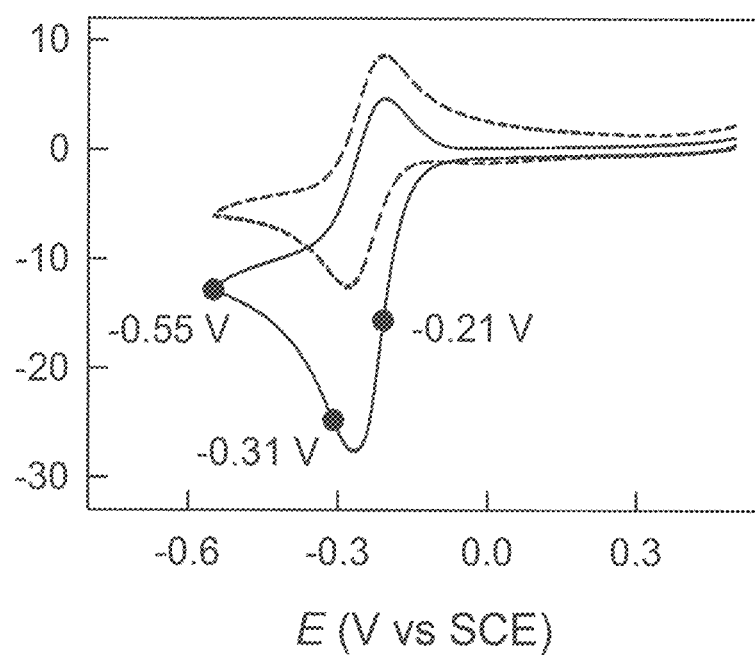
FIG. 9(A): Voltammetric analyses and selected voltages.

Herein, we describe the eATRP of oligo(ethylene glycol) methyl ether methacrylate (OEOMA$_{475}$) in water. Cu$^{II/I}$TPMA, which is one of the most active complexes used in ATRP, was selected for the catalyst system. In cyclic voltammetry (CV) Cu$^{II}$L$^{2+}$ exhibits a reversible peak couple with E$^{\Theta\prime}$=−0.245 V vs SCE, FIG. 9(A). Addition of a large excess of Br$^-$ to the solution does not significantly affect this CV response, indicating that the K$_X$ of Cu$^{II}$L$^{2+}$ is very small. The full reversibility of the response at very low scan rates also points out that Cu$^I$L$^+$ is quite stable in H$_2$O with a lifetime of at least few seconds, the time scale of running a CV. Using the above reported E$^{\Theta\prime}$ value together with other available thermodynamic data, we estimated a K$_D$ value of 6.8×10$^{-3}$ for the disproportionation of Cu$^I$L$^+$. The CV response of Cu$^{II}$L$^{2+}$ drastically changes when an equimolar amount of the initiator 2-hydroxyethyl 2-bromoisobutyrate, (HEBriB) is added. The cathodic peak approximately doubles in height while the anodic one decreases indicating that Cu$^I$L$^+$ rapidly reacts with HEBriB. On the basis of thermodynamic data available in the literature, we estimated a K$_{ATRP}$ value of 1.5×10$^{-1}$ for this system which is 4 orders of magnitude higher than the value measured for an analogous system in CH$_3$CN. An estimate of the activation rate constant based on voltammetric analysis of the system Cu$^{II}$L$^{2+}$+HEBriB at different concentration ratios FIG. 9(B) and different scan rates provides a very large value for k$_{act}$≥2.5×10$^6$ M$^{-1}$s$^{-1}$.

The above described voltammetric analyses confirm that the system under investigation has all the characteristics; low K$_X$, high K$_{ATRP}$, and extremely rapid activation that make aqueous ATRP very difficult to control. The electrogeneration of the active catalyst was first carried out under potentiostatic conditions starting from an aqueous reaction medium containing Cu$^{II}$L$^{2+}$/HEBriB 1:1 in H$_2$O+10% OEOMA$_{475}$ (MW=475 g/mol). The effect of E$_{app}$ on the degree of control over polymerization was initially investigated. Three E$_{app}$ values around E$^{\Theta\prime}$, see FIG. 9(A) and FIG. 9(B), were applied and the results are summarized in Table 5, Runs 1-3.

The driving force of the electrochemical process is given by ΔG$^\Theta$=F(E$_{app}$−E$^{\Theta\prime}$) and the [Cu$^{II}$L$^{2+}$]/[Cu$^I$L$^+$] ratio at the electrode surface is closely related to that dictated by the Nernst equation. At the beginning of the electrolysis there is only Cu$^{II}$L$^{2+}$ in solution, so the current has to decay as Cu$^{II}$ is converted to Cu$^I$, approaching a constant value corresponding to the [Cu$^{II}$L$^{2+}$]/[Cu$^I$L$^+$] ratio generated by the applied E$_{app}$. However, Cu$^I$L$^+$ is engaged in a reversible reaction with the initiator, and dormant species, which represents a continuous perturbation to the equilibrium concentrations imposed by E$_{app}$. Therefore, whether a constant [Cu$^{II}$L$^{2+}$]/[Cu$^I$L$^+$] ratio can be imposed in the bulk solution depends on the mutual rates of electrogeneration and disappearance of Cu$^I$L$^+$ and therefore will depend on E$_{app}$. At E$_{app}$=−0.55 V, which is ≪E$^{\Theta\prime}$, the electrode process is under diffusion control and Cu$^{II}$L$^{2+}$ is almost quantitatively converted to Cu$^I$L$^+$ in a relatively short time; the current rapidly decreases to very small values. The overall rate of the process was rather high, with 79% of monomer conversion in less than 30 min, but control over polymerization was poor. The ln([M]/[M]$_0$) vs. time plot deviated significantly from linearity, while M$_w$/M$_n$ was very broad and the final experimental M$_n$ was 3 times larger than theoretical, Table 5, Run 1. These features are typical of an uncontrolled polymerization dominated by termination reactions, such as bimolecular radical-radical coupling.

TABLE 5

Electrochemical aqueous ATRP of OEOMA475 at 25° C.

| Run | % M v/v | [M]/[RX]/[Cu$^{II}$L] | Electrolyte[c] | E$_{app}$ (V vs SCE) | t (h) | Q (C) | C %[e] | 10$^{-3}$ M$_{n,theor}$ | 10$^{-3}$ M$_{n,exp}$[f] | M$_w$/M$_n$ |
|---|---|---|---|---|---|---|---|---|---|---|
| 1 | 10 | 200/1/1[a] | Et$_4$NBF$_4$ | −0.550 | 0.5 | 3.05 | 79 | 75.1 | 233 | 1.58 |
| 2 | 10 | 200/1/1[a] | Et$_4$NBF$_4$ | −0.310 | 1.8 | 4.34 | 88 | 83.2 | 213 | 1.53 |
| 3 | 10 | 200/1/1[a] | Et$_4$NBF$_4$ | −0.210 | 3.0 | 2.65 | 98 | 93.1 | 112 | 1.22 |
| 4 | 10 | 200/1/1[a] | Et$_4$NBr | −0.210 | 2.5 | 2.32 | 99 | 94.0 | 109 | 1.16 |
| 5 | 10 | 200/1/1[a] | PBS buffer[d] | −0.275 | 3.0 | 1.94 | 98 | 93.1 | 130 | 1.15 |
| 6 | 5.0 | 1000/1/1[b] | Et$_4$NBr | −0.210 | 2.0 | 0.175 | 84 | 399 | 704 | 1.25 |
| 7 | 2.5 | 500/1/1[b] | Et$_4$NBr | −0.210 | 2.0 | 0.210 | 72 | 171 | 403 | 1.19 |
| 8 | 1.0 | 200/1/1[b] | Et$_4$NBr | −0.210 | 2.5 | 0.267 | 77 | 73.2 | 175 | 1.35 |
| 9 | 5.0 | 1000/1/1[b] | PBS buffer[d] | −0.275 | 2.0 | 0.179 | 79 | 375 | 450 | 1.20 |

[a][Cu$^{II}$L$^{2+}$] = 1 mM.
[b][Cu$^{II}$L$^{2+}$] = 0.1 mM.
[c]0.1M.
[d]0.137M NaCl + 2.7 mM KCl + 11.9 mM (Na$_2$(HPO$_4$) + KH$_2$PO$_4$) in H$_2$O; pH = 7.4.
[e]Determined by $^1$H NMR.
[f]Determined by GPC-MALLS In order to promote the formation of X̃Cu$^{II}$L$^+$ some experiments were run in the presence of a large excess of X$^-$, Table 5, runs 4-5. The presence of X$^-$ produces a discernible improvement of MW distribution without any reduction in rate of monomer conversion. Contrary to expectations the overall rate of the process does not decrease due to the formation of inactive Cu$^I$X$_n$ species as was found in organic solvents [*Macromolecules*, 2010, 42, 9257-9267, *Chem. Commun.* 2011, 47, 3580-3582].

The possibility of carrying out polymerizations under biologically compatible conditions was investigated using PBS buffer as the solvent. Since E$^{\Theta\prime}$ shifts to −0.326 in this medium E$_{app}$ was adjusted to −0.275 V. Although several side reactions perturbing the ATRP equilibrium are possible; e.g., formation of highly insoluble Cu$^{II}$$_3$(PO$_4$)$_2$ and/or stable Cu$^I$(H$_2$PO$_4$)$_2$$^-$ and Cu$^I$Cl$_2$$^-$, excellent results were observed both in terms of conversion and M$_w$/M$_n$, Table 5, Run 5. Indeed, neither displacement of the ligand nor loss of catalytic activity was observed by CV analysis of the system.

Finally the ability to target different DPs were explored, Table 5, Runs 6-8, using 0.1 mM Cu$^{II}$L$^{2+}$, 6.4 ppm with respect to solvent, and different concentrations of monomer. All polymerizations displayed a linear ln([M]/[M]$_0$) vs. time plots which, together with low values for M$_w$/M$_n$ of the final polymer, is indicative of a well controlled ATRP. However, the experimental M$_n$ was significantly higher than the theoretically predicted one. This was due to low initiation efficiency at the beginning of the polymerization and a significant improvement was obtained after addition of PBS buffer, Table 5, Run 9.

In conclusion, eATRP overcomes the most serious drawbacks associated with conventional aqueous ATRP. The $Cu^{II}L^{2+}$ to $Cu^{I}L^{+}$ ratio, which is key to the successful control of the reaction, can be regulated by appropriate selection of $E_{app}$. The best results were achieved at $E_{app}>E^{0}{}_{Cu(II)L/Cu(I)L}$, providing excellent control over MW and MW distribution, accompanied by a fast reaction and a low charge consumption. Remarkably, phosphates and halide ions are not only tolerated but can have a beneficial effect on the degree of control over the polymerization which can be a positive observation when targeting biological systems.

These experiments, reported in detail below, demonstrated that well-controlled polymers can be prepared by ATRP under biologically compatible conditions, provided that appropriate reaction conditions are selected for the selected initiation system.

In the initial examples employing a standard ATRP procedure the copper chloride system resulted in improved polymerization control compared to copper bromide using Bpy ligand for the classic ATRP.

In AGET ATRP it was determined that TPMA provided a catalyst complex that was more active than Bpy when using an identical amount of ascorbic acid as the reducing agent. Upon reducing the amount of ascorbic acid used in ATRP systems with TPMA as the ligand, timed feeding resulted in a slower more controlled polymerization, while maintaining a linear increase of molecular weight with conversion and narrow symmetrical molecular weight distributions.

ARGET ATRP with 300 ppm catalyst complex formed with TPMA in the presence of excess halide salt and slow continuous feeding of reducing agent provided good control over the polymerization.

ICAR ATRP could be conducted with low levels of catalyst, down to 20 ppm.

eATRP was also successfully applied to preparation of a PPC.

In one embodiment of this invention targeting an environmentally benign system for the preparation of PPH the concentration of transition metal in the polymerization medium is less than 1000 ppm, preferably less than 500 ppm and more preferably 300 ppm or less.

The mole fraction of activator to deactivator in the selected ATRP procedure conducted in aqueous systems can be less then 20%, preferable less than 10% and often less than 5% and indeed in specific systems lower than 1%.

Other embodiments of the present embodiment includes a process for the formation of a conjugate between a bioresponsive molecule and a polymer wherein a low concentration of bioresponsive molecule with a site specific functional initiator may be utilized for a transition metal mediated controlled polymerization of vinyl monomers in an aqueous based polymerization medium. In certain embodiments the bio-responsive molecule may comprise a protein, polypeptide, polynucleotide, adaptamer or other biomolecule that is incorporated into the formed conjugate with the polymer grown from the initiator site(s). In specific embodiments, the site specific functional initiator may be a radically transferable atom or group. In certain embodiments, the monomer volume fraction or total organic content may be not greater than 30% of the total content of the reaction medium. In certain embodiments the monomer volume fraction or total organic content may be less than or equal to 20% (v/v) total content of the reaction medium. In certain embodiments, the polymerization reaction may be conducted near ambient temperatures, between 4° C. and 50° C. In certain embodiments, the transition metal catalyst may comprise a transition metal that forms a soluble complex with a ligand wherein the formed complex does not influence the tertiary structure of GFP and thereby reduce the fluorescence of GFP. In certain embodiments, the site specific initiator may comprise a radically transferable atom or group. Certain embodiments may further comprise a buffer added to the aqueous reaction medium. In certain embodiments, the buffer may have the same counterion as the transferable atom or group on the added initiator. According to certain embodiments, the concentration of protein in the reaction may be less than about 3 mg/mL protein concentration and concentration of monomer and organic solvent is no more than 20% (v/v) and the polymerization may be conducted near ambient temperatures in aqueous media. In certain embodiments, the linkage between the bioresponsive molecule and the site specific functional initiator may comprise a cleavable linkage. According to certain embodiments, the bioresponsive molecule may be a protein that retains it structure, topology and activity and the tethered polymers have a normal distribution of molecular weights and provide values for molecular weight distribution lower than 1.30. In certain embodiments, the normal distribution of molecular weights may provide values for molecular weight distribution lower than 1.25 or in other embodiments lower than 1.15. In certain embodiments, the controlled polymerization process may be an ATRP and the ligand for the catalyst complex is selected so that the protein is stable in the presence of the copper halide catalyst complex. In certain embodiments, water is the solvent and the reaction may conducted with less than 1000 ppm, or even less than 500 ppm catalyst complex comprising a strongly coordinating ligand which polymerizes radically (co)polymerizable monomers from a bioresponsive initiator comprising one or more transferable atoms or groups by a grafting from process at ambient temperatures wherein a fraction of the catalyst complex is continuously reduced from the higher oxidation state to a lower oxidation state by controlled addition of a reducing agent. In certain embodiments, the concentration of the added cupric halide catalyst complex may be less than 300 ppm and the reaction may be conducted in the presence of a salt comprising the same halogen as the catalyst complex and initiator and a fraction of the added higher oxidation state deactivator catalyst complex may be reduced to the lower oxidation state activator complex by reaction with either a reducing agent, the continuous degradation of an added free radical initiator or by application of a potentiometric or galvanistic charge to maintain a targeted ratio of $Mt^x$ to $Mt^{x+1}$. In certain embodiments, the concentration of salt is between 10 and 300 mM. In certain embodiments, mole fraction of activator to deactivator in the selected ATRP procedure may be less then 20%, or even less than 10% and often less than 5%, and in specific systems lower than 1%. In certain embodiments, the polymerization process may be an AGET ATRP or ARGET ATRP and the reducing agent may be added intermittently or continuously to the reaction medium to maintain a ratio of Cu(I) to Cu(II) catalyst complex and the process may include forming a polymer-protein conjugate wherein the normal distribution of the polymer portion may have a molecular weight distribution of less than 1.25. In certain embodiments, the reducing agent may be added continuously to the reaction medium and the rate of addition may be slowly reduced as a batch reaction progresses. In certain embodiments, the polymerization may be an ICAR ATRP and the concentration of the added cupric halide catalyst complex may be less than 150 ppm in the presence of a salt comprising the same halogen as the catalyst complex and initiator and a fraction of the catalyst complex may be reduced to the cuprous state by reaction with a continuously degraded added free radical initiator to maintain a ratio of Cu(I) to Cu(II) catalyst complex forming a polymer-protein conjugate wherein the normal molecular weight distribution of the polymer has a distribution of less than 1.35.

Various features of the present invention will become more apparent upon consideration of the following examples. The various embodiments of this disclosure described in the following examples are not to be considered as limiting the invention to their details. All parts and percentages in the examples, as well as throughout this specification, are by weight unless otherwise indicated.

EXAMPLES AND DISCUSSION OF EXAMPLES

Materials. The highest available purity oligo(ethylene oxide) monomethyl ether methacrylate (average molecular weight ~475, ~300, 188 g/mol, $OEOMA_{475}$, $OEOMA_{300}$, $OEOMA_2$ respectively), BSA, mono-tent-butyl succinate, N-hydroxysuccinimide (NHS), trifluoroacetic acid, bromoisobutyryl bromide, 2,2'-bipyridine (Bpy), N-(n-propyl) pyridylmethanimine (PI), ascorbic acid (AA), CuCl, $CuCl_2$, CuBr, and $CuBr_2$ were purchased from Aldrich. Tris(2-pyridylmethyl)amine (TPMA) was purchased from ATRP Solutions. Monomers were passed over a column of basic alumina prior to use. Poly(ethylene oxide)isobutyryl bromide (PEO-iBBr $M_n$=2000) was prepared, as previously described. [*Biomaterials* 2009, 30, 5270] GFP was prepared as previously described. [*Polym. Chem.* 2011, 2, 1476.]

Instrumentation. Molecular weight and molecular weight distribution ($M_w/M_n$) were determined by GPC. The GPC system used a Waters 515 IIPLC Pump and Waters 2414 Refractive Index Detector using PSS columns (Styrogel $10^2$, $10^3$, $10^5$ Å) in dimethylformamide (DMF) as an eluent at a flow rate of 1 mL/min at 50° C. and in tetrahydrofuran (THF) as an eluent at a flow rate of 1 mL/min at 35° C. All samples were filtered over anhydrous magnesium sulfate and neutral alumina prior to analysis. The column system was calibrated with 12 linear polystyrene ($M_n$=376~2,570, 000).

Monomer conversion was measured using $^1$H NMR spectroscopy in $D_2O$, using a Bruker Avance 300 MHz spectrometer at 27° C.

Thermoresponsivity was measured by dynamic light scattering (DLS) on a Zetasizer from Malvern Instruments, Ltd. The temperature ramp used in this study was from 15° C. to 64° C. at 1° C. intervals. Samples were equilibrated for 2 mins before measuring particle size.

Tangential flow filtration was conducted on a Labscale TFF system from Millipore. Zebra Spin desalting columns were purchased from Fisher and used according to the manufactures instructions.

The fluorescence spectra for GFP stability testing were obtained on a Tecan Safire2 using a 96 well plate.

Example 1.

Determination of Suitable Reaction Conditions

A series of ATRP reactions were conducted in order to identify a suitable range of ligands and select reaction conditions for controlled polymerizations under conditions that would not denature a protein or other biologically active molecule. Water soluble initiators and water soluble monomers are employed in these reactions. The target was to determine if a well controlled ATRP could be conducted in the presence of 80% water at room temperature.

DSRC1. Normal ATRP with N-(n-propyl)pyridylmethanimine (PI) Ligand:

$PEO_{2000}iBBr$ (1.58 mg, 0.00079 mmol), $OEO_{475}MA$ (22.5 μL, 0.04977 mmol), were dissolved in 4.5 mL of Millipore water. This solution was degassed for 20 minuets by bubbling with nitrogen. A stock solution of $CuCl_2$ (95.5 mg, 0.71 mmol), with (1.66 mmol) of added ligand was prepared in water (5 mL). When the selected ligand was pyridine imine ligand (245.3 mg, was added), CuCl (7.8 mg, 0.079 mmol) was prepared in 5 mL of water and 500 μL of this solution was added to the initiator and monomer solution to initiate polymerization thereby providing a ratio of reagents=[1]:[63]:[0.1]:[0.9]:[2.1] Samples were periodically drawn to investigate the reaction kinetics. Water was evaporated from the samples before re-suspension in THF. The samples were filtered with a 0.2 micron filter with neutral alumina and 1 drop of toluene. The molecular weight increased linearly with time.

In a series of runs with different ratio of monomer to initiator the MW increased linearly with conversion and GPC traces displayed a normal distribution of molecular weights and provide low values for molecular weight distribution ($M_w/M_n$).

DSRC2. Normal ATRP with Bpy as Ligand:

$PEO_{2000}iBBr$ (10.0 mg 0.005 mmol), $OEOMA_{475}$ (1 mL, 2.28 mmol), $CuBr_2$ (10.0 mg, 0.045 mmol), and Bpy (16.4 mg, 0.105 mmol) were dissolved in 4 mL of water and charged into a 10 mL Schlenk flask. The reaction was bubbled for 20 minutes, frozen, and CuBr (0.72 mg, 0.005 mmol) was added under the flow of nitrogen. The reaction was put under vacuum and back filled with nitrogen 5 times, thawed, and placed in an oil bath at 30° C. Molecular weight increased linearly with conversion and final dispersity was low, 1.16, when the molecular weight reached 57,800.

DSRC3. TPMA was Tested Under the Same Model Conditions:

Ratio of reagents: [L]:Cu[I]:Cu[II]:[I] of 11:1:9:1 the reaction gave multimodal GPC traces indicating a fast reaction with no control.

As can be seen from the data presented above that moderate control has been found for both the Bpy and PI systems. This could be interpreted as indicating lower activity catalysts are preferred but conditions presented above need to be further examined before they can be declared biologically compatible. At this point the major conclusions are a high Cu(II):Cu(I) ratio allows control over the ATRP process.

DSRC4. Effect of Solvent:

DMSO, diglyme and ethanol were evaluated as added solvents. The fraction of solvent and monomer added to 80% water was varied from 0:20 to 10:10 and 17:3. The best results were obtained with 10% DMSO and 10% monomer. Conditions: $PEO_{2000}iBBr$ (10.0 mg 0.005 mmol), $0EO_{475}MA$ (477 μL, 1.055 mmol), Cu(II)$Br_2$ (10.0 mg, 0.045 mmol), and Bpy (16.4 mg, 0.105 mmol) were dissolved in 4000 μL of ultra pure water in a 10 mL Schlenk flask. To this solution 500 μL of DMSO was added. The reaction was bubbled for 20 minutes frozen and Cu(I)Br (0.72 mg, 0.005 mmol) was added under the flow of nitrogen. The reaction was back filled with nitrogen 5 times and the reaction was thawed and placed in an oil bath at 30° C. The reaction was run for 200 minutes and from the GPC traces of samples taken periodically demonstrated that the addition of 10%

DMSO co-solvent allows for well-controlled polymerization. The final sample had an $M_w/M_n$ of 1.25.

DSRC5. AGET ATRP

DSRC5A: Mode of Addition of Reducing Agent:

Initially one reason for examining an AGET system was because in small scale exploratory examples when targeting lower Cu(I) concentrations weighing out of these minute samples becomes practically impossible due to balance accuracy. The total Cu(I) in the system should be kept to a minimum to take into account a repressed deactivation environment presented by high levels of water. Furthermore in addition to single addition, and multiple fractional additions, of the reducing agent the effect of a slow continuous feeding of ascorbic acid into the system was evaluated in order to determine if control is improved.

Initial polymerizations were conducted with $[OEOMA_{475}]=0.45$ M and $[OEOMA_{475}]/[I]/Cu(II)X_2F[AA]=455/1/10/0.1$. [Bpy] and [TPMA]=21 and 11 mM, respectively. The results are presented in Table 2 where it can be observed that continuous addition of small amounts of reducing agent, run 7, provided high conversion and narrow $M_w/M_n$.

DSRC5B. Effect of Ratio of Activator:Deactivator:

In addition to ligand effects, the effect of targeting different ratios of [Cu(I)]:[Cu(II)] was investigated. This ratio is decisive in determining the degree of control attained in ATRP, since it governs the rate of polymerization. The ratio of [Cu(I)]:[Cu(II)] was decreased by a factor of 10 in the TPMA system. Rather than attempting to add an exceedingly small amount of solid Cu(I) an AGET system was employed and operated by adding less reducing agent, to gain control of the polymerization since TPMA is a highly active ligand, implying that even a low concentration of copper(I) species can provide rapid polymerization. Two different reaction conditions were studied. In the first case only one charge of reducing agent was added, targeting an initial ratio of [Cu(I)]:[Cu(II)] of 0.2:9.8. In the second system, there were two additional additions of ascorbic acid, one after 16 min and the other after 32 min. The results are reported in Table 6. The reaction mixture was prepared for the polymerization by passing nitrogen gas through a solution of monomer, initiator, ligand, copper (II) bromide, and water for a minimum of 20 minutes before adding a deoxygenated solution of ascorbic acid under inert conditions. Samples were taken periodically for GPC (0.4 mL). Before GPC analysis the samples were dried over magnesium sulfate. Monomer content was ~20%, or ~10% (v/v) when a solvent was added, and the total volume of the system was 5 mL.

In the first series of reactions; Runs 1, 3, 4 and 6 in Table 6, the ascorbic acid was added in a single injection. The reaction quickly reached a plateau indicating loss of activator due to termination reactions although PDIs were still narrow. In Table 6 Run 10, 50 μl of 1 mM solution of ascorbic acid was added every 15 mins, a 250 μl gas-tight syringe was used for the injection. In other reactions, Table 6 Runs 15-19, a syringe pump was used to continuously add the reducing agent to the reaction. The total moles of ascorbic acid added in Run 10 were calculated and moles per minute were determined (3.3 nmol/min). The syringe pump was set at a speed 1 μl/min of 4 mM solution of ascorbic acid, therefore 4 nmol/min was added. The reactions using the syringe pump for addition of the reducing agent progressed to higher conversions with lower molecular weight distributions. However, for Runs 15 through 18 in Table 6 an increase in polydispersity with higher conversion was observed. This was attributed to the fact that at higher conversions the solutions became very viscous, which can partially be attributed to pulling samples for analysis. Indeed, a total volume was 5 mL and 0.4 mL samples were removed but the speed of feeding of the reducing agent remained the same which means that after some point the effective rate of addition of reducing agent increased and the concentration of ascorbic acid became too high and some crosslinking/coupling was observed. This was avoided when a larger volume of reaction media was employed. Run 19 in Table 6.

TABLE 6

Reactions for system [M]:[I]:[TPMA]:[CuBr$_2$]:[AA]

| Run | Ratio | Solvent | % of monomer | Volume of reaction | Syringe pump | Time, h | Conv. | $M_n$ | PDI |
|---|---|---|---|---|---|---|---|---|---|
| 1 | 455:1:11:9.99:0.1 | water | 20 | 5 mL | no | 1 h# | 12% | 31000 | 1.16 |
| 3 | 455:1:11:9.99:0.01 | water | 20 | 5 mL | no | 0.66 h# | 5% | 15000 | 1.09 |
| 4 | 455:1:11:9.99:0.01 | water | 20 | 5 mL | no* | 1 h# | 12% | 28000 | 1.11 |
| 6 | 455:1:11:9.99:0.1 | PBS | 20 | 5 mL | no | 6 h | 7% | 35000 | 1.12 |
| 10 | 227:1:21:10:0.01 | PBS | 10 | 5 mL | no* | 1.5 h | 28% | 31900 | 1.11 |
| 15 | 455:1:21:10:0.01 | water | 20 | 5 mL | yes | 2.5 h | 59% | 83800 | 1.33 |
| 17 | 227:1:21:10:0.01 | water | 10 | 5 mL | yes | 3 h | 92% | 76400 | 1.20 |
| 18 | 455:1:21:10:0.01 | PBS | 20 | 5 mL | yes | 3 h | 73% | 87300 | 1.21 |
| 19 | 227:1:21:10:0.01 | PBS | 10 | 20 mL | yes | 4 h | 59% | 36700 | 1.09 | reaction self terminated under selected conditions after this time period.
*In Runs 4 and 10 the addition of the ascorbic acid was split into three; one at the beginning, one after 20 min and one after 30 min.

DSRC6. ARGET ATRP

In an ARGET ATRP the concentration of catalyst in the system is significantly lower than in an AGET ATRP and indeed is reduced below that expected to result in conversion of all Cu(I) to Cu(II) due to termination reactions and hence the catalyst has to be regenerated by addition of a reducing agent. This low level of added catalyst exacerbates the problems associated with dilute aqueous polymerization media. Therefore a systematic study of the roles of all agents that could contribute to a controlled reaction were analyzed.

DSRC6A: Influence of Added Counterion:

One of the major challenges associated with aqueous ATRP is the dissociation of the halide anion from the Cu(II) deactivator complex, which both reduces deactivator concentration and affects the dispersity of the final product, Scheme 7. [Tsarevsky, N. V.; Pintauer, T.; Matyjaszewski, K. *Macromolecules* 2004, 37, 9768-9778.] The addition of a halide salt increases the concentration of the $Cu^{II}X/L$ species and promotes efficient deactivation.

Scheme 7. ATRP with dissociation of the halide anion from deactivating complex (A), and equation for calculating the dispersity of the polymer (B).

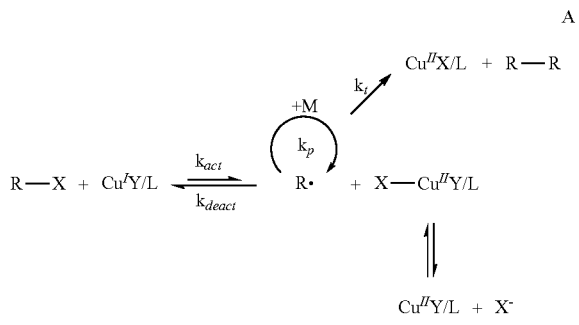

reaction was quite slow under conditions that provided good control. As discussed above, the addition of a halide salt significantly reduced the rate of the reaction and the polymerization reached only 11% conversion in 6h compared to 92% in 5h for a reaction without added TEABr. Therefore, the feeding rate of the ascorbic acid ($FR_{AA}$) was varied from 8 to 32 nmol/min, to determine if the presence of higher amounts of ascorbic acid increased the rate of the controlled polymerization. The results are reported in Table 7. As expected, higher rates of injection of the ascorbic acid reducing agent, ($FA_{AA}$) led to higher rates of polymerization. However, feeding rates of 16 and 32 nmol/min resulted in a significant increase in $M_w/M_n$ at conversions above 50%. This broadening of the dispersity could be due to either a high termination rate or to a poor deactivation rate.

TABLE 7

ARGET ATRP of OEOMA$_{475}$ with varied feeding rate of ascorbic acid ($FR_{AA}$)

| Run | M/I/TPMA/CuBr$_2$ | $FR_{AA}$, nmol/min | Cu$^a$, ppm | Time h | Conv % | $M_{n\,th}{}^b \times 10^{-3}$ | $M_{n\,GPC}{}^c \times 10^{-3}$ | $M_w/M_n$ |
|---|---|---|---|---|---|---|---|---|
| 1 | 500/1/0.1/0.05 | 8 | 100 | 23 | 41 | 98 | 72 | 1.35 |
| 2 | 500/1/0.1/0.05 | 16 | 100 | 23 | 68 | 161 | 104 | 1.66 |
| 3 | 500/1/0.1/0.05 | 32 | 100 | 23 | 67 | 159 | 122 | 1.85 |

All polymerizations were conducted with [M]$_0$ = 0.5M, [I]$_0$ = 1 mM, [TEABr]$_0$ = 100 mM;
$^a$Calculated by the initial molar ration of CuBr$_2$ to the monomer;
$^b$M$_{n\,th}$ = ([M]$_0$/[I]$_0$) × conversion × M$_{monomer}$;
$^c$universal calibration -continued $$\frac{M_w}{M_n} = 1 + \frac{1}{DP_n} + \left(\frac{k_p[RX]_o}{k_{deact}[XCu^{II}/L]}\right)\left(\frac{2}{conv.} - 1\right) \quad B$$

Initial experiments were designed to confirm that the addition of an excess of halide salt improves the level of control over the polymerization in systems with ~80% water in the reaction medium. Polymerizations without and with 100 mM tetraethylammonium bromide (TEABr) were performed. Kinetic plots, molecular weight, dispersity, and GPC traces indicated that in the absence of the added salt, the rate of the reaction was significantly higher than with the salt, but the system without additional halide ions did not follow linear first-order kinetics. The dispersity of the final polymer samples were higher than 1.5, whereas with the addition of extra bromide ions they were lower than 1.4. In addition, the GPC traces showed that polymers synthesized without added TEABr displayed a high molecular weight shoulder, which could be due to termination reactions caused by the higher concentration of radicals. In contrast, when the salt was added, the distributions were monomodal and shifted cleanly towards higher molecular weight confirming that addition of extra halide species does promote more efficient deactivation, probably by increasing the concentration of the deactivator in the aqueous polymerization medium.

DSRC6B: Influence of Rate of Addition of Reducing Agent

Although the preliminary results showed that an ARGET ATRP can proceed in a controlled manner, the rate of the DSRC6C: Influence of Adding Excess Ligand.

Figure 10A:
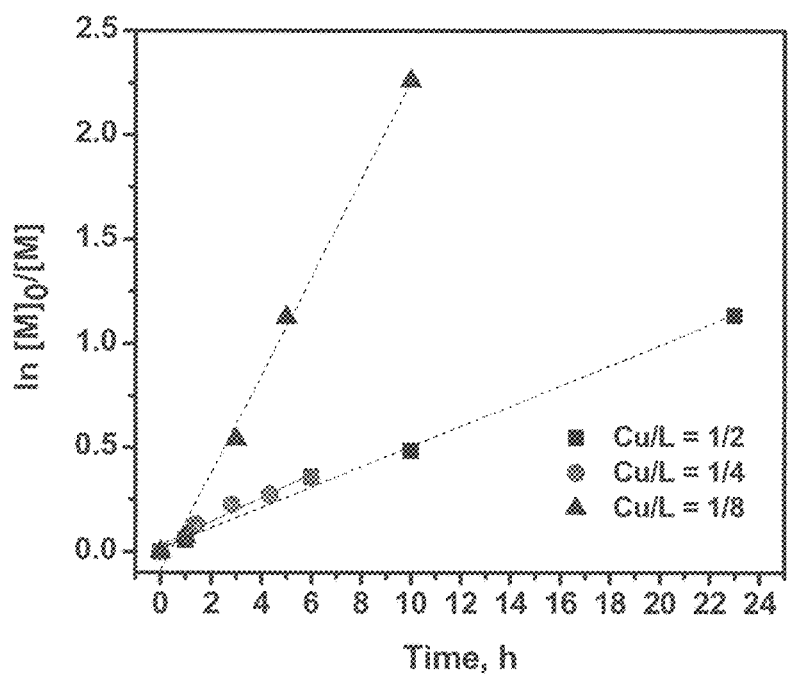
FIG. 10(A): Effect of the ratio of Cu:L on the ARGET ATRP of OEOMA$_{475}$ in water at 30° C. First-order kinetic plot.

It has been reported that the presence of an excess of ligand compared to copper can increase rate of polymerization in an ARGET ATRP [Pintauer, T.; Matyjaszewski, K. Chem. Soc. Rev. 2008, 37, 1087-1097]. Since ARGET ATRP uses low concentrations of catalyst, partial dissociation of the ligand from the metal in the presence of an excess of other reagents can occur and influence the rate of polymerization. Therefore, the addition of an excess of the ligand can increase the concentration of activator and consequently the rate of polymerization. This was confirmed in the next set of experiments which were performed using the ligand to copper ratios of 2/1, 4/1 and 8/1 and showed that a higher ligand to copper ratio accelerates the polymerization rate, Table 8. The kinetic plots showed that there is no difference in the polymerization rates between the ratios 2/1 and 4/1, FIG. 10(A), but with an 8-fold excess of ligand the rate of the reaction was approximately 5 times faster. Furthermore, there was no broadening of molecular weight distributions at higher conversions and $M_w/M_n \leq 1.40$. The polymerizations results suggest that despite the relatively high stability of the TPMA copper complex, at the low catalyst concentrations used in ARGET ATRP system, L/Cu ratios of 2/1 and 4/1 provided insufficient stabilization of the copper complexes, and a larger excess of ligand is necessary to shift equilibrium towards the Cu(I)/L species. Thus, a L/Cu ratio of 8/1 was used for all subsequent experiments targeting a well controlled aqueous ARGET ATRP.

Figure 10B:
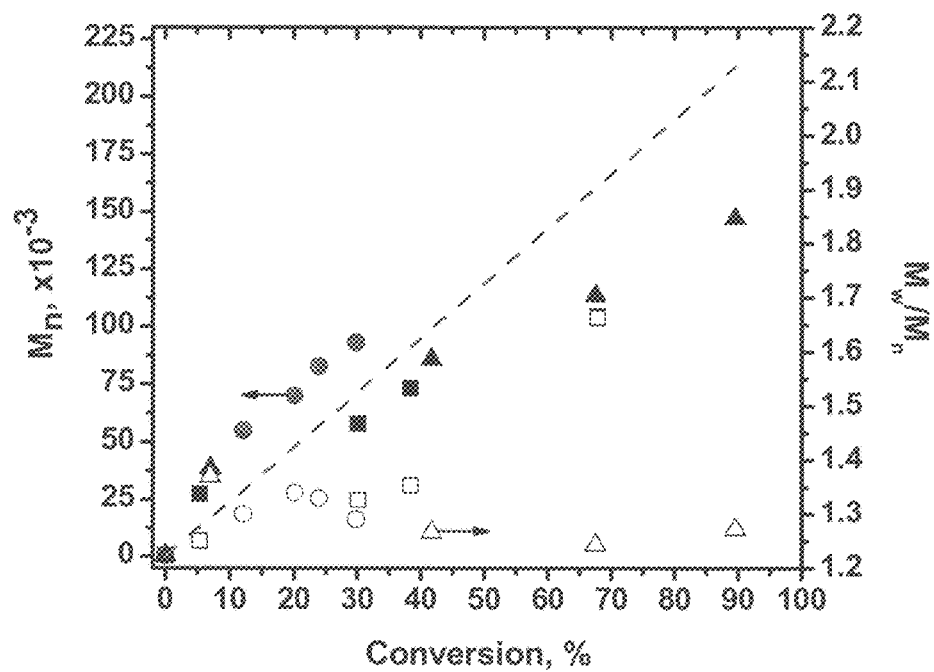
FIG. 10(B): evolution of molecular weight $M_n$ (solid shapes) and molecular weight distribution $M_w/M_n$ (open shapes) with conversion; reaction conditions [OEOMA$_{475}$]$_0$=0.5 M; [OEOMA$_{475}$]/[I]/[TPMA]/[CuBr$_2$]=500/1/0.05n/0.05 (where n is 2, 4, 8); FR$_{AA}$=16 nmol/min

Other parameters had to be examined since while the reaction was faster with more ligand, it was not as well controlled as desired for the application. This can be seen by the deviation from linear dependence in molecular weight evolution at higher conversion, FIG. 10(B).

TABLE 8

ARGET ATRP of OEOMA$_{475}$ with varied Cu/L ratio

| Run | M/I/TPMA/CuBr$_2$ | L/Cu | Cu$^a$, ppm | Time h | Conv % | M$_{n\ th}{}^b$ × 10$^{-3}$ | M$_{n\ GPC}{}^c$ × 10$^{-3}$ | M$_w$/M$_n$ |
|---|---|---|---|---|---|---|---|---|
| 1 | 500/1/0.1/0.05 | 2/1 | 100 | 23 | 68 | 161 | 104 | 1.66 |
| 2 | 500/1/0.2/0.05 | 4/1 | 100 | 6 | 30 | 71 | 93 | 1.29 |
| 3 | 500/1/0.4/0.05 | 8/1 | 100 | 5 | 78 | 186 | 106 | 1.40 |

All polymerizations were conducted with [M]$_0$ = 0.5M, [I]$_0$ = 1 mM, [TEABr]$_0$ = 100 mM; FR$_{AA}$ = 16 nmol/min;
$^a$Calculated by the initial molar ration of CuBr$_2$ to the monomer;
$^b$M$_{n\ th}$ = ([M]$_0$/[I]$_0$) × conversion × M$_{monomer}$;
$^c$universal calibration DSRC6D: Influence of Counterion and an Added Salt.

Figure 11A:
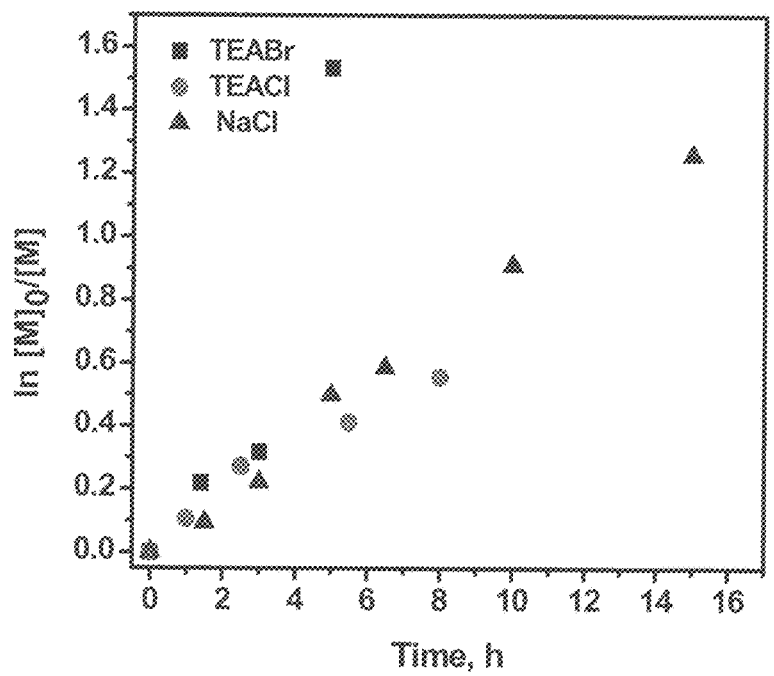
FIG. 11(A): Effect of the type of halide on the ARGET ATRP of OEOMA$_{475}$ in water at 30° C. First-order kinetic plot.
Figure 11B:
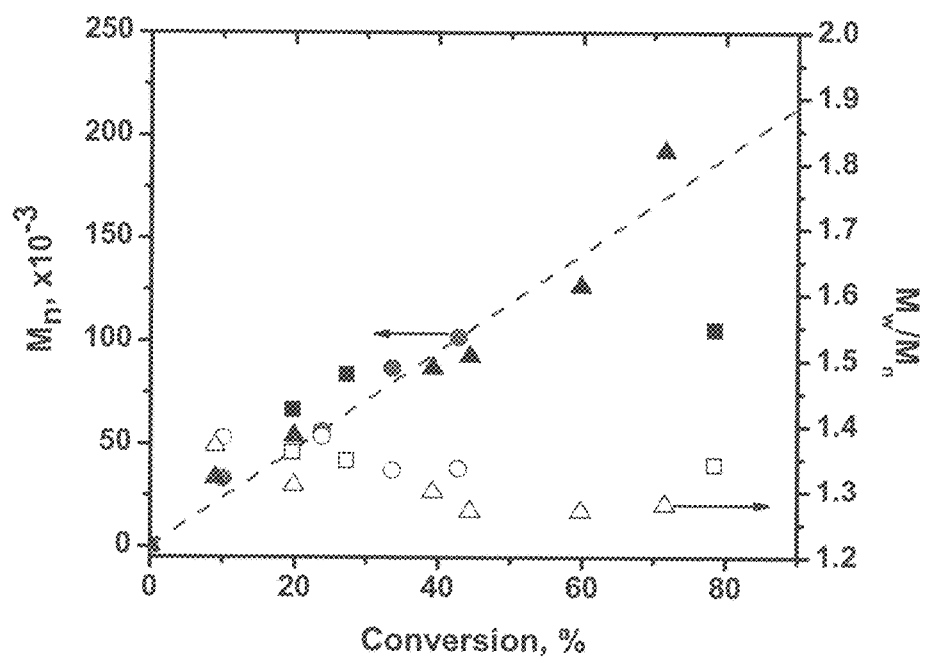
FIG. 11(B): evolution of $M_n$ (solid shapes) and molecular weight distribution $M_w/M_n$ (open shapes) with conversion. [OEOMA$_{475}$]$_0$=0.5 M; [OEOMA$_{475}$]/[I]/[TPMA]/[CuBr$_2$]=500/1/0.4/0.05, FR$_{AA}$=16 nmol/min.
Figure 12A:
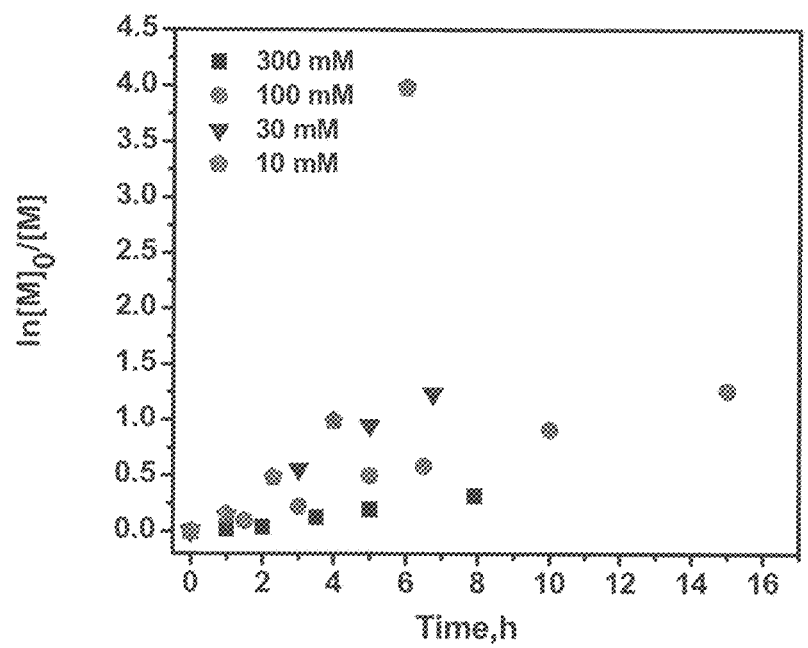
FIG. 12(A): Effect of the NaCl concentration on the ARGET ATRP of OEOMA$_{475}$ in water at 30° C. First-order kinetic plot.
Figure 12B:
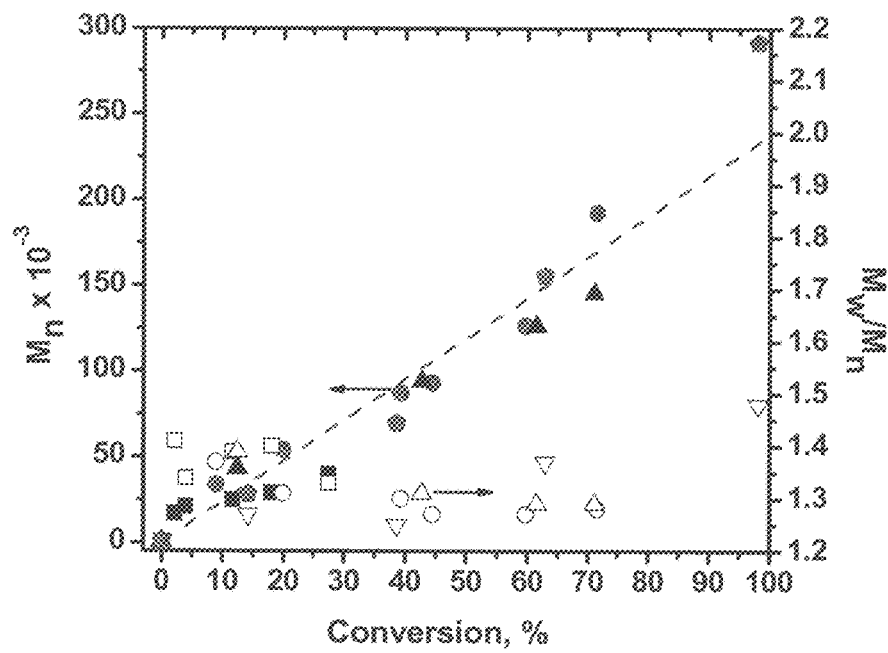
FIG. 12(B): evolution of molecular weight $M_n$ (solid shapes) and molecular weight distribution $M_w/M_n$ (open shapes) with conversion.

The next parameter examined was the nature of the halogen species which can influence the polymerization. A chlorine capped chain is typically 10-100 times less active than bromine capped chain but the carbon-chlorine bond is more hydrolytically stable. Table 9, runs 1-3 and FIG. 11(A) and FIG. 11(B) illustrate the polymerization results for polymerizations conducted in the presence of different salts: TEABr, TEACl, and NaCl. When chloride salts were added to the reaction medium the reaction proceeded in more controlled manner. Linear first-order kinetics and linear evolution of molecular weight with conversion was observed for polymerizations in the presence of TEACl and NaCl. As expected, polymerization with TEACl is similar to the polymerization with NaCl, indicating that only the anion, not the cation, affects the polymerization. Furthermore, the concentration Cu(II)X/L, or by the formation of inactive Cu(I)X/L species, or substitution of TPMA ligand by halide anions. The results suggest that a concentration of 300 mM NaCl was too high, as it significantly decreased the rate of polymerization without a significant improvement in the M$_w$/M$_n$ values. Lower salt concentrations of 30 and 100 mM provided linear evolution of the molecular weight with conversion and good correlation with the theoretical values, FIG. 12(B). Furthermore, there was a minimal change in the dispersity of polymers synthesized with 30 and 100 mM NaCl, while polymerization with 30 mM NaCl was 2 times faster. When a lower concentration of salt, 10 mM, was used, the first-order kinetic plot deviated from linearity and M$_w$/M$_n$ values increased to approximately 1.5, FIG. 12(A) and FIG. 12(B), which suggests that a NaCl concentration of 10 mM was too low to prevent deactivator dissociation.

TABLE 9

ARGET ATRP of OEOMA$_{475}$ with varied salt and salt concentration

| Run | M/I/TPMA/CuBr$_2$ | Salt, mM | Cu$^a$, ppm | Time h | Conv % | M$_{n\ th}{}^b$ × 10$^{-3}$ | M$_{n\ GPC}{}^c$ × 10$^{-3}$ | M$_w$/M$_n$ |
|---|---|---|---|---|---|---|---|---|
| 1 | 500/1/0.4/0.05 | TEABr, 100 | 100 | 5 | 78 | 186 | 106 | 1.40 |
| 2 | 500/1/0.4/0.05 | TEACl, 100 | 100 | 8 | 43 | 102 | 102 | 1.40 |
| 3 | 500/1/0.4/0.05 | NaCl, 100 | 100 | 15 | 72 | 170 | 192 | 1.28 |
| 4 | 500/1/0.4/0.05 | NaCl, 300 | 100 | 8 | 27 | 64 | 59 | 1.33 |
| 5 | 500/1/0.4/0.05 | NaCl, 30 | 100 | 6.75 | 71 | 169 | 145 | 1.29 |
| 6 | 500/1/0.4/0.05 | NaCl, 10 | 100 | 6 | 98 | 233 | 292 | 1.48 |

All polymerizations were conducted with [M]$_0$ = 0.5M, [I]$_0$ = 1 mM, [TEABr]$_0$ = 100 mM, FR$_{AA}$ = 16 nmol/min;
$^a$Calculated by the initial molar ratio of CuBr$_2$ to the monomer;
$^b$M$_{n\ th}$ = ([M]$_0$/[I]$_0$) × conversion × M$_{monomer}$;
$^c$universal calibration addition of chloride salts resulted in preparation of polymers with dispersities that remained below 1.3, even at high monomer conversions.

While addition of a halide salt shifts the equilibrium toward formation of a stable deactivator and improves control over polymerization it is also important to determine the effect of the concentration of the salt on the kinetics of the polymerization. Table 9, runs 3-6 show the influence of varying the concentration NaCl starting from 10 mM to 300 mM. The rate of polymerization decreased in the presence of higher concentrations of NaCl, FIG. 12(A). The reaction with 300 mM NaCl reached less than 30% conversion in 8 h, while with 10 mM it reached almost 100% in 6 h. The slower rate of polymerization in the presence of higher salt concentration could be caused by presence of a higher DSRC6E: Variation of Cu Concentration and Targeted DP.

In ATRP the ratio of Cu$^I$ to Cu$^{II}$ determines rate of polymerization, while absolute Cu$^{II}$ concentration influences the molecular weight dispersity. Therefore, it is desirable to determine the minimal amount of Cu providing control over the polymerization and still achieving an acceptable rate of reaction. The copper concentration was varied from 30 to 300 ppm, Table 10, runs 1-4. In general the rate of polymerization was faster and control was better with higher concentrations of copper. The reaction rate decreased approximately 10 fold, and dispersities increased from 1.2 to 1.5, as the copper concentration was progressively decreased from 300 to 30 ppm. The results suggest that both 100 and 300 ppm provided acceptable rates of reaction and control over the polymerization, whereas 30 ppm was too low to control the reaction. The dispersity in ATRP is a function of the ratio of the concentration of the ATRP initiator and the concentration of XCu(II)/L in solution. Therefore when a polymerization is poorly controlled, such as the reaction with 30 ppm catalyst, increasing the targeted degree of polymerization (DP) from 500 to 1000 could improve the level of control over the structure of the final polymer at the same DP. Although, there was some improvement in the dispersity when the targeted DP was increased from 500 to 1000, both polymers had high dispersities, nonlinear evolution of molecular weight, and poor correlation between theoretical and experimental molecular weights which could be due to transfer reactions or the presence of dimethacrylate impurities in the commercial samples of OEOMA$_{475}$.

Finally, while retaining the concentration of catalyst at 100 ppm, the targeted DP was varied. In these reactions the concentration of initiator was varied in the presence of constant concentrations of copper and monomer, see Table 10, runs 1, 5 and 6. The rate of reaction was faster at higher initiator concentrations, which was expected because of the dependency between rate of reaction and initiator concentration. In all cases the reactions showed linear first-order kinetics, linear evolution of molecular weight with conversion, good correlation between experimental and theoretical molecular weights and generated polymers with narrow dispersity <1.3.

one was conducted with 20% monomer and the other with 10% monomer, feeding speed of ascorbic acid was almost the same (1 nmol/min/mL vs. 0.8 nmol/min/mL) and a salt with a common counterion was added to the aqueous medium; either 100 mM of halide salt of the tetraethylammonium cation (TEA): either TEABr or TEACl. The reactions were slower than the reactions conducted with higher concentration of catalyst but were controlled polymerizations.

An additional series of runs are reported in Table 11. All polymerizations reached around 70% conversion in 10 h. All of them had 100 mM NaCl or TEACl, DP=100, and Cu/L=1/10, except for run 3-17 where Cu/L=1/8. The rate of addition of the reducing agent (FR$_{AA}$) was varied from 32 nmol/min to 4 nmol/min. However, all reaction reached approximately the same molecular weight in 10 h. This shows that 4 nmol/min of reducing agent is sufficient to form an appropriate ratio of activator to deactivator for a well controlled polymerization. However if the rate of addition of reducing agent is further reduced to 0.5 or 1.5 nmol/min then reactions are quite slow, runs 3-27 and 3-28.

Increasing the concentration of extra halide salt to 150 mM does not result in a significant change in the polymerization, run 3-19.

TABLE 10

ARGET ATRP of OEOMA$_{475}$ with varied copper concentration and DP

| Run | M/I/TPMA/CuBr$_2$ | DP | Cu$^a$, ppm | Time, h | Conv., % | M$_{n\ th}^{b}$ × 10$^{-3}$ | M$_{n\ GPC}^{c}$ × 10$^{-3}$ | M$_w$/M$_n$ |
|---|---|---|---|---|---|---|---|---|
| 1 | 500/1/0.4/0.05 | 500 | 100 | 15 | 72 | 170 | 192 | 1.28 |
| 2 | 500/1/1.2/0.15 | 500 | 300 | 5 | 79 | 189 | 226 | 1.23 |
| 3 | 500/1/0.12/0.015 | 500 | 30 | 15 | 69 | 164 | 113 | 1.51 |
| 4 | 500/0.5/0.24/0.03 | 1000 | 30 | 13 | 20 | 47 | 103 | 1.46 |
| 5 | 500/0.5/0.8/0.1 | 1000 | 100 | 10 | 36 | 200 | 198 | 1.33 |
| 6 | 500/2/0.2/0.025 | 250 | 100 | 10 | 62 | 74 | 91 | 1.28 |

All polymerizations were conducted with [M]$_0$ = 0.5M, [NaCl]$_0$ = 100 mM, FR$_{AA}$ = 16 nmol/min; [I]$_0$ = 1 mM, except for entry 4-5: [I]$_0$ = 0.5 mM, and for entry 6: [I]$_0$ = 2 mM;
$^a$Calculated by the initial molar ration of CuBr$_2$ to the monomer;
$^b$M$_{n\ th}$ = ([M]$_0$/[I]$_0$) × conversion × M$_{monomer}$;
$^c$universal calibration (SI)

DSRC7. Exemplary ARGET ATRP Examples

Initially two ARGET ATRP reactions were conducted with continuous feeding of ascorbic acid with 100 ppm copper, molar ratio of Cu(II) to monomer, in water with OEOMA$_{475}$ as exemplary water soluble biocompatible monomer The reactions differed in monomer concentration,

TABLE 11

ARGET ATRP of OEOMA$_{454}$

| Run | M/I/TPMA*/CuII/AA | FA$_{AAa}$, nmol/min | Salt, mM | Time, h | M$_n$ × 10$^{-3}$ | Mw/Mn |
|---|---|---|---|---|---|---|
| 3-17 | 500/1/0.4/0.05/1 | 16 | NaCl, 100 | 10 | 98 | 1.30 |
| 3-19 | 500/1/0.5/0.05/0.7 | 16 | NaCl, 150 | 7 | 89 | 1.26 |
| 3-22 | 500/1/0.5/0.05/1 | 16 | TEACl, 100 | 10 | 102 | 1.25 |
| 3-24 | 500/1/0.5/0.05/1 | 10 | NaCl, 100 | 10 | 103 | 1.33 |
| 3-26 | 500/1/0.5/0.05/0.2 | 4 | NaCl, 100 | 10 | 95 | 1.29 |
| 3-27 | 500/1/0.5/0.05/0.03 | 0.5 | NaCl, 100 | 10 | 30 | 1.41 |
| 3-28 | 500/1/0.4/0.05/0.09 | 1.5 | NaCl, 100 | 10 | 44 | 1.29 |

[I] = 1 mM; 30° C.; 20% [M] (v/v), 10% [M] (v/v); water,
aRate of addition of ascorbic acid A more extensive series of ARGET ATRP reactions of OEOMA$_{475}$ were conducted and are reported in Table 12. Different concentrations of catalysts, different salts and different rates of AA addition were examined. One can conclude that an increase of ratio of ligand to copper significantly improves polymerization rate. Second, after 50% conversion MWD of polymers increases either due to increased termination or loss of deactivator. Therefore a different halide salt: TEACl instead of TEABr (#16-17) was examined. Reaction with chloride ions was slower although the MWD of polymers formed in both reactions were close and the reaction with additional chloride showed more linear increase in MW with conversion. If you add a comparison with reaction #18, then you can notice that doubling the rate of addition of the ascorbic acid gives you faster polymerization. However, at 70% conversion the product formed showed broadening of molecular weight distribution.

In summary, this series of experiments was designed to determine suitable reaction conditions for a biologically compatible polymerization of OEOMA$_{475}$ is: NaCl (19 mg, 0.33 mmol), OEOMA$_{475}$ (2.375 g, 5 mmol), 100 mM stock solution HEBriB (0.1 mL, 0.01 mmol), 25 mM stock solution CuBr$_2$ and 200 mM stock solution TPMA (20 µL, 0.5 µmol CuBr$_2$ and 4 µmol TPMA) were dissolved in H$_2$O (7.6 mL). DMF (0.1 mL) was added as internal standard for $^1$H NMR analysis. The mixture was charged into a 10 mL Schlenk flask and purged with nitrogen for 30 min, and placed in an oil bath at 30° C. An ascorbic acid solution (16 mM) was purged with nitrogen, and then fed into the reaction using a syringe pump at the rate 1 µL/min. Samples were taken throughout the reaction for GPC and NMR analysis. Well controlled polymerizations were observed.

TABLE 12

Aqueous ARGET ATRP of OEOMA$_{475}$

| # | M/I/TPMA/Cu$^{II}$/AA | $C_M$, mol/L | Cu, ppm | Salt, mM | RA$_{AA}$[a], nmol/min | Time, h | Conversion, % | Theoretical | GPC (PMMA st) | Calculated w/ Mark-Houwink parameters | $M_w/M_n$ |
|---|---|---|---|---|---|---|---|---|---|---|---|
| 1 | 455:1:0.045:0.091:5 | 0.5 | 100 | — | 2 | 6 | — | | 132 | | 3.4 |
| 2 | 455:1:0.045:0.091:5 | 0.5 | 100 | TEABr, 2 | 6/20 | 11/40 | | 24/42 | | 1.38/1.64 |
| 3 | 500/1/0.05/0.1/0.336 | 0.5 | 100 | TEABr, 8 | 7 | 18 | 43.7 | 28.9 | | 1.30 |
| 4 | 500/1/0.05/0.1/1.344 | 0.5 | 100 | TEABr, 32 | 7 | 29 | 68.6 | 35.6 | | 1.42 |
| 5 | 500/1/0.1/0.05/4.4 | 0.5 | 100 | TEABr, 32 | 10/23 | 52/67 | 124/159 | 55/79 | 100/157 | 1.39/1.85 |
| 6 | 500/1/0.1/0.05/2.2 | 0.5 | 100 | TEABr, 16 | 10/23 | 38/68 | 91/161 | 49/68 | 87/131 | 1.35/1.66 |
| 7 | 500/1/0.1/0.05/1.1 | 0.5 | 100 | TEABr, 8 | 9.5/23 | 31/41 | 74/98 | 42/48 | 72/85 | 1.32/1.35 |
| 8 | 500/1/0.5/0.25/0.5 | 0.5 | 500 | TEABr, 16 | 5 | 50 | 120 | 65 | 121 | 1.31 |
| 9 | 500/1/0.5/0.25/0.3 | 0.5 | 500 | TEABr, 16/4 | 4.5 | 69 | 164 | 73 | 137 | 1.29 |
| 10 | 500/1/0.1/0.05/1.6 | 0.5 | 100 | TEABr, 16/8 | 10/23.5 | — | — | 36/37 | — | 1.39/1.32 |
| 11 | 500/1/0.1/0.05/1.7 | 0.5 | 100 | TEABr, 16/6 | 8.8/22.5 | — | — | 34/29 | — | 1.32/1.52 |
| 12 | 1000/1/0.1/0.05/2 | 1 | 50 | TEABr, 16 | 9/21 | 45/65 | 214/310 | 105/178 | 206/— | 1.21/2.38 |
| 13 | 1000/1/0.8/0.1/0.1 | 1 | 100 | TEABr, 16 | 1 | — | — | 98 | 191 | 1.26 |
| 14 | 1000/1/0.8/0.1/0.1 | 1 | 100 | TEABr, 16/4 | 1/2 | 32/48 | 151/228 | 46/55 | 80/99 | 1.22/1.32 |
| 15 | 500/1/0.4/0.05/0.5 | 0.5 | 100 | TEABr, 16 | 5 | 78 | 186 | 69 | | 1.34 |
| 16 | 500/1/0.4/0.05/0.8 | 0.5 | 100 | TEACl, 16 | 8 | 43 | 102 | 67 | | 1.34 |
| 17 | 500/1/2/0.25/0.3 | 0.5 | 500 | TEACl, 16 | 3 | 70 | 165 | 120 | | 1.26 |
| 18 | 500/1/0.4/0.05/1.9 | 0.5 | 100 | TEACl, 32 | 7.3/10 | 46/68 | 110/163 | 81/64 | | 1.34/1.55 |
| 19 | 500/1/0.4/0.05/1.3 | 0.5 | 100 | NaCl, 32 | 7 | 52 | 124 | 81 | | 1.28 |
| 20 | 500/1/0.2/0.025/3 | 0.5 | 50 | NaCl, 32 | 6.75/16 | 34 | 80 | 40/45 | | 1.46/2.43$^{bm}$ |
| 21 | 250/1/0.2/0.025/3 | 0.5 | 100 | NaCl, 32 | 6.25 | 54 | 64 | 36 | | 1.36 |

[a]Rate of addition of ascorbic acid; all polymerizations were conducted at 30° C.; THF GPC was used to measure molecular weight (instrument 2); GPC/MALLS were used to measure weight-average molecular weight of some samples, dn/dc values and Mark-Houwink parameters.

TABLE 13

ARGET ATRP of OEOA$_{480}$ with ascorbic acid feeding.

| Run # | M/I/TPMA/CuBr2 | FR$_{AA}$, nmol/min | Salt, mM | Cu, ppm | Time, h | Conv., % | $M_{nth} \times 10^{-3}$ | $M_n \times 10^{-3}$ | $M_w/M_n$ |
|---|---|---|---|---|---|---|---|---|---|
| 3-72 | 500/1/1.2/0.15 | 50 | TEABr, 30 | 300 | 15 | 71 | 170 | 53 | 1.25 |
| 3-73 | 500/1/0.2/0.05 | 50 | NaCl, 30 | 100 | 15 | 19 | 45 | 28 | 1.13 |
| 3-74 | 500/1/1.2/0.15 | 50 | NaCl, 30 | 300 | 15 | 33 | 80 | 39 | 1.11 |

DSRC7A: Acrylate Monomer

An acrylate monomer, OEOA$_{454}$, was also polymerized under ARGET conditions and the results are shown in Table 13.

DSRC7B: ARGET ATRP Synthesis of POEOMA-b-POEOA Block Copolymer.

Figure 13:
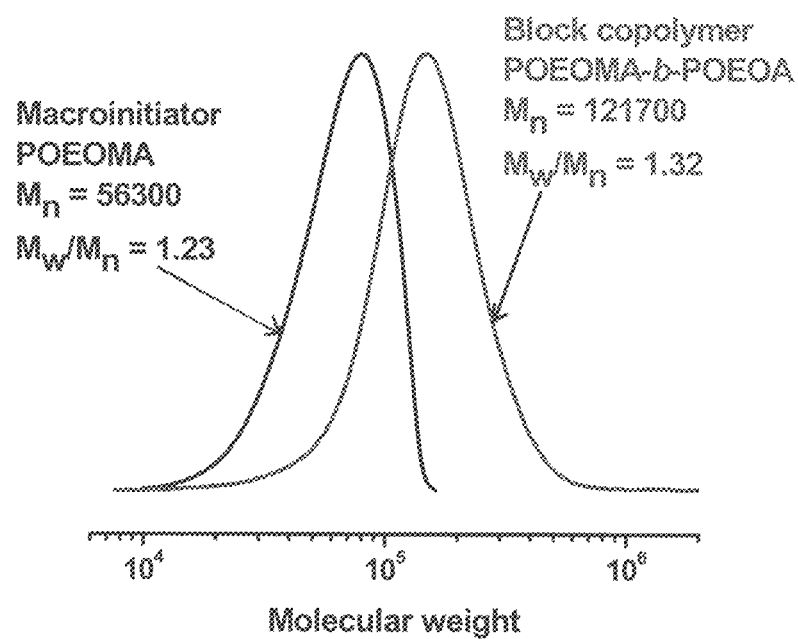
FIG. 13: GPC chromatographs of the poly(OEOMA$_{475}$)-Cl macroinitiator and poly(OEOMA$_{475}$)-b-poly(OEOA$_{480}$) block copolymer. Polymerization of OEOMA$_{475}$ conducted in water (~80%) at 30° C. with [M]$_0$=0.5 M, [I]$_0$=2 mM, 100 mM NaCl, FR$_{AA}$=16 nmol/min; polymerization of OEOA$_{480}$ conducted in water (~80%) at 30° C. with [M]$_0$=0.5 M, [I]$_0$=1 mM, 30 mM NaCl, FR$_{AA}$=50 nmol/min

Living chain-end functionality was confirmed by chain extension of a poly(OEOMA$_{475}$) macroinitiator with OEOA$_{480}$. The macroinitiator was synthesized using aqueous ARGET ATRP with 100 ppm of copper, Cu/L=1/8, 100 mM NaCl and FR$_{AA}$=16 nmol/min. The poly(OEOMA$_{480}$) block was prepared using similar conditions, except that the ascorbic acid was fed at a higher rate; FR$_{AA}$=50 nmol/min. The higher feeding rate was chosen since acrylates have a lower ATRP equilibrium constant than methacrylates, implying that a larger fraction of the copper should be reduced for the reaction to commence. The formation of the block copolymer was confirmed by a clear shift in the molecular weight distribution after chain extension, FIG. 13. The resulting block copolymer had a low dispersity of 1.32, and its molecular weight was close the theoretically expected value.

DSRC7C: NaCl (58 mg, 1 mmol), OEOMA$_{475}$ (2.375 g, 5 mmol), 100 mM stock solution HEBriB (0.2 μL, 0.02 mmol), 25 mM stock solution CuBr$_2$ and 200 mM stock solution TPMA (20 μL, 0.5 μmol CuBr$_2$ and 4 μmol TPMA), DMF (0.1 mL) were dissolved in H$_2$O (7.5 mL). The mixture was charged into a 10 mL Schlenk flask and purged with nitrogen for 30 min, and then placed in an oil bath at 30° C. An ascorbic acid solution (16 mM) was purged with nitrogen, and then fed in via syringe pump at the rate 1 μL/min. After 10 h reaction was stopped by exposure to the air and diluted with water. The polymer was extracted from the reaction mixture with 4×50 mL DCM. The organic phases were collected, and the solvent removed under reduced pressure. The residue was dissolved in THF and passed over neutral alumina to remove the copper catalyst. The polymer was precipitated into diethyl ether, the mixture was centrifuged at 4000 rpm for 5 min. The supernatant was disposed and procedure repeated 2 more times. The poly(OEOMA) was dried under vacuum overnight, and characterized by GPC. The polymer with M$_n$=56,000, and M$_w$/M$_n$=1.23 was obtained.

The procedure for the chain extension with POEOA follows: POEOMA (0.3 g, 0.005 mmol), OEOA$_{480}$ (1.2 g, 2.5 mmol), NaCl (19 mg, 0.33 mmol), 25 mM stock solution CuBr$_2$ and 200 mM stock solution TPMA (20 μL, 0.25 μmol CuBr$_2$ and 2 μmol TPMA), DMF (0.1 mL) were dissolved in H$_2$O (3 mL). The mixture was charged in the 10 mL Schlenk flask and purged with nitrogen for 30 min, and then placed in an oil bath at 30° C. An ascorbic acid solution (50 mM) was purged with nitrogen, and then fed into the reaction mixture using a syringe pump at the rate 1 μL/min. After 15 h reaction was stopped and analyzed by GPC: M$_n$=121,700, M$_w$/M$_n$=1.32.

DSRC7D: ARGET ATRP with DMAEMA

In order to extend and exemplify the developed aqueous A(R)GET ATRP to other monomers, in addition to biocompatible OEOMA$_{475}$ a series of reactions with dimethylaminoethyl methacrylate (DMAEMA, Scheme 8) were conducted.

Scheme 8. ARGET ATRP of DMAEMA in aqueous media with feeding ascorbic acid (AA)

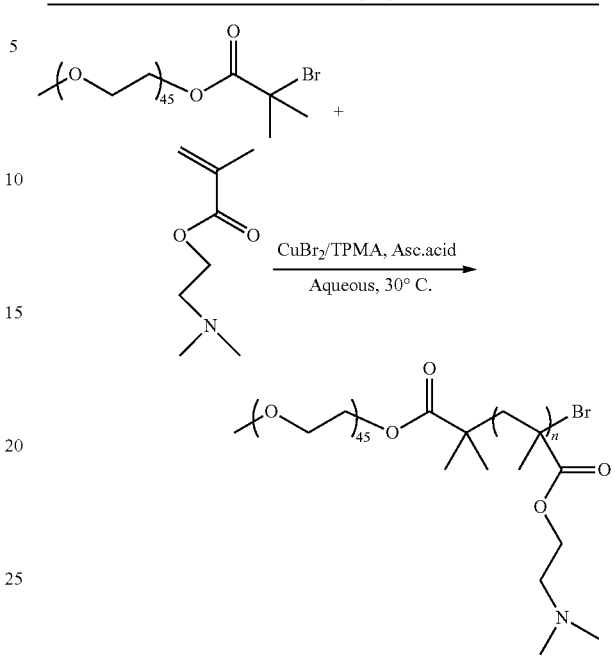

The ratio of reagents used in the reaction was M/I/TPMA/CuBr$_2$=594/1/2.4/0.3 with a total volume of the reaction medium of 5 mL and the initial concentration of monomer and initiator, [M]$_0$=3 M, [I]$_0$=5 mM respectively, with the copper concentration=500 ppm. Ascorbic acid added at a rate of 2 nmol/min. The polymerization displayed nearly linear first order kinetics and M$_w$/M$_n$ was close to 1.35 at 45% conversion DSRC7D2: ARGET ATRP with Quaternized DMAEMA Reaction conditions similar to developed for OEOMA$_{475}$. were used; 20 vol. % monomer, 1 mM of the initiator, 300 ppm copper; ratio of reagents M/I/TPMA/CuBr$_2$ =1187/1/3.2/0.4. After all reagents were mixed in the reaction flask hydrogen chloride was slowly added until the pH=~6. The polymerization was very slow and after 4 h the MW was only 4200 but M$_w$/M$_n$ was 1.06. In order to reduce the probability that the acid could influence the stability of the catalyst complex the sequence of adding the reagents to the reaction flask were changed. Before adding the initiator and catalyst complex to the flask the monomer and solvent were mixed and then hydrogen chloride added till pH ~6. The rate of addition of the ascorbic acid was increased to 8 nmol/min which resulted in the polymerization reaching 48% conversion in 4 hours. It would be expected that other halogens and the presence of an additional buffer would provide more control.

DSRC8: Start/Stop Polymerization.

In the new disclosed aqueous ARGET ATRP method, ascorbic acid is fed in to continuously regenerate a low fraction of the Cu$^I$ species in solution and promote polymerization. Therefore, if the reducing agent is not added, a small amount of termination will lead to a significant build up the deactivator, and shift the ATRP equilibrium toward the dormant species. The following experiment demonstrated that the reaction can be started or slowed down and stopped on demand by turning on or off the feeding of ascorbic acid, as demonstrated in electrochemically mediated ATRP or photoinduced ATRP. The start/stop reaction was performed using a catalyst loading of 300 ppm with $FR_{AA}$=16 nmol/min, FIG. 7(A) and FIG. 7(B). The ascorbic acid was fed for 1 h, during which time the polymerization proceeded at a relatively fast rate. After 1 h the feeding was turned off, and polymerization rate decreased significantly. This cycle was repeated two more times, resulting in stepwise conversion up to 60%. Throughout the whole experiment the dispersities were low and the molecular weights agreed well with the theoretical values. The clustering of the points during non-feeding regimes shows that slow feeding is required to trigger and maintain polymerization. Furthermore, the efficient re-initiation of the dormant polymers in solution confirms the high ω-chain end group functionality throughout the polymerization.

In conclusion, ARGET ATRP with continuous feeding of ascorbic acid is very promising approach for synthesis of water soluble polymers in aqueous media, particularly under biologically compatible conditions. ARGET ATRP was used to create well defined polymers of OEOMA$_{475}$ in aqueous media at ambient temperature (30° C.) using catalyst concentrations between 100-300 ppm. In order to obtain well-controlled polymers, the ascorbic acid reducing agent should be slowly fed into the reaction medium and a large excess of halide salt should be added to ensure a sufficiently high concentration of the deactivator complex in the reaction medium. Polymerizations with chloride ions showed a slower reaction but improved control compared to bromide ions, with the optimal concentration of the halide salt being between 30 and 100 mM. For improved control and faster kinetics, an excess of the ligand over copper is desired, whereas a faster feeding rate of the reducing agent only gives a minimal improvement in the kinetics and leads to a decrease in the control over the final polymer. In the aqueous ARGET ATRP system, the ascorbic acid reducing agent should be slowly fed into the system, allowing the reaction to be commenced or ceased at any point simply by starting or stopping the feeding of the reducing agent. The low catalyst concentrations and aqueous media are biologically friendly, making the aqueous ARGET ATRP method an excellent technique for creating bioconjugates, as demonstrated below by the synthesis of a BSA based protein-polymer hybrid.

DSRC9. ICAR with Low [Cu]

Scoping experiments were performed in water with 100 ppm Cu/TPMA catalyst under ICAR conditions. The key premise in this example is that control can be obtained under low catalyst concentrations in water by using 100 mM TEABr to promote the formation of the deactivator. OEOA$_{475}$ was selected as monomer for the preliminary ICAR ATRP with, 2-hydroxyethyl 2-bromo-2-methylpropanoate (HEBrMeP) as the ATRP initiator and the water soluble azo initiator VA-044 was selected to form radicals. This azo initiator has a 10 h half life temperature of 44° C., therefore all reactions were performed at this temperature, at least in the initial phase. This temperature is still low enough not to denature many proteins, and in principle a higher azo initiator loading could be used in protein systems if lower temperatures are considered necessary.

The initial reaction was conducted with [OEOA]:[HEBrMeP]:[VA-044]:[CuBr$_2$]:[TPMA]=400:1:0.1:0.04:0.08 was performed under the conditions of 10% monomer in water with [TEABr]=100 mM and essentially showed no conversion. This suggested that the reaction was too slow under these conditions. In order to accelerate the reaction the system was modified to the following conditions: [OEOA]:[HEBrMeP]:[VA-044]:[CuBr$_2$]:[TPMA]=400:1:0.3:0.04:0.08 under 20% monomer in water with 100 mM TEABr.

These polymerizations displayed linear first order kinetics, and linear evolution of molecular weight with conversion. MW reached 50,000 after 20 h and the PDIs are very low, considering the very low Cu concentration (100 ppm) with many samples having PDI≈1.15.

Additional runs were conducted with 50 ppm, 20 ppm and 5 ppm catalyst complex and the results show that the molecular weight can accurately be targeted, as seen by an increase in the slope of the $M_n$ vs. conversion plots for the DP 800, DP 400 and DP 200 series. In all cases the semi-logarithmic plots were linear, and the molecular weight vs. conversion was also linear, except for the 5 PPM sample, which can be explained by the poor control. Similarly the PDI's were all in the order of 1.1-1.25, except at short chain lengths, or in the 5 PPM system. The later is again due to the poor control. Overall it appears that the OEOA bromide ICAR system is very well controlled with catalyst concentrations above 5 ppm.

OEOMA ($M_n$=475) was also investigated, and the preliminary study of [OEOMA]:[HEBrMeP]:[VA-044]:[CuBr$_2$]:[TPMA]=400:1:0.1:0.04:0.08 with 20% monomer in water suggested that it is possible to perform ICAR of OEOMA with molecular weight increasing with time, although the PDIs were higher than for OEOA, typically 1.3-1.35.

DSRC10: Electrochemically Controlled Aqueous ATRP of OEOMA (eATRP)

DSRC10A. eATRP of oligo(ethylene glycol) methyl ether methacrylate (OEOMA$_{475}$) in Water.

Figure 9B:
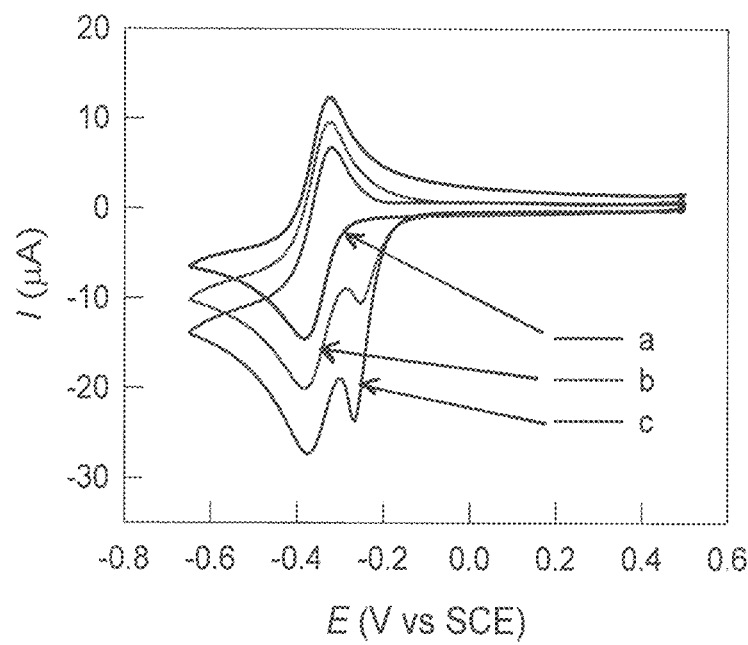
FIG. 9(B): Cyclic voltammetry of 1 mM Cu$^{II}$L$^{2+}$ in the absence (a) and presence of 1 mM HEBriB (b) or 2 mM HEBriB (c), recorded at 0.1 V/s in H$_2$O+0.1 M Et$_4$NBF$_4$.

The Cu/TPMA complex, which is one of the most active complexes used in ATRP, was chosen as the catalyst system for evaluation of an eATRP under biologically compatible conditions. In cyclic voltammetry screening the $Cu^{II}L^{2+}$ exhibits a reversible peak couple with $E^{\theta'}$=−0.245 V vs SCE, FIG. 9(A). Addition of a large excess of Br$^-$ to the solution does not significantly affect this CV response, indicating that the $K_X$ of $Cu^{II}L^{2+}$ is very small, FIG. 9(B). The full reversibility of the response at very low scan rates confirms that $Cu^{I}L^{+}$ is quite stable in H$_2$O with a lifetime of at least few seconds, the time scale of CV. Using the above reported $E^{\theta'}$ value together with other available thermodynamic data, the value of $K_D$ was estimated to be 6.8×10$^{-3}$ for the disproportionation of $Cu^{I}L^{+}$. The CV response of $Cu^{II}L^{2+}$ drastically changes when an equimolar amount of the initiator, 2-hydroxyethyl 2-bromoisobutyrate (HEBriB) is added. The cathodic peak approximately doubles in height while the anodic peak decreases indicating that the formed $Cu^{I}L^{+}$ rapidly reacts with HEBriB. On the basis of thermodynamic data available in the literature, we estimated a value for $K_{ATRP}$ of 1.5×10$^{-1}$ for this system, which is 4 orders of magnitude higher than that measured for an analogous system in CH$_3$CN. An estimate of the activation rate constant based on voltammetric analysis of the system $Cu^{II}L^{2+}$+HEBriB at different concentration ratios are shown in FIG. 9(B), and different scan rates provide a very large value for $k_{act}$≥2.5×10$^6$ M$^{-1}$s$^{-1}$.

The above described voltammetric analyses have shown that the system under investigation has all the characteristics that make aqueous ATRP reactions very difficult to control; low $K_X$, high $K_{ATRP}$, and extremely rapid activation. Therefore, it represents an excellent test of the potential of the proposed electrochemical method to resolve problems still facing application of ATRP to certain systems, herein exemplified by aqueous ATRP with greater than 75% water in the reaction medium. The electrogeneration of the active catalyst was carried out under potentiostatic conditions starting from the catalytic system $Cu^{II}L^{2+}$/HEBriB 1:1 in H$_2$O+10%

OEOMA475 (MW=475 gmol$^{-1}$). The effect of $E_{app}$ on the degree of control over polymerization was first investigated. Three $E_{app}$ values around $E^{\Theta\prime}$ were applied and the results are summarized in Table 5, runs 1-3. The driving force of the electrochemical process is given by $\Delta G^{\Theta}=F(E_{app}-E^{\Theta\prime})$ and the $[Cu^{II}L^{2+}]/[Cu^{I}L^{+}]$ ratio at the electrode surface is closely related to that dictated by the Nernst equation. At the beginning of the electrolysis there is only $Cu^{II}L^{2+}$ in solution, so the current has to decay as $Cu^{II}$ is converted to $Cu^{I}$, approaching a constant value corresponding to the $[Cu^{II}L^{2+}]/[Cu^{I}L^{+}]$ ratio generated by $E_{app}$. However, $Cu^{I}L^{+}$ is engaged in a reversible reaction with the initiator and the formed dormant species, which represents a continuous perturbation to the equilibrium concentrations imposed by $E_{app}$. Therefore, whether a constant $[Cu^{II}L^{2+}]/[Cu^{I}L^{+}]$ ratio can be imposed in the bulk solution depends on the mutual rates of electrogeneration and disappearance of $Cu^{I}L^{+}$ and therefore will depend on $E_{app}$.

At $E_{app}=-0.55$ V, which is $<<E^{\Theta\prime}$, the electrode process is under diffusion control and $Cu^{II}L^{2+}$ is almost quantitatively converted to $Cu^{I}L^{+}$ in a relatively short time; the current rapidly decreases to very small values. The overall rate of the process was rather high, with 79% of monomer conversion in less than 30 min, but control over polymerization was poor. The $\ln([M]/[M]_0)$ vs. time plot deviated significantly from linearity, while the molecular weight distribution of the formed polymer was very broad and the final experimental $M_n$ was 3 times larger than the theoretical one, Table 5, Run 1. These features are typical of an uncontrolled polymerization dominated by termination reactions, such as bimolecular radical-radical coupling reactions.

With $E_{app}=-0.31$ V, the current decays much less rapidly than in the case of the electrolysis at $-0.55$ V, but tends to a constant value after a long period. Under these conditions, the rate of polymerization decreased without significant improvement in the control, Table 5, Run 2.

With $E_{app}=-0.21$ V, the current decays very slowly, approaching a constant value ($\sim-250$ μA) within a short period. Under these conditions $E_{app}>E^{\Theta}$, which implies an equilibrium $[Cu^{II}L^{2+}]/[Cu^{I}L^{+}]$ ratio>>1. In this case, the process is under a good control as can be judged by the linearity of the first-order kinetic plot. Besides a nearly quantitative monomer conversion, $M_n$ increases linearly as a function of monomer conversion and polymers with $M_w/M_n \sim 1.2$ are obtained. This striking improvement of control is achieved with low charge consumption. This is a clear evidence of a drastic decrease of the termination events due to creation of a good balance between $[Cu^{I}L^{+}]$ and $[Cu^{II}L^{2+}]$.

Some experiments were run in the presence of a large excess of $X^-$ to promote formation of $\tilde{X}Cu^{II}L^+$, Table 5, Runs 4-5. The presence of additional $X^-$ in the reaction medium produces a noticeable improvement of MW distribution without any loss in the rate of monomer conversion. On the other hand, the overall rate of the process does not decrease due to the formation of inactive $Cu^{I}X_n$ species as was found in organic solvents. [Macromolecules, 2010, 42, 9257-9267; Chem. Commun. 2011, 47, 3580-3582.] Linear first-order kinetic plots were observed for all the polymerizations carried out with $[Cu^{II}L^{2+}]=0.1$ mM. In particular, experiments with different degrees of polymerization gave a fairly constant slope, $d(\ln[M]_0/[M])/dt$, suggesting that the radical concentration is unaltered. For DP=200 (1% v/v OEOMA$_{475}$), a small induction period was observed; this effect, together with the reduced rate of activation arising from the 10-fold decrease of the concentrations of $Cu^{II}L^{2+}$ and HEBriB, is a possible explanation for the mismatching between the experimental and theoretical molecular weights observed in GPC MALLS.

DSRC10B. eATRP of OEOMA$_{475}$ in Water and in the Presence of Added Salts

PBS buffer was selected as an exemplary salt since it is employed in reactions seeking bio-conjugation of a protein with a water soluble polymer. Since in this medium $E^{\Theta\prime}$ shifts to $-0.326$, $E_{app}$ was adjusted to $-0.275$ V. Although several potential side reactions perturbing the ATRP equilibrium are possible with PBS, e.g., formation of highly insoluble $Cu^{II}_3(PO_4)_2$ and/or formation of stable $Cu^{I}(H_2PO_4)_2^-$ and $Cu^{I}Cl_2^-$ salts, [Chem. Commun. 2011, 47, 3580-3582] excellent results were observed both in terms of conversion and $M_w/M_n$, see Table 5, run 5. Indeed, neither displacement of the ligand nor loss of catalysis was observed by CV analysis of the system.

The effect of targeting different DPs was also explored, Table 4, runs 6-8, using 0.1 mM $Cu^{II}L^{2+}$, 6.4 mol ppm with respect to solvent, and different concentrations of monomer. All polymerizations displayed linear $\ln([M]/[M]_0)$ vs. time plots which, together with low $M_w/M_n$ values of the final polymer, is indicative of an ATRP under good control. However, the experimental $M_n$ was significantly higher than the theoretically predicted one. This is due to low initiation efficiency at the beginning of the polymerization. Improvement was obtained with addition of PBS buffer, Table 5, run 9.

DSRC10C. eATRP of OEO$_{475}$MA Under Galvanostatic Conditions

The applied current was chose on the basis of the previous potentiostatic experiments. The magnitude of the applied current under galvinostatic conditions is of particular significance for several reasons: i) the electrogeneration rate of $Cu^I$ should be selected to maintain a low steady state concentration of $Cu^I$; ii) an high value of current could be detrimental for the process. This is important since the resistivity of the medium is increased at high monomer conversion and the potential difference necessary to maintain the set current could be larger, causing undesired redox processes such as the further reduction of $Cu^I$ to $Cu^0$ electrodeposited on the surface. Therefore, the current was set at a medium value of the previous potentiostatic experiments, equal to $I=-250$ μA.

After the first 30 minutes, the potential remained constant during the course of the polymerization. The first step is actually difficult to interpret: the current reached a minimum and then approached to a stationary value; a possible explanation is the stabilization of the electrodic activity. The first order linear plot shows an induction period of ca. 40 min, although the final conversion was 94%. The growth of the molecular weights was fairly constant resulting in a final PDI of 1.37.

In conclusion, the conditions selected for aqueous eATRP can overcome the most serious drawbacks associated with conventional aqueous ATRP. The balance between $Cu^{II}L^{2+}$ and $Cu^{I}L^+$, which is central to the successful control over the polymerization, can be regulated by appropriate selection of $E_{app}$. The best results were achieved at $E_{app}>E^0_{Cu(II)L/Cu(I)L}$, providing excellent control over MW and MW distribution, accompanied by a fast reaction and a low charge consumption. Remarkably, phosphates and halide ions can not only be tolerated but can have a beneficial effect on the level of control over the polymerization. This last observation could be attractive for biological systems.

DSRC11. Stability of GFP in Presence of ATRP Catalysts.

Figure 1:
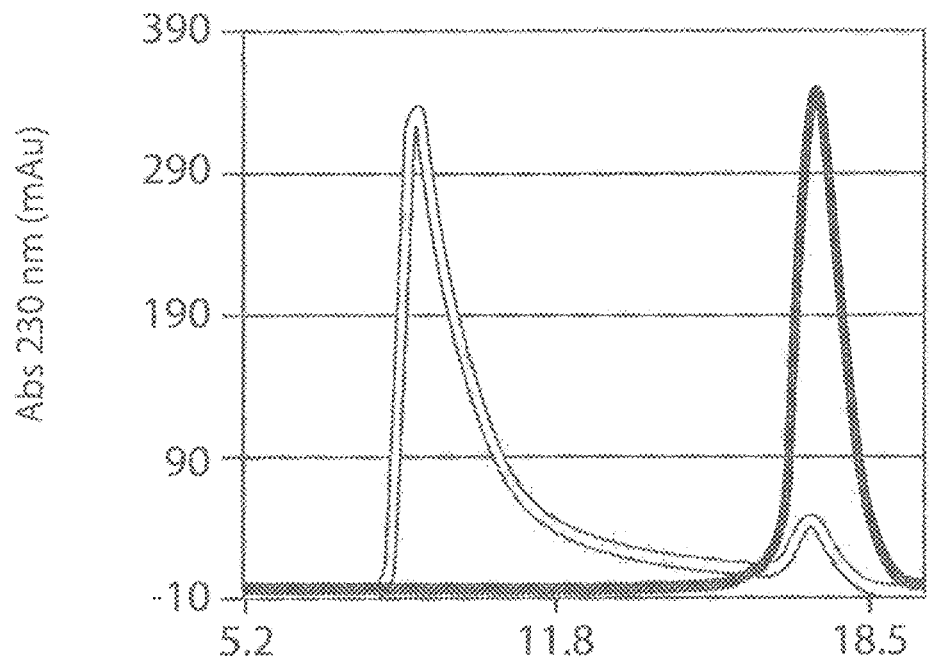
FIG. 1: Reproduced from provisional application 61/381,757. FPLC of GFP-1 reaction, GFP-1 (0 min) dark line, GFP-1-p(OEO300MA) (180 min) grey line.
Figure 2:
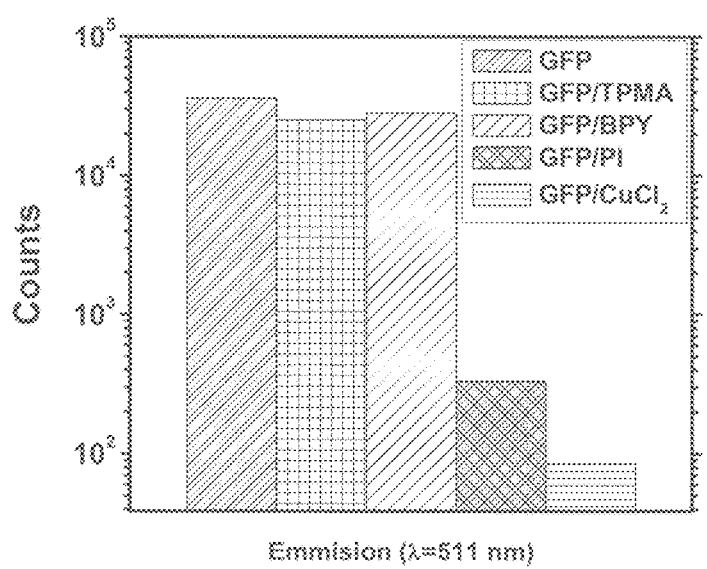
FIG. 2: Effect of components of an ATRP catalyst (Cu(II)Cl$_2$:L) on GFP (1 mg/mL) stability. [Cu(II)Cl$_2$]/[L]=1 when L=[bpy] and [PI] and =2.2 for [TPMA], and 1.1 [Cu(II)Cl$_2$]=19 mM, [OEOMA$_{475}$]=0.23 M.

The following amounts of ligand were complexed with 5 mg $CuCl_2$, 0.037 mmol, y: PI (12.2 mg, 0.082 mmol), Bpy (12.8 mg, 0.082 mmol) and TPMA (11.9 mg, 0.041 mmol) respectively. The $CuCl_2$:L were precomplexed in 200 μL of water and an additional solution of $CuCl_2$ was prepared in 200 μL of water. Once clear solutions of $CuCl_2$:L and $CuCl_2$ were obtained they were added to 2 mL of GFP solution (1 mg/mL) in PBS with 10% $OEOMA_{475}$. The solutions were centrifuged at 4000 rpm. to remove any particulates formed. Particulates were only observed for free $CuCl_2$ and $CuCl_2$: PI. 100 μL of each solution was removed for analysis using a Tecan Safire2 plate reader with a 384 well plate. Results are shown in FIG. 2, which clearly shows that when N-(n-propyl)pyridylmethanimine (PI) was used as the ligand in the presence of GFP the ligand destabilized the proteins tertiary structure as demonstrated by a loss of GFP's fluorescent properties.

Indeed in one embodiment of the invention the catalyst complex employed in the controlled grafting from biocompatible ATRP reaction is selected so that it does not influence the tertiary structure of GFP and reduce the fluorescent properties.

Example 2.

Growth of a Polymer from a Protein

Grafting from Bovine Serum Albumin (BSA). BSA was reacted with bromoisobutyryl bromide to attach ATRP initiating functionality to the BSA through the accessible lysine residues, BSA-N-iBBr. To test the efficacy of this system $OEO_{475}MA$ was polymerized using the formed BSA-N-iBBr as a protein based multifunctional initiator with a CuCl:Cu(II)$Cl_2$:Bpy catalyst system. This system was tested at 10% monomer and 10% monomer plus 10% DMSO to examine the effect of an organic co-solvent on polymerization control. The resulting semi-log plot of conversion vs. time shows linear monomer conversion for the 10% DMSO system and a curved monomer conversion for the 10% monomer only system. This can be attributed to the fact that as monomer is converted the nature of the media changes to a higher percent water and therefore the catalyst species behaves differently throughout the course of the reaction in the pure monomer system. Whereas in the 10% DMSO case where there is a constant "inert" organic component that can stabilize the catalyst species and provided a more linear polymer growth, FIG. 8(A) and FIG. 8(B).

An issue that arose in the analysis of the samples formed in this grafting from ATRP is that there was no efficient manner to analyze the molecular weight of the formed protein-polymer hybrid species due to the lack of an aqueous GPC in the laboratories. In order to overcome this limitation an initiator with a reducible linkage, one that can be cleaved to analyze the polymer on the available DMF GPC was designed, Scheme 2.

Example 3.

Growth of a Polymer from a Protein with Cleavable Linkages Between the Protein and Polymer for Measurement of Dispersity 3A. Preparation of mono-tert-butyl succinate-EBiB:

Mono-tert-butyl succinate (1.0 g, $5.74 \times 10^{-3}$ mol), hydroxyl-EBiB (1.33 g, $6.31 \times 10^{-3}$ mol), EDC-HCl (1.43 g, $7.46 \times 10^{-3}$ mol) and DMAP (0.07 g, $5.74 \times 10^{-4}$ mol) were added to a 100 mL round bottom flask. The reaction mixture was dissolved in 50 mL of dichloromethane (DCM) and stirred overnight. The reaction mixture was extracted once with 20 mL of water, twice with 1N HCl, once with 1N NaOH, once with water and brine. The organic layer was dried over anhydrous sodium sulfate and solvent was removed under reduced pressure. $^1$H NMR: 1.44 ppm (s, 9H), 1.93 ppm (d, 6H), 2.56 ppm (m, 4H) 4.36 ppm (s, 4H).

3B. COOH-tert-butyl succinate-EBiB:

Mono-tent-butyl succinate-EBiB (1 g, $2.72 \times 10^{-3}$ mol) was dissolved in 50 mL of dichloromethane and trifloroacidic acid (2.09 mL, $2.72 \times 10^{-2}$ mol) was added dropwise to the reaction mixture. The reaction was stirred for 36 hours, and subsequently extracted 3 times with 30 mL of water and once with brine. The organic phase was dried over anhydrous sodium sulfate, filtered and the solvent was removed under reduced pressure. $^1$H NMR: 1.94 ppm (d, 6H), 2.68 ppm (m, 4H) 4.38 ppm (s, 4H).

3C. NHS-tert-butyl succinate-EBiB:

Mono-tent-butyl succinate-EBiB (0.83 g, $2.69 \times 10^{-3}$ mol), EDC-HCl (0.77 g, $4.04 \times 10^{-3}$ mol) and NHS (0.46 g, $4.04 \times 10^{-3}$ mol) were dissolved in 10 mL of $CHCl_3$ and stirred for 16 hours. 40 mL of ethyl acetate and 30 mL of water were then added to the reaction mixture and stirred for 10 minuets. The organic phase was separated and the aqueous phase was washed 3 times with 20 mL of ethyl acetate. The combined organic phases were washed with brine, dried over anhydrous sodium sulfate, filtered and the solvent was removed under reduced pressure. The NHS activated initiator was directly used to modify BSA.

3D. Synthesis of BSA-O-[iBBr]$_{30}$:

NHS-ester-initiator (1) (1 g, 2.45 mmol) was dissolved in 2 mL of DMSO. BSA (1 g, 0.53 mmol Lys) was dissolved in 500 mL of 0.1 M PBS (pH 7.4) and 1 was added dropwise. The reaction was stirred overnight and purified using tangential flow filtration with a 30-kDa molecular weight cut off membrane. 15 dia-volumes of water were used to purify BSA-O-iBBr.

3E. Grafting POEOMA from $PEO_{2000}$iBBr/BSA-O-[iBBr]$_{30}$ by ATRP:

Stock solutions of CuX:L were prepared in 10 mL of deoxygenated ultra pure water as follows: X=Br, L=Bpy: Cu(I)Br (7.2 mg, 0.05 mmol), Cu(II)$Br_2$ (101.0 mg, 0.45 mmol), and Bpy (164.3 mg, 1.053 mmol). X=Cl, L=bpy: Cu(I)Cl (4.96 mg, 0.050 mmol), Cu(II)$Cl_2$ (60.5 mg, 0.25 mmol) and Bpy(164.3 mg, 1.05 mmol). X=Br, L=TPMA: Cu(I)Br (7.2 mg, 0.05 mmol), Cu(II)$Br_2$ (101.0 mg, 0.45 mmol), and TPMA (160.0 mg, 5.50 mmol). X=Cl, L=TPMA: Cu(I)Cl (4.96 mg, 0.050 mmol), Cu(II)$Cl_2$(60.5 mg, 0.25 mmol) and TPMA (160.0 mg, 5.50 mmol).

$PEO_{2000}$iBBr (10.0 mg 0.005 mmol) or BSA-O-[iBBr]$_{30}$ (12.5 mg, 0.01 mmol) was dissolved in 3.5 mL of Millipore water and placed in a 10 mL Schlenk flask. $OEOMA_{475}$ (476.2 mg, 1.14 mmol) and 50 μL of DMF (internal standard for NMR) were added dropwise to the initiator solution. The flask was sealed and nitrogen was bubbled through the solution for 20 min, while stirring, to deoxygenate the reaction mixture. After the solution was deoxygenated 1 mL of catalyst stock solution was added to the reaction mixture via a gastight syringe to initiate polymerization. The polymerization was carried out at 30° C. Samples were taken at allotted times throughout the reaction for GPC and NMR analysis.

3F. Synthesis of POEOMA by ATRP in DMSO/water from BSA-O-[iBBr]$_{30}$:

BSA-O-[iBBr]$_{30}$ (12.5 mg, 0.01 mmol) was dissolved in 3 mL of Millipore water and added to a 10 mL Schlenk flask.

OEOMA$_{475}$ (476.2 mg, 1.14 mmol) and 50 µL of DMF (internal standard for NMR) were dissolved in 500 µL of DMSO and added dropwise to the stirring protein solution (to avoid protein precipitation). The flask was sealed and bubbled for 20 min, while stirring, with nitrogen to deoxygenate the reaction mixture. After the solution was deoxygenated, 1 mL of catalyst stock solution was added to the reaction mixture to initiate polymerization. The polymerization was carried out at 30° C. Samples were taken several times throughout the reaction for GPC and NMR analysis.

Figure 14A:
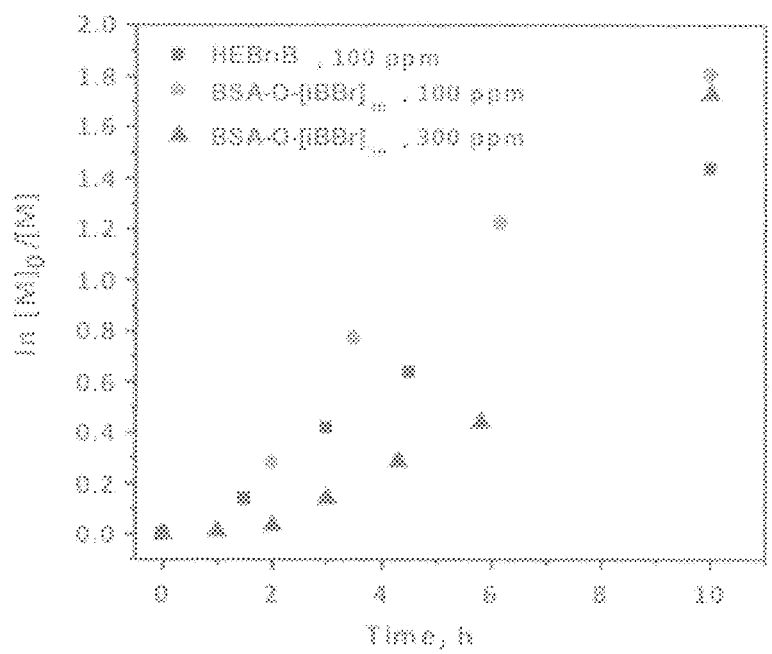
FIG. 14(A): ARGET ATRP of OEOMA$_{475}$ from HEBriB and BSA-iBBr in PBS at 30° C. First-order kinetic plot.
Figure 14B:
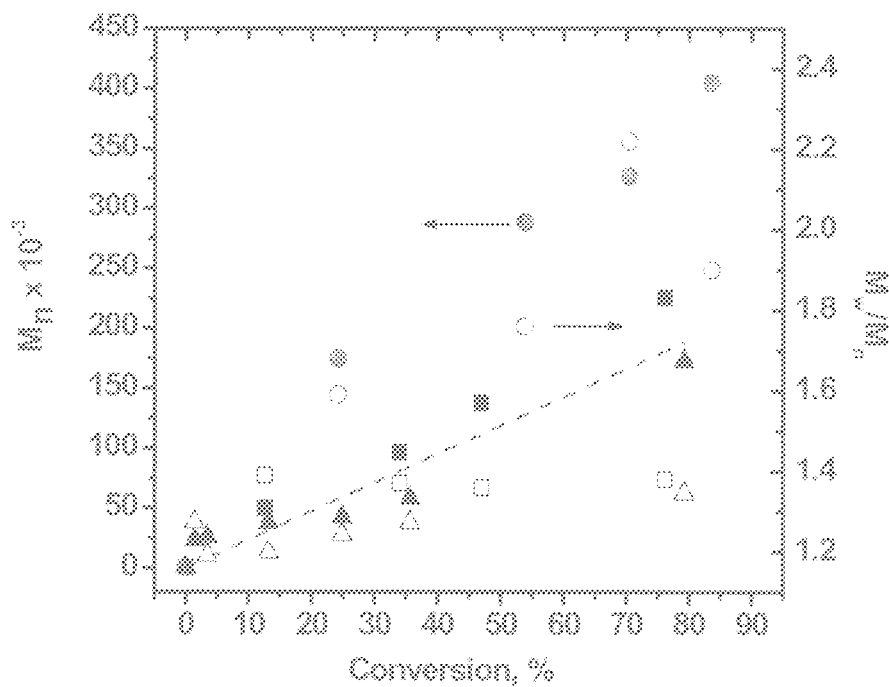
FIG. 14(B): evolution of molecular weight $M_n$ (solid shapes) and molecular weight distribution $M_w/M_n$ (open shapes) with conversion [OEOMA$_{475}$]$_0$=0.5 M, [OEOMA$_{475}$]/[I]/[TPMA]/[CuBr$_2$]=500/1/0.4/0.05, 16 nmol/min of AA; [OEOMA475]$_0$=0.25 M, [OEOMA$_{475}$]/[I]/[TPMA]/[CuBr$_2$]=250/1/0.6/0.075.

3G. Cleavage of Polymer from Protein:

Polymers were cleaved from the BSA protein by adding 200 µL of reaction mixture to 200 µL of 5% KOH solution and the resulting mixture left at room temperature for 2 hours. The results of Runs 3E and 3F are shown in FIG. 14(A) and FIG. 14(B) where it is seen that the polymerizations were controlled and the molecular weight of the "grafted from" polymer increased with conversion and the cleaved polymers possessed a narrow dispersity ~1.15 and little tailing in the GPC curves.

3H. Synthesis of P(OEOMA$_2$-co-OEOMA$_{475}$) from BSA-O-[iBBr]$_{30}$:

BSA-O-[iBBr]$_{30}$ (12.5 mg, 0.01 mmol) was dissolved in 3 mL of Millipore water and added to a 10 mL Schlenk flask. OEOMA$_{475}$ (144.7 mL, 0.50 mmol), OEOMA$_2$ (92.5 mL, 0.50 mmol) and 50 µL of DMF were dissolved in 800 µL of DMSO and slowly added dropwise to the well stirred protein solution, to avoid protein precipitation in a temporarily higher concentration of organic media. The flask was sealed and nitrogen was bubbled for 20 min, with stirring, to deoxygenate the reaction mixture. After the solution was deoxygenated, 1 mL of catalyst stock solution (X=Cl, L=Bpy) was added to the reaction mixture to initiate polymerization. Samples were taken at several times throughout the reaction for GPC and NMR analysis. Prior to DLS analysis samples were passed through a Zebra Spin desalting column to remove solvent, monomer and catalyst species. FIG. 15 shows the temperature dependent DLS spectra of the thermo-responsive grafter from (GF) BSA-O-[iBBr]$_{30}$ and the transition that occurs at the LCST of the tethered copolymer chains resulting in agglomeration of the PPCs.

Example 4.

AGET ATRP from PEO-iBBr/BSA-O-[iBBr]$_{30}$

PEO$_{2000}$iBBr (40.0 mg 0.02 mmol) or BSA-O-[iBBr]$_{30}$ (50 mg, 0.02 mmol), OEOMA$_{475}$ (2 mL, 4.54 mmol), CuBr$_2$ (44.6 mg, 0.22 mmol), and TPMA (63.8 mg, 0.22 mmol) were dissolved in 18.4 mL of pure water and charged into a 25 mL Schlenk flask. 0.4 mL of DMF was added as internal standard. Next, the reaction mixture was purged with N$_2$ for 20 minutes then placed in an oil bath at 30° C. Then AA was added either at the beginning of the reaction, or slowly fed in via a syringe pump. The results are presented in Tables 2 and 6. In Run 19 in Table 6, the reaction volume was increased from 5 mL to 20 mL to overcome limitations associated with continuous removal of samples for analysis while adding a constant amount of reducing agent. This experiment showed narrow symmetrical GPC traces with low polydispersity.

To demonstrate the versatility of the developed conditions, a well-defined thermoresponsive copolymer of MEO$_2$MA and OEOMA$_{300}$ was grafted from BSA-O-[iBBr]$_{30}$. MEO$_2$MA is marginally soluble in aqueous conditions and requires the DMSO co-solvent. Conditions and characteristics of the produced polymer are listed in the Table 3. The resulting polymer had an LCST of 52° C., FIG. 15, which was seen by a significant increase in diameter of PPH from 40 nm to 5000 nm above the LCST. This result shows that the reaction conditions developed can be used to prepare smart bio-hybrid materials.

Example 5.

ARGET from BSA

One motivation for development of the aqueous ARGET ATRP method that uses low copper concentrations and a biologically friendly reducing agent was development of biologically compatible reaction conditions. Therefore, the aqueous ARGET method is an excellent candidate for the preparation of protein-polymer hybrids by the "grafting from" approach. Bovine serum albumin (BSA) with 30 ATRP initiating sites was used as a model protein. Initially, a reaction with a small molecule initiator was performed in phosphate buffered saline (PBS). PBS is used for protein stabilization, and it consists of NaCl and NaH$_2$PO$_4$ salts. Table 14 summarizes the polymerization conditions using both a water-soluble initiator, run 1, and the protein, runs 2-3.

TABLE 14

ARGET ATRP of OEOMA$_{475}$ in PBS

| Run | M/I/TPMA/CuBr$_2$ | FA$_{AAa}$, nmol/min | Cu$^a$, ppm | Time, h | Conv., % | M$_{n\ th}^{b}$ × 10$^{-3}$ | M$_{n\ GPC}^{c}$ × 10$^{-3}$ | M$_w$/M$_n$ |
|---|---|---|---|---|---|---|---|---|
| 1 | 500/1/0.4/0.05 | 16 | 100 | 10 | 76 | 180 | 226 | 1.38 |
| 2 | 500/1/0.4/0.05 | 16 | 100 | 10 | 84 | 199 | 405 | 1.9 |
| 3 | 250/1/0.6/0.075 | 8 | 300 | 10 | 79 | 188 | 173 | 1.35 |

Entry 1: HEBriB; entries 2-3: BSA-O-[iBBr]$_{30}$. All polymerizations were conducted with [M]$_0$ = 0.5M, [I]$_0$ = 1 mM, except for entry 3: [M]$_0$ = 0.25 mM;
$^a$Calculated by the initial molar ratio of CuBr$_2$ to the monomer;
$^b$M$_{n\ th}$ = ([M]$_0$/[I]$_0$) × conversion × M$_{monomer}$;
$^c$universal calibration When the small molecule initiator was used, the polymerization in PBS showed a linear first-order kinetic plot, linear evolution of molecular weight with conversion and good correlation between experimental and theoretical molecular weight values, indicating well-controlled polymerization, FIG. 14(A) and FIG. 14(B). The dispersities were slightly higher than for polymerization carried out with only NaCl, but remained below 1.4 until ca. 80% conversion. These reaction conditions were subsequently used for the grafting from polymerization of poly(OEOMA$_{475}$) from BSA-O-[iBBr]$_{30}$. The system showed almost linear first order kinetics, however the evolution of the average molecular weight was above the theoretical values, and the M$_w$/M$_n$ values were close to 2. To improve the degree of control over the system monomer concentration was reduced from 22 vol. % to 11 vol. %, copper concentration was increased from 100 ppm to 300 ppm, and the rate of addition of ascorbic acid, $FR_{AA}$, was reduced to 8 nmol/min. The kinetics show an induction period of approximately 2 hours, after which the polymerization proceeded at an almost linear rate in semilogarithmic coordinates. The molecular weight evolution correlated well with the theoretical values, and the dispersity of the resulting polymers remained below 1.35. TEM showed that protein-polymer hybrids synthesized under these optimized conditions formed nanoparticles without aggregation.

Example 6.

ICAR from BSA

Conditions used in ICAR ATRP are very similar to protein polymerization so a natural extension into this system was conducted by employing the multifunctional BSA based initiator for an ICAR reaction. An induction period was observed and the lack of standards hampers proper analysis but the molecular weight of the hybrid material increased linearly with time reaching 30% monomer conversion 5 h after activation and PDI of cleaved polymers remained below 1.20.

Detailed Reaction Conditions:

Molar ratios: $[A(EO)_xOME]_0:[I]_0:[VA-044]_0:[CuBr_2]_0:[TPMA]_0$=400:1:0.3:0.04:0.08 in 83 mM TEABr, with $[M]_0$=0.38 M (17% monomer w/w), x is ca. 8.4. $[I]_0$ is the concentration of initiating groups from the protein. The BSA-O-iBBr multifunctional bio-macroinitiator (12.5 mg (protein), $5.0 \times 10^{-3}$ mmol (initiator)) was dissolved in 4 mL of 0.1 M TEABr and placed in a 10 mL Schlenk flask. $A(EO)_xOMe$ (1.00 g, 2.21 mmol) and 50 µl of DMF (internal standard for NMR) were dissolved in 0.920 mL of 0.1 M TEABr added dropwise to the initiator solution. An 11.3 mM $Cu^{II}Br_2$ and 23 mM TPMA stock solution (20 µL, 0.23 µmol Cu) and a 27.6 mM VA-044 stock solution (60 µL, 1.7 µmol) were added to the reaction mixture. The flask was sealed and bubbled for 20 min, while stirring, with nitrogen to deoxygenate the reaction mixture. After the solution was deoxygenated the reaction mixture was placed in a 44° C. oil bath. Samples were taken at allotted times throughout the reaction for GPC and NMR analysis. Polymers were cleaved from the protein by adding 200 µl of the reaction mixture to 200 µl of 5% KOH solution and left at room temperature for 2 hours, prior to GPC analysis.

Example 7.

eATRP Grafting from GFP

In this experiment, a modified green fluorescent protein GFP ($M_n$=30000 gmol$^{-1}$) containing the polymer initiator 4-(2'-bromoisobutyramido)phenylalanine in a specific site (*JACS*, 2010, 132, 13575-13577), was used as initiator in the ATRP of $OEO_{475}MA$. The goal was to obtained high monomer conversion, which is desired for a simple purification, with a good control, and a precise characterization of the synthesis from a kinetic point of view, aspect that is missing in the previous publication. To this end, a first polymerization with the traditional HEBriB initiator in PBS buffer and 5% of monomer was carried out (C11). Then, a second experiment with GFP-1 initiator under the same reaction conditions was carried out. The polymerization reached 95% of conversion in 3.6 hours. The first order kinetic plot indicated a constant radical concentration during the reaction.

Example 8.

Grafting from GFP

A GFP with an ester linked ATRP initiator that can be cleaved under basic conditions to provide information on the grafted from polymer segment was used. GFP-O-iBBr (0.1 mM) was used to initiate the polymerization of $OEOMA_{475}$ (5% w/vol) in 1×PBS under ARGET conditions 300 ppm Cu/L.

Reaction conditions: [GFP-O-iBBr]:[$OEOMA_{475}$]:[$CuBr_2$]:[TPMA]: 1/300/0.4/0.05 5% monomer 0.1 mM initiator 1×PBS. Ascorbic acid was injected into the reaction medium at a rate of 16 nmol/min. while the reaction was held at 30° C. over a period of 5 hours.

The polymerization yielded a well-defined PPH that retained it fluorescence compared to a T=0 sample, FIG. 16. This result is notable since it gave a direct assessment of the stability of GFP under the conditions used to prepare the GFP-b-POEOMA. Samples were taken from the ongoing grafting from GFP reaction after 1 hour and for the final sample and subjected to cleavage to provide information of the degree of control in the reaction.

Polymer cleavage conditions 5% KOH 2 hours 25° C. The cleaved polymers displayed the following $M_n$ and $M_w/M_n$.

| Time. | $M_n$. | $M_w/M_n$. |
|---|---|---|
| 1 hour | 19,000 | 1.29 |
| 5 hour | 27,800 | 1.29 |

One embodiment of the invention is conducting an ATRP reaction from a bioresponsive molecule under biologically compatible conditions wherein conditions are <20% of organic media in an aqueous solution, ambient temperature, and buffered media for preserving of protein stability.

In another embodiment these conditions also include conducting the polymerization in the presence of an excess of the deactivating species, typically $Mt^{x+1}X_{x+1}$ with a strongly bound ligand, which contributes to the control of polymerization in aqueous media exemplified but not limited to AGET and ARGET ATRP with a ratio of $CuBr_2$:AA=10:0.1, AA as reducing agent, for polymerization in water wherein there is a continuous addition of AA to keep it at low concentrations (nmol/mL) for constant generation of small amounts of activator. In a further embodiment an excess of a salt comprising a halide counterion is added to the reaction medium to promote formation of the deactivator complex.

We claim:

1. A process for forming a conjugate between a bioresponsive molecule and at least one polymer chain, the process comprising:
   polymerizing radically polymerizable monomers at a temperature of between about 4° C. and about 50° C. in the presence of an aqueous system comprising:
   a bioresponsive molecule having at least one site specific functional initiator comprising a radically transferable atom or group;
   a transition metal that participates in a reversible reduction-oxidation cycle with at least one of the site specific functional initiator and a dormant polymer chain having a radically transferable atom or group, wherein the mole fraction of transition metal in a lower, activator oxidation state to transition metal in an higher, deactivator oxidation state is less than 30%; and a ligand that forms a stable complex with the transition metal catalyst, wherein the aqueous system comprises less than 30% by weight of organic solvent and monomer concentration and the total bioresponsive molecule concentration is less than about 3 mg/mL; and forming a conjugate between the bioresponsive molecule and the at least one polymer chain, wherein the at least one polymer chain has a molecular weight distribution of no greater than or equal to 1.20.

2. The process of claim 1, wherein the transition metal has a total concentration in the system of less than 1000 ppm.

3. The process of claim 1, wherein the aqueous system comprises less than 20% by weight of organic solvent and monomer concentration.

4. The process of claim 1, wherein the aqueous system further comprises a buffer.

5. The process of claim 4, wherein the buffer is a phosphate buffer.

6. The process of claim 4, wherein the buffer has a concentration of between 1 mM to 300 mM.

7. The process of claim 4, wherein the buffer comprises the same counterion as the radically transferable atom or group.

8. The process of claim 1, wherein the bioresponsive molecule is a molecule selected from the group consisting of a protein, an enzyme, a polypeptide, a peptide, a nucleic acid, a polynucleotide, a carbohydrate, a biologically active macromolecule, and combinations of any thereof.

9. The process of claim 1, wherein the bioresponsive molecule is a protein.

10. The process of claim 9, wherein the protein retains its structure, topology and activity in the conjugate.

11. The process of claim 1, wherein the ligand is a strongly coordinating ligand.

12. The process of claim 1, wherein a fraction of the transition metal is continuously reduced from the higher, deactivator oxidation state to the lower, activator oxidation state by controlled addition of a reducing agent or by controlled degradation of an added free radical initiator.

13. The process of claim 12, wherein the mole fraction of transition metal in the activator state to transition metal in the deactivator state is less than 20%.

14. The process of claim 13, wherein the mole fraction of transition metal in the activator state to transition metal in the deactivator state is less than 10%.

15. The process of claim 1, wherein a fraction of the transition metal is continuously reduced from the higher, deactivator oxidation state to the lower, activator oxidation state by application of a potentiometric or galvanistic charge sufficient to maintain a targeted ratio of transition metal in the activator state to transition metal in the deactivator state.

16. The process of claim 1, wherein the concentration of the transition metal is from 10 ppm to 300 ppm.

17. The process of claim 1, wherein the polymerizing radically polymerizable monomers comprises grafting from the at least one polymeric chain to the bioresponsive molecule.

18. The process of claim 1, wherein the polymerizing radically polymerizable monomers is by a controlled radical polymerization process selected from a classic ATRP process, a reverse ATRP process, an AGET ATRP process, an ARGET ATRP process, an ICAR ATRP process, a RAFT polymerization process and an eATRP process.

* * * * *